US010633460B2

(12) United States Patent
Gallusser et al.

(10) Patent No.: US 10,633,460 B2
(45) Date of Patent: *Apr. 28, 2020

(54) BINDING AGENT

(71) Applicant: Roche Diagnostics Operations, Inc., Indianapolis, IN (US)

(72) Inventors: Andreas Gallusser, Penzberg (DE); Dieter Heindl, Paehl (DE); Michael Schraeml, Penzberg (DE); Christoph Seidel, Weilheim (DE); Herbert von der Eltz, Weilheim (DE)

(73) Assignee: Roche Diagnostic Operations, Inc., Indianapolis, IN (US)

( * ) Notice: Subject to any disclaimer, the term of this patent is extended or adjusted under 35 U.S.C. 154(b) by 97 days.

This patent is subject to a terminal disclaimer.

(21) Appl. No.: 15/079,897

(22) Filed: Mar. 24, 2016

(65) Prior Publication Data
US 2016/0194410 A1    Jul. 7, 2016

Related U.S. Application Data

(63) Continuation of application No. 13/923,631, filed on Jun. 21, 2013, now abandoned, which is a continuation of application No. PCT/EP2011/073633, filed on Dec. 21, 2011.

(30) Foreign Application Priority Data

Dec. 23, 2010 (EP) .................................... 10196685

(51) Int. Cl.
*C07K 16/28* (2006.01)
*C07K 19/00* (2006.01)
*C07K 16/32* (2006.01)
*C07K 16/18* (2006.01)

(52) U.S. Cl.
CPC .............. *C07K 19/00* (2013.01); *C07K 16/18* (2013.01); *C07K 16/2863* (2013.01); *C07K 16/32* (2013.01); *C07K 2317/31* (2013.01); *C07K 2317/34* (2013.01); *C07K 2317/55* (2013.01); *C07K 2317/626* (2013.01); *C07K 2317/92* (2013.01); *C07K 2317/94* (2013.01)

(58) Field of Classification Search
CPC ............ C07K 16/2863; C07K 2317/31; C07K 2317/55; C07K 16/468; C07K 2317/56; C07K 2317/35; C07K 2317/92; C07K 2317/94
See application file for complete search history.

(56) References Cited

U.S. PATENT DOCUMENTS

| | | |
|---|---|---|
| 4,948,882 A | 8/1990 | Ruth |
| 5,451,463 A | 9/1995 | Nelson et al. |
| 5,519,142 A | 5/1996 | Hoess et al. |
| 5,541,313 A | 7/1996 | Ruth |
| 5,571,894 A | 11/1996 | Wels et al. |
| 5,585,481 A | 12/1996 | Arnold, Jr. et al. |
| 5,587,458 A | 12/1996 | King et al. |
| 5,635,602 A | 6/1997 | Cantor et al. |
| 5,817,786 A | 10/1998 | Ruth |
| 5,849,878 A * | 12/1998 | Cantor ............... C07K 16/2809 530/391.9 |
| 5,849,879 A | 12/1998 | Nguyen et al. |
| 5,885,793 A | 3/1999 | Griffiths et al. |
| 5,932,448 A * | 8/1999 | Tso ..................... C07K 14/001 435/69.6 |
| 6,153,190 A | 11/2000 | Young et al. |
| 6,248,516 B1 | 6/2001 | Winter et al. |
| 6,531,581 B1 | 3/2003 | Nardone et al. |
| 2003/0219827 A1 | 11/2003 | Comb et al. |
| 2004/0224372 A1 | 11/2004 | Li et al. |
| 2005/0214833 A1 | 9/2005 | Carter et al. |
| 2006/0199207 A1 | 9/2006 | Matysiak |
| 2008/0044834 A1 | 2/2008 | Heyduk |
| 2008/0075712 A1 | 3/2008 | Haltori et al. |
| 2008/0131883 A1 | 6/2008 | Adams et al. |
| 2008/0280778 A1 | 11/2008 | Urdea |
| 2008/0312103 A1 | 12/2008 | Nemoto et al. |
| 2010/0021943 A1 | 1/2010 | An et al. |
| 2010/0062436 A1 | 3/2010 | Jarosch et al. |
| 2010/0081792 A1 | 4/2010 | Grant et al. |

(Continued)

FOREIGN PATENT DOCUMENTS

| | | |
|---|---|---|
| EP | 0061888 B1 | 10/1982 |
| EP | 0292128 A1 | 11/1988 |
| EP | 0313219 B1 | 4/1989 |

(Continued)

OTHER PUBLICATIONS

Edwards et al., J Mol Biol. 334(1): 103-118 (Year: 2003).*
Lloyd et al., Protein Engineering, Design & Selection 22:159-168 (Year: 2009).*
International Search Report dated Mar. 6, 2012 in Application No. PCT/EP2011/073633, 6 pages.
Behrens, Carsten and Dahl, Otto, "Synthesis of Achiral Linker Reagents for Direct Labelling of Oligonucleotides on Solid Supports," Nucleosides & Nucleotides, 1999, pp. 291-305, vol. 18, No. 2.
Brennan, Maureen et al., "Preparation of Bispecific Antibodies by Chemical Recombination of Monoclonal Immunoglobulin G1 Fragments," Science, Jul. 1985, pp. 81-83, vol. 229.

(Continued)

*Primary Examiner* — Phuong Huynh
(74) *Attorney, Agent, or Firm* — Stinson LLP

(57) ABSTRACT

A binding agent of the Formula A-a':a-S-b:b'-B:X(n), wherein A as well as B is a monovalent binder, a':a as well as b:b' is a binding pair wherein a' and a do not interfere with the binding of b to b' and vice versa, S is a spacer of at least 1 nm in length, :X denotes a functional moiety bound either covalently or via a binding pair to at least one of a', a, b, b' or S, (n) is an integer and at least 1, — represents a covalent bond, and the linker a-S-b has a length of 6 to 100 nm. Also disclosed are methods of producing such binding agent and certain uses thereof.

8 Claims, 15 Drawing Sheets

Specification includes a Sequence Listing.

(56) References Cited

U.S. PATENT DOCUMENTS

2010/0266617 A1  10/2010  Carven et al.

FOREIGN PATENT DOCUMENTS

| EP | 0423839 B1 | 4/1991 |
|---|---|---|
| EP | 0523978 B1 | 1/1993 |
| EP | 0618192 B1 | 10/1994 |
| EP | 0786468 B1 | 7/1997 |
| EP | 1074563 A1 | 2/2001 |
| EP | 1184665 A1 | 3/2002 |
| EP | 1186613 B1 | 3/2002 |
| EP | 1431298 B1 | 6/2002 |
| EP | 1538221 B1 | 6/2005 |
| NO | 94/04550 A1 | 3/1994 |
| NO | 94/10308 A1 | 5/1994 |
| NO | 95/05399 A1 | 2/1995 |
| NO | 97/05156 A1 | 2/1997 |
| NO | 97/43451 A1 | 11/1997 |
| NO | 99/06587 A3 | 2/1999 |
| NO | 00/06774 A1 | 2/2000 |
| NO | 01/42505 A3 | 6/2001 |
| NO | 02/18643 A2 | 3/2002 |
| NO | 03/002609 A2 | 1/2003 |
| NO | 03/019145 A3 | 3/2003 |
| WO | 89/02439 A1 | 3/1989 |
| WO | 89/02931 A1 | 4/1989 |
| WO | 89/12642 A1 | 12/1989 |
| WO | 90/08156 A1 | 7/1990 |
| WO | 92/01047 A1 | 1/1992 |
| WO | 92/11388 A1 | 7/1992 |
| WO | 92/15682 A1 | 9/1992 |
| WO | 93/05060 A1 | 3/1993 |
| WO | 93/16185 A1 | 8/1993 |
| WO | 03/104249 A3 | 12/2003 |
| WO | 2004/081051 A1 | 9/2004 |
| WO | 2005/035753 A1 | 4/2005 |
| WO | 2006/137932 A3 | 12/2006 |
| WO | WO2006/137932 * | 12/2006 |
| WO | 2007/059816 A1 | 5/2007 |
| WO | 2007/062177 A2 | 5/2007 |
| WO | 2007/069092 A3 | 6/2007 |
| WO | 2008/012543 A1 | 1/2008 |
| WO | 2008/048970 A2 | 4/2008 |
| WO | 2008/157379 A2 | 12/2008 |
| WO | 2009/072812 A2 | 6/2009 |

OTHER PUBLICATIONS

Bruck Claudine et al., "Purification of Mouse Monoclonal Antibodies from Ascitic Fluid by DEAE Affi-Gel Blue Chromatography," Methods in Enzymology, 1986, pp. 587-596, vol. 121.
Caldas, Cristina et al., Humanization of the anti-CD18 antibody 6.7: an unexpected effect of a framework residue in binding to antigen, Molecular Immunology, 2003, pp. 941-952, vol. 39.
Carter, Paul et al., "High Level *Escherichia Coli* Expression and Production of a Bivalent Humanized Antibody Fragment," Nature Bio/Technology, Feb. 1992, pp. 163-167, vol. 10.
Cheong, Hong Seok et al., "Affinity Enhancement of Biospecific Antibody Against Two Different Epitopes in the Same Antigen," Biochemical and Biophysical Research Communications, Dec. 31, 1990, pp. 795-800, vol. 173, No. 3.
Chien, Nadine C. et al., Significant structural and functional change of an antigen-binding site by a distant amino acid substitution: Proposal of a structural mechanism, Proceedings of the National Academy of Sciences USA, 1989, pp. 5532-5536, vol. 86.
Cocca, Brian A. et al., "Tandem Affinity Tags for the Purification of Bivalent Anti-DNA Single-Chain Fv Expressed in *Escherichia coli*," Protein Expression and Purification, 1999, pp. 290-298, vol. 17.
Cocuzza, Anthony J., "A Phosphoramidite Reagent for Automated Solid Phase Synthesis of 5'-Biotinylated Oligonucleotides," Tetrahedron Letters, 1989, pp. 6287-6290, vol. 30, No. 46.

De Graaf, Albert J. et al., "Nonnatural Amino Acids for Site-Specific Protein Conjugation," Bioconjugate Chemistry, Jul. 2009, pp. 1281-1295, vol. 20, No. 7.
De Kruif, John and Logtenberg, Ton, "Leucine zipper dimerized bivalent and bispecific SCFv antibodies from a phase display library [Abst. 308]," Immunotechnology, 1996, pp. 298-299, vol. 2.
De Kruif, John and Logtenberg, Ton, "Leucine Zipper Dimerized Bivalent and Bispecific scFv Antibodies from a Semi-synthetic Antibody Phase Display Library," The Journal of Biological Chemistry, 1996, pp. 7630-7634, vol. 271, No. 13.
Dong, Jianying et al., Stable IgG-like Bispecific Antibodies Directed toward the Type I Insulin-like Growth Factor Receptor Demonstrate Enhanced Ligand Blockade and Anti-tumor Activity, The Journal of Biological Chemistry, 2011, pp. 4703-4717, vol. 286, No. 6.
Fischer, Nicolas and Léger, Olivier, "Bispecific Antibodies: Molecules That Enable Novel Therapeutic Strategies," Pathobiology, 2007, pp. 3-14, vol. 74.
Francois, Christine et al., Construction of a Bispecific Antibody Reacting with the α- and β-Chains of the Human IL-2 Receptor High Affinity Cross-Linking and High Anti-Proliferative Efficiency, The Journal of Immunology, 1993, pp. 4610-4619, vol. 150, No. 10.
Frese, Marc-André and Dierks, Thomas, "Formylglycine Aldehyde Tag—Protein Engineering through a Novel Post-translational Modification," ChemBioChem, 2009, pp. 425-427, vol. 10.
Galfrè, G. and Milstein, C., "[1] Preparation of Monoclonal Antibodies: Strategies and Procedures," Methods in Enzymology, 1981, pp. 3-46, vol. 73.
Gautier, Arnaud et al., "An Engineered Protein Tag for Multiprotein Labeling in Living Cells," Chemistry & Biology, Feb. 2008, pp. 128-136, vol. 15.
Giusti,Angela et al.., Somatic diversification of S107 from an antiphosphocholine to an anti-DNA autoantibody is due to a single base change in its heavy chain variable region, Proceedings of the National Academy of Sciences USA, 1987, pp. 2926-2930, vol. 84.
Hackenberger, Christian P. R. and Schwarzer, Dirk, "Chemoselective Ligation and Modification Strategies for Peptides and Proteins," Angewandte Chemie International Edition, 2008, pp. 10030-10074, vol. 47.
Hayden, Martha S. et al., "Antibody Engineering," Current Opinion in Immunology, 1997, pp. 201-212, vol. 9.
Hey, Thomas et al., "Artificial, non-antibody binding proteins for pharmaceutical and industrial applications," Trends in Biotechnology, Oct. 2005, pp. 514-522, vol. 23, No. 10.
Hoppe, Hans-Juergen et al., "A parallel three stranded α-helical bundle at the nucleation site of collagen triple-helix formation," FEBS Letters, 1994, pp. 191-195, vol. 344.
Hudson, Peter J. and Souriau, Christelle, "Engineered antibodies," Nature Medicine, Jan. 2003, pp. 129-134, vol. 9, No. 1.
Iyer, Radhakrishnan P. et al., "Abasic oligodeoxyribonucleoside phosphorothioates: synthesis and evaluation as anti-HIV-1 agents," Nucleic Acids Research, 1990, pp. 2855-2859, vol. 18, No. 10.
Jarvius, Malin et al., In Situ Detection of Phosphorylated Platelet-derived Growth Factor Receptor β Using a Generalized Proximity Ligation Method, Molecular & Cellular Proteomics, 2007, pp. 1500-1509, vol. 6.
Kostelny, Sheri A. et al., "Formation of a Bispecific Antibody by the Use of Leucine Zippers," The Journal of Immunology, Mar. 1, 1992, pp. 1547-1553, vol. 148, No. 5.
Landschulz, William H. et al., "The Leucine Zipper: A Hypothetical Structure Common to a New Class of DNA Binding Proteins," Science, 1988, pp. 1759-1764, vol. 240.
Ledbetter, Jeffrey A. et al., CD28 Ligation in T-Cell Activation: Evidence for Two Signal Transduction Pathways, Blood, 1990, pp. 1531-1539, vol. 75, No. 7.
Lee, Seung-Hyun et al., "Humanization of an agonistic anti-death receptor 4 single chain variable fragment antibody and avidity-mediated enhancement of its cell death-inducing activity," Molecular Immunology, 2010, pp. 816-824, vol. 47.
Machida, Shinnosuke et al., Module Assembly for Protein-Surface Recognition: Geranylgeranyltransferase I Bivalent Inhibitors for Simultaneous Targeing of Interior and Exterior Protein Surfaces, Chemistry & European Journal, 2008, pp. 1392-1401, vol. 14.

(56) References Cited

OTHER PUBLICATIONS

Mann, Matthias and Jensen, Ole N., Proteomic analysis of post-translational modifications, Nature Biotechnology, 2003, pp. 255-261, vol. 21.
Mao, Hongyuan et al., Sortase-Mediated Protein Ligation: A New Method for Protein Engineering, Journal of the American Chemical Society, 2004, pp. 2670-2671, vol. 126.
McKeen, Catherine M. et al., "Synthesis of fluorophore and quencher monomers for use in Scorpion primers and nucleic acid structural probes," Organic & Biomolecular Chemistry, 2003, pp. 2267-2275, vol. 1.
Meyer, Albert et al., "Oligonucleotide Sequential Bis-Conjugation via Click-Oxime and Click-Huisgen Procedures," Journal of Organic Chemistry, 2010, pp. 3927-3930, vol. 75.
Morimoto, Koichi and Inouye, Kuniyo, "Single-step purification of F(ab')2 fragments of mouse monoclonal antibodies (immunoglobulins G1) by hydrophobic interaction high performance liquid chromatography using TSKgel Phenyl-5PW," Journal of Biochemical and Biophysical Methods, 1992, pp. 107-117, vol. 24.
Morocho, A. M. et al., "Novel Biotin Phosphoramidites with Super-long Tethering Arms," Nucleosides, Nucleotides & Nucleic Acids, 2003, pp. 1439-1441, vol. 22, Nos. 5-8.
Nelson, Paul S. et al., "Oligonucleotide labeling methods 3. Direct labeling of oligonucleotides employing a novel, non-nucleosidic, 2-aminobuytl-1, 3-propanediol backbone," Nucleic Acids Research, 1992, pp. 6253-6259, vol. 20, No. 23.
Neri, Dario et al., "High-affinity Antigen Binding by Chelating Recombinant Antibodies (CRAbs)," Journal of Molecular Biology, 1995, pp. 367-373, vol. 246.
Otrock, Zaher K. et al., Vascular endothelial growth factor family of ligands and receptors: Review, Blood Cells, Molecules & Diseases, 2007, pp. 258-268, vol. 38.
Back, Peter and Plückthun, Andreas, "Miniantibodies: Use of Amphipathic Helices To Produce Functional, Flexibly Linked Dimeric Fv Fragments with High Avidity in *Escherichia coli*," Biochemistry, Feb. 18, 1992, pp. 1579-1584 vol. 31.
Pack, Peter et al., "Tetravalent Miniantibodies with High Avidity Assembling in *Escherichia coli*," The Journal of Molecular Biology, 1995, pp. 28-34, vol. 246.
Pon, Richard T., "A Long Chain Biotin Phosphoramidite Reagent for the Automated Synthesis of 5'-Biotinylated Oligonucleotides," Tetrahedron Letters, 1991, pp. 1715-1718, vol. 32, No. 14.
Proft, Thomas, Sortase-mediated protein ligation: an emerging biotechnology tool for protein modification and immobilisation, Biotechnology Letters, 2010, pp. 1-10, vol. 32.
Prokhorenko, Igor A. et al., "Incorporation of a Pyrene Nucleoside Analogue into Synthetic Oligodeoxynucleotides Using a Nucleoside-Like Synthon," Bioorganic & Medicinal Chemistry Letters, 1995, pp. 2081-2084, vol. 5, No. 18.
Putnam, William C. and Bashkin, James K., "Synthesis and Evaluation of RNA Transesterification Efficiency Using Stereospecific Serinol-Terpyridine Conjugates," Nucleosides, Nucleotides, and Nucleic Acids, 2005, pp. 1309-1323, vol. 24, No. 9.
Ramzaeva, Natalya et al., "Oligonucleotides Functionalized by Fluorescein and Rhodamine Dyes: Michael Addition of Methyl Acrylate to 2'-Deoxypseudouridine," Helvetica Chimica Acta, 2000, pp. 1108-1126, vol. 83.
Ren, Hongjun et al., "A Biocompatible Condensation Reaction for the Labeling of Terminal Cysteine Residues on Proteins," Angewandte Chemie International Edition, 2009, pp. 9658-9662, vol. 48.
Rheinnecker, Michael et al., "Multivalent Antibody Fragments with High Functional Affinity for a Tumor-Associated Carbohydrate Antigen," The Journal of Immunology, 1996, pp. 2989-2997, vol. 157.
Roget, A. et al., "Synthesis and use of labelled nucleoside phosphoramidite building blocks bearing a reporter group: biotinyl, dinitrophenyl, pyrenyl and dansyl," Nucleic Acids Research, 1989, pp. 7643-7651, vol. 17, No. 19.
Seela, Frank and Kaiser, Klaus, "Oligodeoxyribonucleotides containing 1,3=propanediol as nucleoside substitute," Nucleic Acids Research, 1987, pp. 3113-3129, vol. 15, No. 7.
Seo, Jawon and Lee, Kong-Joo, Post-translational Modifications and Their Biological Functions: Proteomic Analysis and Systematic Approaches, Journal of Biochemistry and Molecular Biology, 2004, pp. 35-44, vol. 37, No. 1.
Su, Sheng-Hui et al., "Novel Non-Nucleosidic Phosphoramidites for Oligonucleotide Modification and Labeling," Bioorganic & Medicinal Chemistry Letters, 1997, pp. 1639-1644, vol. 7, No. 13.
Sunbul, Murat and Yin, Jun, "Site specific protein labeling by enzymatic posttranslational modification," Organic & Biomolecular Chemistry, 2009, pp. 3361-3371, vol. 7.
Taki, Masumi et al., "Transglutaminase-mediated N- and C-terminal fluorescein labeling of a protein can support the native activity of the modified protein," Protein Engineering, Design & Selection, 2004, pp. 119-126, vol. 17, No. 2.
Taylor, E. Vogel and Imperiali, B., "Native Chemical Ligation: SemiSynthesis of Post-translationally Modified Proteins and Biological Probes," Nucleic Acids and Molecular Biology, 2009, pp. 65-96, vol. 22.
Wang Charles C.-Y. et al., "Site-Specific Fluorescent Labeling of DNA Using Staudinger Ligation," Bioconjugate Chemistry, 2003, pp. 697-701, vol. 14.
Williams, Berea A. R. et al., Creating Protein Affinity Reagents by Combining Peptide Ligands on Synthetic DNA Scaffolds, Journal of the American Chemical Society, 2009, pp. 17233-17241, vol. 131.
Wojczewski, Christian et al., "Fluorescent Oligonucleotides—Versatile Tools as Probes and Primers for DNA and RNA Analysis," Synlett, 1999, pp. 1667-1678, No. 10.
Wright, Michael J. and Deonarain, Mahendra P., "Phage display of chelating recombinant antibody libraires," Molecular Immunology, 2007, pp. 2860-2869, vol. 44.
Colman, P. M., Effects of amnio acid sequence changes on antibody-antigen interactions, Research in Immunology, 1994, pp. 33-35, vol. 145, No. 1.
Harlow, Ed and Lane, David, Structure of the Antibody-Antigen Complex, Antibodies: A Laboratory Manual, 1988, pp. 23-26, Chapter 3, Cold Spring Harbor Laboratory Press, NY.
Lederman, Seth et al., A Single Amino Acid Substitution in a Common African Allele of the CD4 Molecule Ablates Binding of the Monoclonal Antibody, OKT4, Molecular Immunology, 1991, pp. 1171-1181, vol. 28, No. 11.
Mack et al., "Dependence of Avidity on Linker Length for a Bivalent Ligand Bivalent Receptor Model System," J. Am. Chem. Soc. 2012, 134:333-345.

* cited by examiner

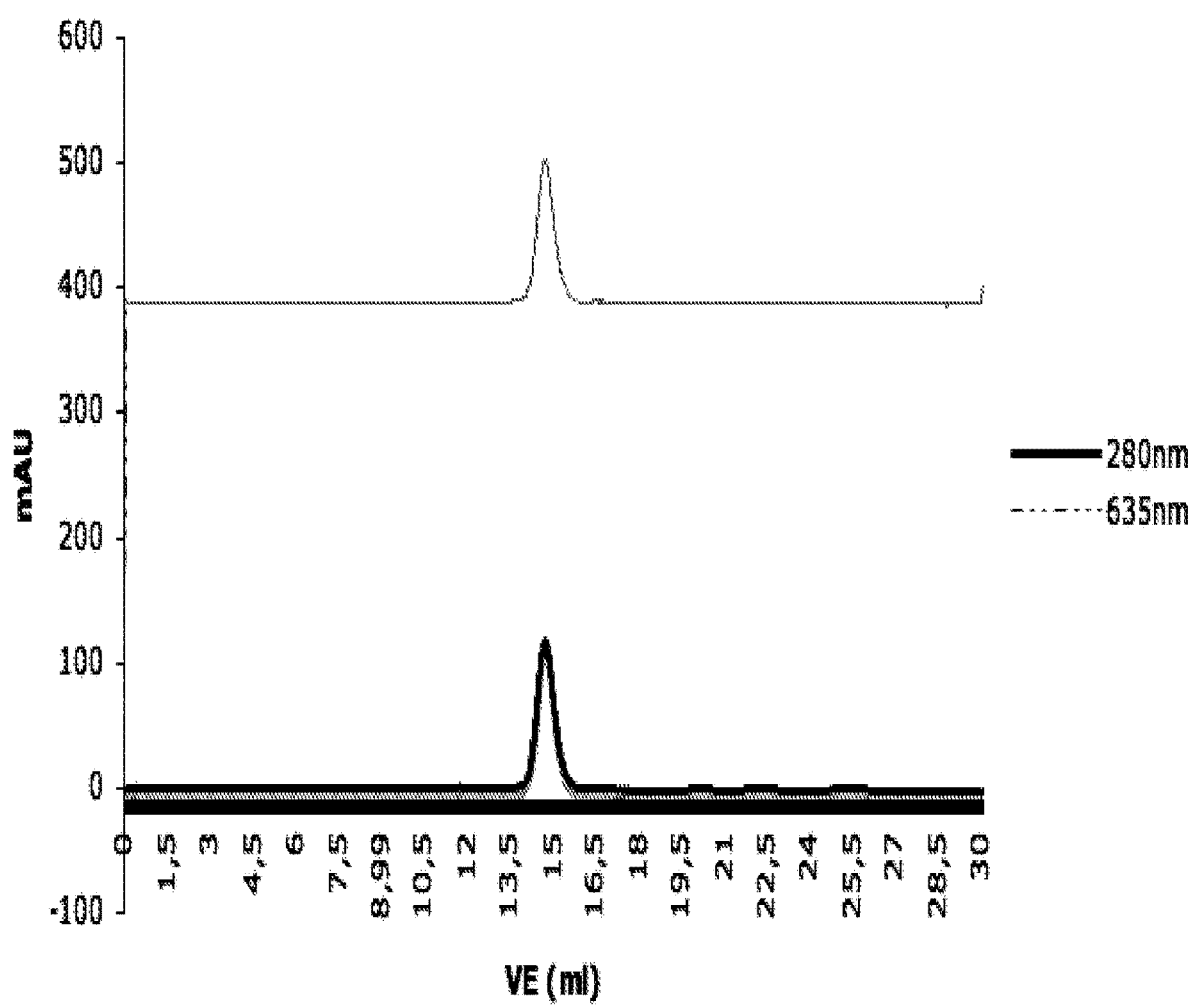

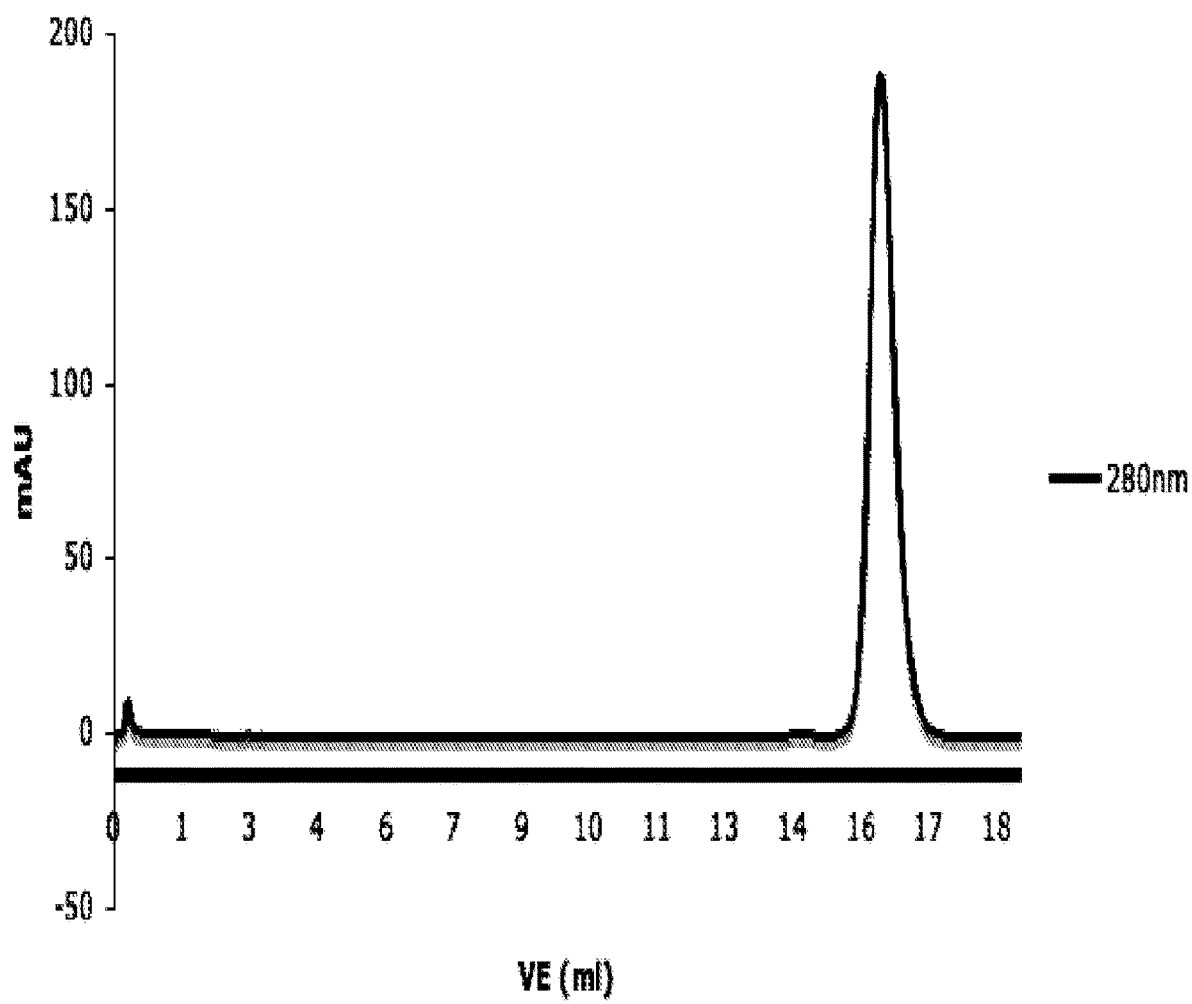

FIG. 9

| Linker | Analyte | ssFab 1 | ssFab 2 | ka (1/Ms) | kd (1/s) | t1/2 diss (min) | KD (M) | KD (nM) |
|---|---|---|---|---|---|---|---|---|
| T40 | pIGF-1R | 8.1.2 | 1.4.168 | 2,24E+06 | 2,79E-05 | 414 | 1,25E-11 | 0,01 |
| | | 8.1.2 | - | 1,17E+06 | 2,21E-02 | 0,5 | 1,89E-08 | 19 |
| | | - | 1.4.168 | 1,96E+06 | 4,19E-03 | 3 | 2,14E-09 | 2 |
| | pINR | 8.1.2 | 1.4.168 | 1,57E+06 | 3,70E-02 | 0,3 | 2,36E-08 | 24 |
| | | 8.1.2 | - | 1,36E+06 | 4,45E-02 | 0,3 | 3,27E-08 | 33 |
| | | - | 1.4.168 | n.i. | n.i. | n.i. | n.i. | n.i. |
| | IGF-1R | 8.1.2 | 1.4.168 | 2,73E+06 | 2,66E-03 | 4,3 | 9,73E-10 | 1 |
| | | 8.1.2 | - | n.i. | n.i. | n.i. | n.i. | n.i. |
| | | - | 1.4.168 | 3,30E+06 | 3,62E-03 | 3 | 1,10E-09 | 1 |
| T0 | pIGF-1R | 8.1.2 | 1.4.168 | 1,75E+06 | 6,01E-05 | 192 | 3,44E-11 | 0,03 |
| | | 8.1.2 | - | 1,03E+06 | 2,22E-02 | 1 | 2,15E-08 | 22 |
| | | - | 1.4.168 | 1,12E+06 | 2,91E-03 | 4 | 2,59E-09 | 3 |
| | pINR | 8.1.2 | 1.4.168 | 1,70E+06 | 4,18E-02 | 0,3 | 2,46E-08 | 25 |
| | | 8.1.2 | - | 1,09E+06 | 4,83E-02 | 0,2 | 4,41E-08 | 44 |
| | | - | 1.4.168 | n.d | n.d. | n.d | n.d. | n.d. |
| | IGF-1R | 8.1.2 | 1.4.168 | 1,98E+06 | 2,38E-03 | 5 | 1,20E-09 | 1 |
| | | 8.1.2 | - | n.i. | n.i. | n.i. | n.i. | n.i. |
| | | - | 1.4.168 | 2,41E+06 | 3,26E-03 | 4 | 1,35E-09 | 1 |

BINDING AGENT

CROSS-REFERENCE TO RELATED APPLICATIONS

This application is a continuation of U.S. application Ser. No. 13/923,631 filed Jun. 21, 2013 (now abandoned), which is a continuation of International Application No. PCT/EP2011/073633, filed Dec. 21, 2011, which claims the benefit of European Patent Application No. 10196685.1, filed Dec. 23, 2010, the disclosures of which are all hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jun. 19, 2013, is named SEQUENCE_LISTING_27205US.txt, and is seven thousand five hundred and nineteen bytes in size.

BACKGROUND OF THE DISCLOSURE

Bispecific antibodies, or bispecific binding agents in general, are unique in the sense that they can bind simultaneously to two different epitopes on one antigen or to two different antigens. This property enables the development of novel therapeutic and diagnostic strategies that are not possible with conventional monoclonal antibodies. A large panel of bispecific dual binders, e.g. of bispecific antibody formats has been developed and reflects the strong scientific as well as commercial interest in these molecules.

Monoclonal antibodies (mAbs), being directed towards single epitopes on the antigen, usually bind with affinities which are less than the avidity of polyclonal antisera. However, certain pairs of mAbs directed towards different epitopes on the same antigen can bind that antigen more effectively and with an avidity greater than the sum of the affinities of the corresponding individual mAb alone.

However, the avidity constants for synergizing pairs of mAb or for a chemically cross-linked bispecific F(ab')2 is generally only up to 15 times greater than the affinity constants for the individual mAb, which is significantly less than the theoretical avidity expected for ideal combination between the reactants (Cheong, H. S., et al., Biochem. Biophys. Res. Commun. 173 (1990) 795-800). One reason for this might be that the individual epitope/paratope interactions involved in a synergistic binding (resulting in a high avidity) must be orientated in a particular way relative to each other for optimal synergy.

BRIEF SUMMARY OF THE DISCLOSURE

The present disclosure relates to a binding agent of the Formula A-a':a-S-b:b'-B:X(n), wherein A as well as B is a monovalent binder, wherein a':a as well as b:b' is a binding pair wherein a' and a do not interfere with the binding of b to b' and vice versa, wherein S is a spacer of at least 1 nm in length, wherein :X denotes a functional moiety bound either covalently or via a binding pair to at least one of a', a, b, b' or S, wherein (n) is an integer and at least 1, wherein — represents a covalent bond, and wherein the linker a-S-b has a length of 6 to 100 nm. Also disclosed are a method of producing such binding agent and certain uses thereof.

The present disclosure relates to a binding agent of the Formula A-a':a-S-b:b'-B:X(n), wherein A as well as B is a monovalent binder, wherein a':a as well as b:b' is a binding pair wherein a' and a do not interfere with the binding of b to b' and vice versa, wherein S is a spacer of at least 1 nm in length, wherein :X denotes a functional moiety bound either covalently or via a binding pair to at least one of a', a, b, b' or S, wherein (n) is an integer and at least 1, wherein — represents a covalent bond, and wherein the linker a-S-b has a length of 6 to 100 nm.

Further disclosed is a method of making such binding agent and the use of such agent. e.g. in an immunoassay procedure.

The use of the novel binding agent, especially in an immunological detection procedure is also described and claimed

BRIEF DESCRIPTION OF THE FIGURES

The features of this disclosure, and the manner of attaining them, will become more apparent and the disclosure itself will be better understood by reference to the following description of embodiments of the disclosure taken in conjunction with the accompanying drawing.

FIG. 1A is an analytical gel filtration experiments assessing efficiency of the anti-pIGF1-R dual binder assembly. Diagrams A, B and C show the elution profile of the individual dual binder components (flourescein-ssFab' 1.4.168, Cy5-ssFab' 8.1.2 and linker DNA (T=0); Fab' denotes an Fab'-fragment conjugated to a single-stranded oligonucleotide). Diagram D shows the elution profile after the 3 components needed to form the bi-valent binding agent had been mixed in a 1:1:1 molar ratio. The thicker (bottom) curve represents absorbance measured at 280 nm indicating the presence of the ssFab' proteins or the linker DNA, respectively. The thinner top curve in B) and D) (absorbance at 495 nm) indicates the presence of fluorescein and the thinner top curve in a) and the middle curve in d) (absorbance at 635 nm) indicates the presence of Cy5. Comparison of the elution volumes of the single dual binder components ($VE_{ssFab'\ 1.4.168}$~15 ml; $VE_{ssFab'\ 8.1.2}$~15 ml; $VE_{linker}$~16 ml) with the elution volume of the reaction mix ($VE_{mix}$~12 ml) demonstrates that the dual binder assembly reaction was successful (rate of yield: ~90%). The major 280 nm peak that represents the eluted dual binder nicely overlaps with the major peaks in the 495 nm and 635 nm channel, proving the presence of both ssFab' 8.1.2 and ssFab'1.4.168 in the peak representing the bi-valent binding agent.

FIG. 1C is an analytical gel filtration experiments assessing efficiency of the anti-pIGF1-R dual binder assembly. Diagrams A, B and C show the elution profile of the individual dual binder components (flourescein-ssFab' 1.4.168, Cy5-ssFab' 8.1.2 and linker DNA (T=0); Fab' denotes an Fab'-fragment conjugated to a single-stranded oligonucleotide). Diagram D shows the elution profile after the 3 components needed to form the bi-valent binding agent had been mixed in a 1:1:1 molar ratio. The thicker (bottom) curve represents absorbance measured at 280 nm indicating the presence of the ssFab' proteins or the linker DNA, respectively. The thinner top curve in B) and D) (absorbance at 495 nm) indicates the presence of fluorescein and the thinner top curve in a) and the middle curve in d) (absorbance at 635 nm) indicates the presence of Cy5. Comparison of the elution volumes of the single dual binder components ($VE_{ssFab'\ 1.4.168}$~15 ml; $VE_{ssFab'\ 8.1.2}$~15 ml; $VE_{linker}$~16 ml) with the elution volume of the reaction mix ($VE_{mix}$~12 ml) demonstrates that the dual binder assembly reaction was successful (rate of yield: ~90%). The major 280 nm peak that represents the eluted dual binder nicely overlaps with the major peaks in the 495 nm and 635 nm channel, proving the presence of both ssFab' 8.1.2 and ssFab'1.4.168 in the peak representing the bi-valent binding agent.

FIG. 9 presents kinetic data of the Dual Binder experiment. T40-T-Bi (linker dual binder with ssFab' 8.1.2 and ssFab' 1.4.168 (=T40 in the Figure) shows a 1300-fold lower off-rate (kd=2.79E-05/s) versus pIR when compared to pIR (kd=3.70E-02/s).

A concentration series of the pIGF-1R peptide was injected at 30 nM, 10 nM, 2×3.3 nM, 1.1 nM, 0.4 nM, 0 nM. The corresponding data are given in the table of FIG. 9.

Figure 8:
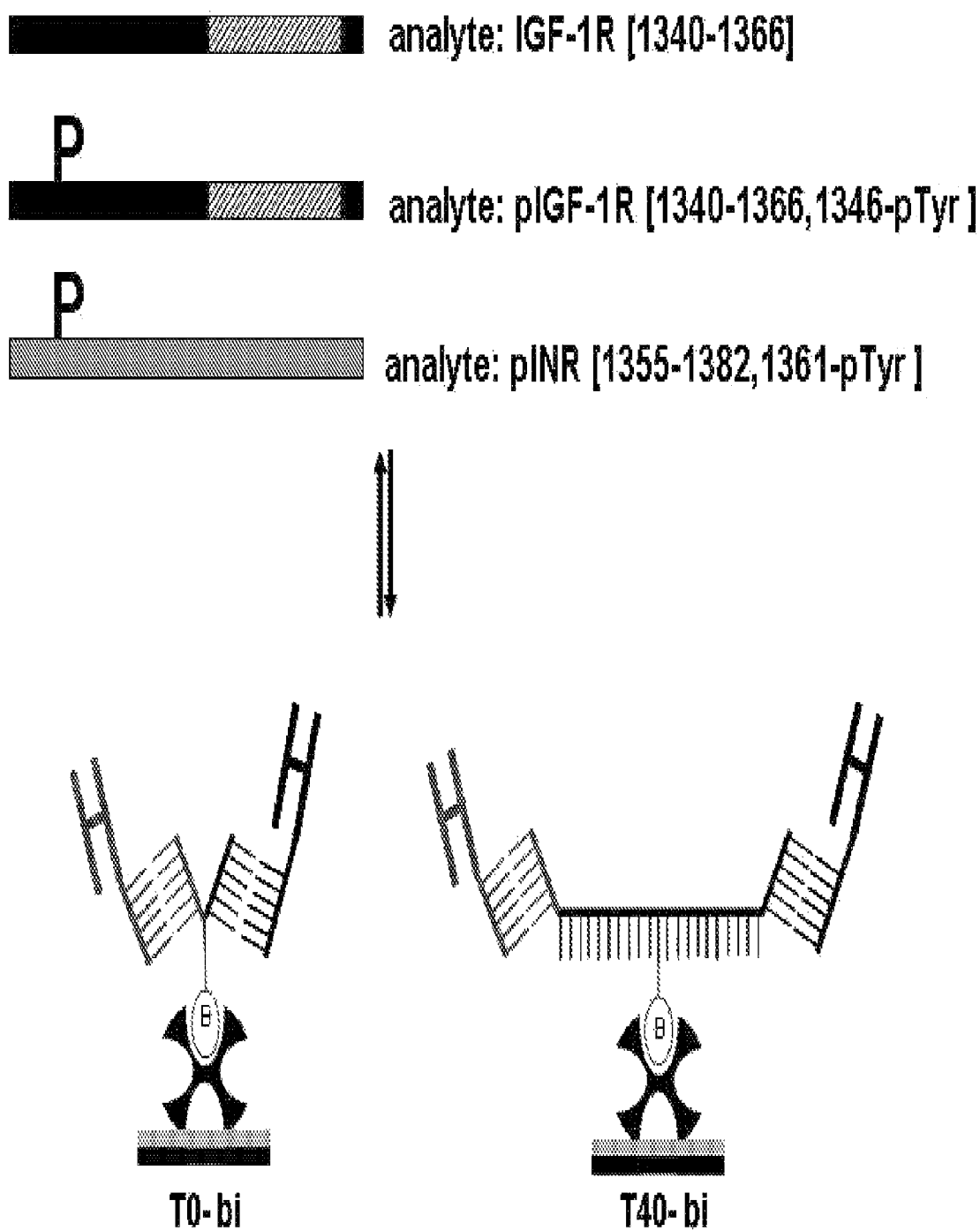
FIG. 8 presents a schematic drawing of the Biacore™ assay, presenting the biotinylated dual binders on the sensor surface. On Flow Cell 1 (=FC1) (not shown) amino-PEO-biotin was captured. On FC2, FC3 and FC4 bi-valent binding agents with increasing linker length were immobilized. (shown are the dual binders on FC2 (T0-bi=only one central T-Bi) and FC4 (T40-bi=one central T-Bi and 20 Ts each up- and downstream), respectively). Analyte 1: IGF-1R-peptide containing the M-1.4.168 ssFab' epitope at the right hand end of the peptide (top line)—the M-8.1.2 ssFab' phospho-epitope is not present, because this peptide is not phosphorylated; analyte 2: pIGF-1R peptide containing the M-8.1.2 ssFab' phospho-epitope (P) and the M-1.4.168 ssFab' epitope (second line); analyte 3: pIR peptide, containing the cross reacting M-8.1.2 ssFab' phospho-epitope, but not the epitope for M-1.4.168 (third line).
Figure 11:
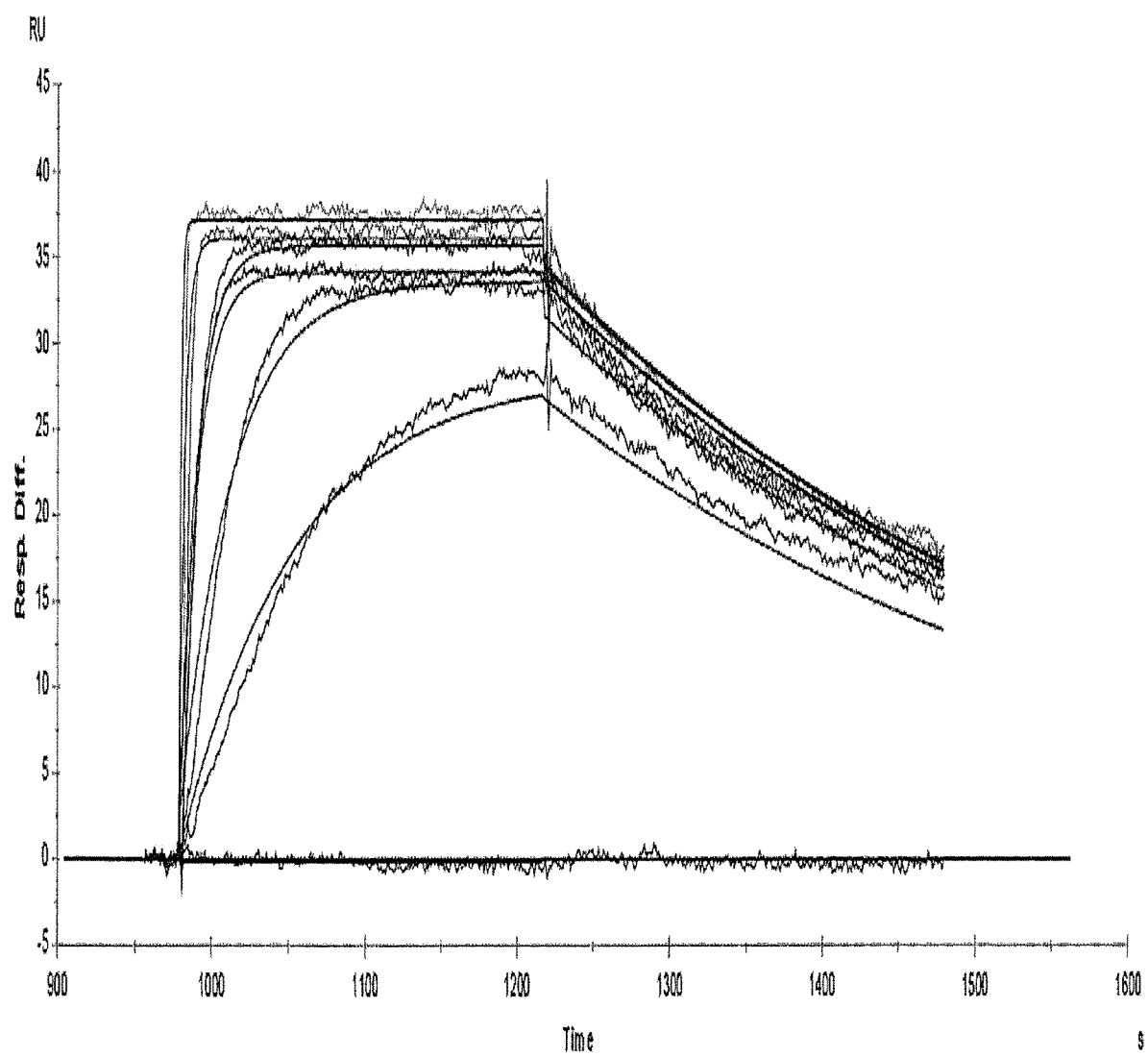

FIG. 11 presents a Biacore™ sensorgram, showing concentration dependent measurement of the T40-T-Bi dual binding agent vs. the IGF-1R peptide (the non-phosphorylated IGF-1R peptide). The assay setup was as depicted in FIG. 8. A concentration series of the IGF-1R peptide was injected at 300 nM, 100 nM, 2×33 nM, 11 nM, 4 nM, 0 nM. The corresponding data are given in the table of FIG. 9.

Figure 12:
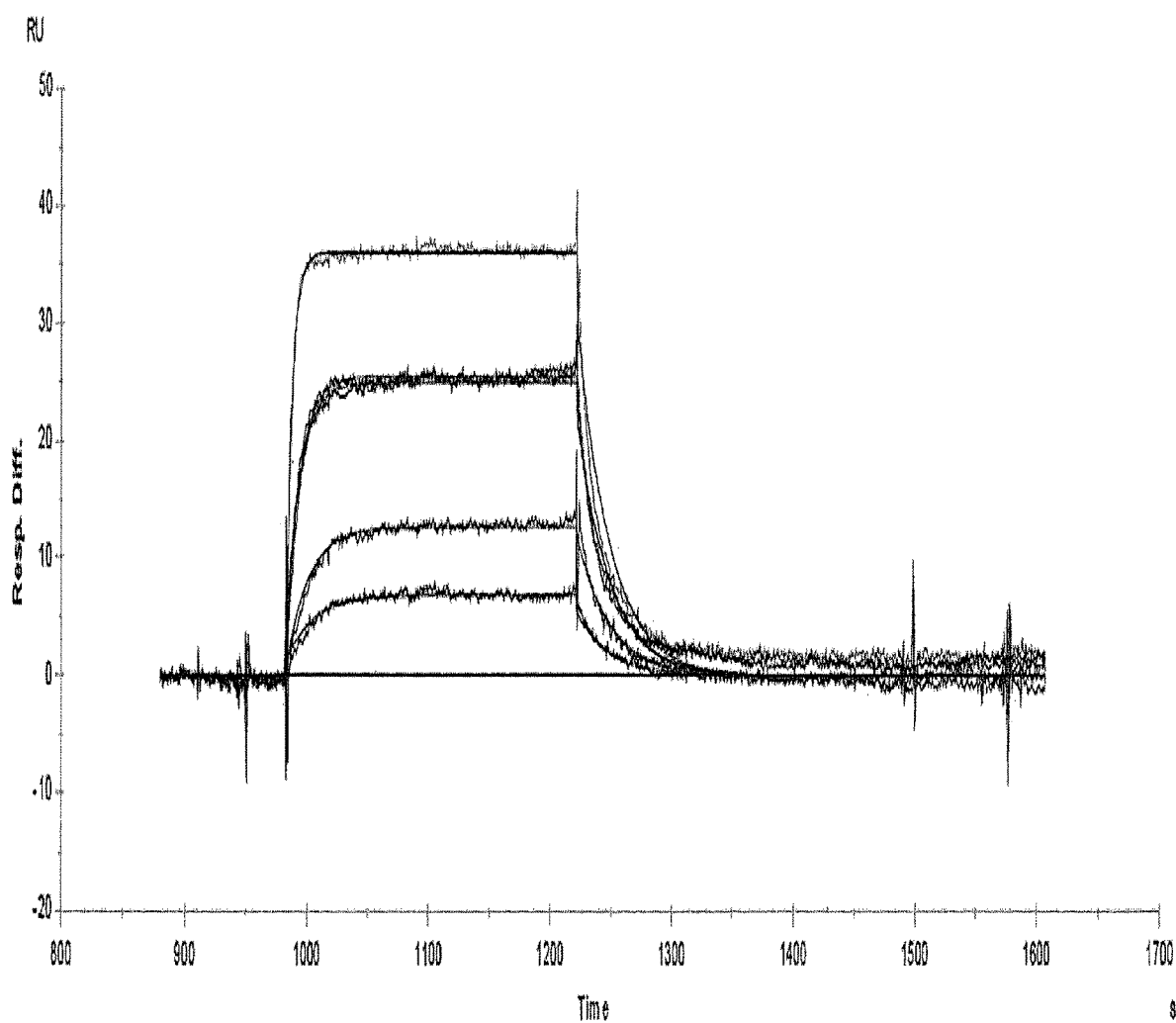

FIG. 12 presents a Biacore™ sensorgram, showing concentration dependent measurement of the T40-T-Bi dual binding agent vs. the pIR peptide (the phosphorylated insulin receptor peptide). The assay setup was as depicted in FIG. 8. A concentration series of the pIR peptide was injected at 100 nM, 2×33 nM, 11 nM, 4 nM, 0 nM. The corresponding data are given in the table depicted as FIG. 9.

Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

BRIEF DESCRIPTION OF THE SEQUENCE LISTING

1. Antibody Fragments.
SEQ ID NO:1 $V_H$ (mAb 1.4.168): QCDVKLVESG GGLVKPGGSL KLSCAASGFT FSDYPMSWVR QTPEKRLEWV ATITTGGTYT YYPDSIKGRF TISRD-NAKNT LYLQMGSLQS EDAAMYYCTR VKTDLW-WGLA YWGQGTLVTV SA
SEQ ID NO:2 $V_L$ (mAb 1.4.168): QLVLTQSSSA SFSLGA-SAKL TCTLSSQHST YTIEWYQQQP LKPPKYVMEL KKDGSHTTGD GIPDRFSGSS SGADRYLSIS NIQ-PEDESIY ICGVGDTIKE QFVYVFGGGT KVTVLG
SEQ ID NO:3 $V_H$ (mAb 8.1.2): EVQLQQSGPA LVKP-GASVKM SCKASGFTFT SYVIHWVKQK PGQ-GLEWIGY LNPYNDNTKY NEKFKGKATL TSDRSSSTVY MEFSSLTSED SAVYFCARRG IYAYD-HYFDY WGQGTSLTVS S
SEQ ID NO:4 $V_L$ (mAb 8.1.2): QIVLTQSPAI MSASPGEKVT LTCSASSSVN YMYWYQQKPG SSPRLLIYDT SNLASGVPVR FSGSGSVTSY SLTISRMEAE DAATYYCQQW STYPLTFGAG TKLELK 2. Sequences of ssDNA
a) 17mer ssDNA (covalently bound with 5' end to Fab' of anti-TroponinT MAB a or Fab' 1.4.168 to IGF-1R, respectively): 5'-AGT TCT ATC GTC GTC CA-3'(SEQ ID NO:5)
b) 19mer ssDNA (covalently bound with 3' end to Fab' of anti-TroponinT MAB b or Fab' 8.1.2 to phosphorylated IGF-1R, respectively): 5'-A GTC TAT TAA TGC TTC TGC-3'(SEQ ID NO:6)
c) complementary 19mer ssDNA (used as part of a linker): 5'-G CAG AAG CAT TAA TAG ACT-3'(SEQ ID NO:7)
d) complementary 17mer ssDNA (used as part of a linker): 5'-TGG ACG ACG ATA GAA CT-3'(SEQ ID NO:8)

3. Sequences of Troponin T Epitopes:
SEQ ID NO:9=ERAEQQRIRAEREKEUUS-LKDRIEKRRRAERAEamide, wherein U represents β-Alanin. (The epitope "A" for antibody anti-Troponin antibody a.)
SEQ ID NO:10=SLKDRIERRRAERAEOOERAEQQRI-RAEREKEamide, wherein O represents Amino-trioxa-octanoic-acid. (The epitope "B" for antibody anti-Troponin antibody b.)

4. Sequences of IGF-1R/IR Epitopes:
SEQ ID NO:11=FDERQPYAHMNGGRKNERAL-PLPQSST; IGF-1R (1340-1366)
SEQ ID NO:12=YEEHIPYTHMNGGKKNGRILTL-PRSNPS; hIR(1355-1382)

5. Protein Linker and Tag-Sequences:
SEQ ID NO:13=GGGGS (=G4S) motif (e.g. as part of a polypeptide linker)
SEQ ID NO:14=YPYDVPDYA (HA-Tag)
SEQ ID NO:15=GLNDIFEAQKIEWHE (Avi-Tag)

Although the sequence listing represents an embodiment of the present disclosure, the sequence listing is not to be construed as limiting the scope of the disclosure in any manner and may be modified in any manner as consistent with the instant disclosure and as set forth herein.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

The present disclosure relates to a binding agent of the Formula: A-a':a-S-b:b'-B:X(n), wherein A as well as B is a monovalent binder, wherein a':a as well as b:b' is a binding pair wherein a' and a do not interfere with the binding of b to b' and vice versa, wherein S is a spacer of at least 1 nm in length, wherein :X denotes a functional moiety bound either covalently or via a binding pair to at least one of a', a, b, b' or S, wherein (n) is an integer and at least 1, wherein — represents a covalent bond, and wherein the linker a-S-b has a length of 6 to 100 nm. As obvious the binding agent according to the present disclosure is a binding agent comprising at least two monovalent binders of different specificity. In one embodiment the binding agent according to the present disclosure comprises two monovalent binders. In one embodiment the binding agent according to the present disclosure is a bi-valent or dual binding agent.

The generation of bispecific antibodies is e.g. described in WO 2004/081051. In this application a bispecific antibody (BAb) comprising two antibodies, each of which has a binding specificity to a different epitope situated on the surface of a target structure are disclosed. In order to achieve the desired improvement in specificity two MAbs are used each having a relatively low binding affinity for its respective epitope. The BAbs produced provide high avidity for target tissue due to the cumulative nature of the binding interactions but have much lower affinity for cross-reactive non-target tissue due to the lower affinity of the individual MAbs used to produce them. Production of these bispecific antibodies is quite complex and e.g. requires sophisticated chemical coupling and purification steps.

Bispecific monoclonal antibodies also represent quite interesting novel therapeutic modalities. A broad spectrum of bispecific antibody formats has been designed and developed (see e.g. Fischer, N. and Leger, O., Pathobiology 74 (2007) 3-14). Such bispecific therapeutic monoclonals can e.g. be obtained by chemical cross-linking, interaction of appropriately engineered protein domains, completely recombinant, etc..... Obviously, recombinant engineering of each of the binders and careful purification of the desired heterodimer from biochemically alike homo-dimers represent some of the challenges encountered.

Chelating recombinant antibodies (CRAbs), originally described by Neri, D. et al. (1995) represent a species of very high affinity antibodies, where two scFvs specific for non-overlapping epitopes on the same antigen molecule are connected by a flexible linker polypeptide. The original modeled and designed anti-hen egg lysozyme (HEL) CRAB employed an 18 amino acid linker polypeptide to span the distance between the two scFv antibodies and the resulting affinity enhancement was subsequently shown to be up to 100-fold higher than the superior of the two scFvs as shown by a variety of biophysical methods (Neri, D. et al., J. Mol. Biol. 246 (1995) 367-373).

Wright M. J. and Deonarain M. P., (Molecular Immunology 44 (2007) 2860-2869) developed a phage display library for generation of chelating recombinant antibodies. The library described there uses expression vectors construed in such way to provide for dual binders having linker peptides of various length in between the two binding entities. Selection of the best binder, i.e. the dual binder with the optimal length of such linker, is thereby facilitated. However, for each such chelating recombinant antibody a full library of recombinant expression systems (allowing for expression of a "binder 1-linker (of variable length)-binder 2" polypeptide) has to be construed.

As outlined above in a cursory manner, the manufacturing of bispecific dual binders remains quite challenging and requires sophisticated techniques to identify, construe and produce individually each of those bispecific binding agents. The frequent need for derivatizing, e.g., labeling such a bispecific binding agent even adds a further level of complexity.

The instant disclosure provides the surprising disclosure and findings that at least some of the disadvantages known from the prior art can be overcome by way of the novel bispecific binding agents and methods disclosed in the present embodiment.

As the skilled artisan will appreciate the binding agent described in the present disclosure can be isolated and purified as desired. In one embodiment the present disclosure relates to an isolated binding agent as disclosed herein. An "isolated" binding agent is one which has been identified and separated and/or recovered from e.g. the reagent mixture used in the synthesis of such binding agent. Unwanted components of such reaction mixture are e.g. monovalent binders that did not end up in the desired binding agent. In one embodiments, the binding agent is purified to greater than 80%. In some embodiments, the binding agent is purified to greater than 90%, 95%, 98% or 99% by weight, respectively. In case both monovalent binders of the binding agent according to the present disclosure are polypeptides purity is e.g. easily determined by SDS-PAGE under reducing or nonreducing conditions using, for example, Coomassie blue or silver stain in protein detection. In case purity is assessed on the nucleic acid level, size chromatography is applied to separate the binding agent from side products and the OD at 260 nm is monitored to assess its purity.

The articles "a" and "an" are used herein to refer to one or to more than one (i.e., to at least one) of the grammatical object of the article. By way of example, "an antibody" means one antibody or more than one antibody.

The terms "polypeptide" and "protein" are used interchangeably. A polypeptide in the sense of the present disclosure consists of at least 5 amino acids linked by alpha amino peptidic bonds.

A "target molecule" is a biomolecule of interest for which a method for determination or measurement is sought. Exemplary target molecules are lipoproteins, polypeptides, complexes of polypeptides, secondarily modified polypeptides and complexes between polypeptides and nucleic acids. In one embodiment a target molecule is a polypeptide.

A "monovalent binder" (A and B, respectively, in Formula I) according to the present disclosure is a molecule interacting with a target molecule, e.g. with a target polypeptide at a single site (i.e. the specific binding site). In case monovalent antibodies or antibody fragments are used as a binder this site is called the paratop.

As will be appreciated, the monovalent binders A and B, respectively, each specifically bind their corresponding antigen. In an exemplary embodiment the epitopes specifically bound by the monovalent binders A and B do not overlap. As the skilled artisan will appreciate the term specific is used to indicate that other biomolecules present in the sample do not significantly bind to the binding agent used. In some embodiments, for a specific binder the level of binding affinity to a biomolecule other than the target molecule results in a binding affinity which is only 10% or less, for example, in some embodiments only 5% or less of the affinity it has to the specifically bound target molecule.

Examples of monovalent binders are peptides, peptide mimetics, aptamers, spiegelmers, darpins, ankyrin repeat proteins, Kunitz type domains, single domain antibodies (see: Hey, T. and Fiedler, E., et al., Trends Biotechnol. 23 (2005) 514-522), and monovalent fragments of antibodies.

In certain embodiments the monovalent binder is a polypeptide. In exemplary embodiments each of the monovalent binders A and B, respectively is a polypeptide.

In certain embodiments the monovalent binder A and B, respectively, is a monovalent antibody fragment, for example a monovalent fragment derived from a monoclonal antibody.

Monovalent antibody fragments include, but are not limited to Fab, Fab'-SH, single domain antibody, Fv, and scFv fragments, as provided below.

In exemplary embodiments at least one of the monovalent binders is a single domain antibody, an Fab-fragment or an Fab'-fragment of a monoclonal antibody.

It also represents an exemplary embodiment that in the binding agent disclosed herein both the monovalent binders are derived from monoclonal antibodies and are Fab-fragments, or Fab'-fragments or an Fab-fragment and an Fab'-fragment. Also, some embodiments include the binding agent comprising two Fab-fragments as the monovalent binders A and B.

Monoclonal antibody techniques allow for the production of extremely specific binding agents in the form of specific monoclonal antibodies or fragments thereof. Particularly well known in the art are techniques for creating monoclonal antibodies, or fragments thereof, by immunizing mice, rabbits, hamsters, or any other mammal with a polypeptide of interest. Another method of creating monoclonal antibodies, or fragments thereof, is the use of phage libraries of sFv (single chain variable region), specifically human sFv. (See e.g., Griffiths et al., U.S. Pat. No. 5,885,793; McCafferty et al., WO 92/01047; Liming et al., WO 99/06587).

Antibody fragments may be generated by traditional means, such as enzymatic digestion or by recombinant techniques. For a review of certain antibody fragments, see Hudson, P. J. et al., Nat. Med. 9 (2003) 129-134.

An Fv is a minimum antibody fragment that contains a complete antigen-binding site and is devoid of constant region. In one embodiment, a two-chain Fv species consists of a dimer of one heavy- and one light-chain variable domain in tight, non-covalent association. In one embodiment of a single-chain Fv (scFv) species, one heavy- and one light-chain variable domain can be covalently linked by a flexible peptide linker such that the light and heavy chains can associate in a dimeric structure analogous to that in a two-chain Fv species. For a review of scFv, see, e.g., Plueckthun, In: The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. Generally, six hyper variable regions (HVRs) confer antigen-binding specificity to an antibody. However, even a single variable domain (or half of an Fv comprising only three HVRs specific for an antigen) has the ability to recognize and bind antigen.

An Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group.

Various techniques have been developed for the production of antibody fragments. Traditionally, antibody fragments were derived via proteolytic digestion of intact antibodies (see, e.g., Morimoto, K. et al., Journal of Biochemical and Biophysical Methods 24 (1992) 107-117; and Brennan, M. et al., Science 229 (1985) 81-83). For example, papain digestion of antibodies produces two identical antigen-binding fragments, called "Fab" fragments, each with a single antigen-binding site, and a residual "Fc" fragment, whose name reflects its ability to crystallize readily.

Antibody fragments can also be produced directly by recombinant host cells. Fab, Fv and scFv antibody fragments can all be expressed in and secreted from *E. coli*, thus allowing the facile production of large amounts of these fragments. Antibody fragments can be isolated from the antibody phage libraries according to standard procedures. Alternatively, Fab'-SH fragments can be directly recovered from *E. coli*. (Carter, P. et al., Bio/Technology 10 (1992) 163-167). Mammalian cell systems can be also used to express and, if desired, secrete antibody fragments.

In certain embodiments, a monovalent binder of the present disclosure is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

The term "oligonucleotide" or "nucleic acid sequence" as used herein, generally refers to short, generally single stranded, polynucleotides that comprise at least 8 nucleotides and at most about 1000 nucleotides. In an exemplary embodiment an oligonucleotide will have a length of at least 9, 10, 11, 12, 15, 18, 21, 24, 27 or 30 nucleotides. In an exemplary embodiment an oligonucleotide will have a length of no more than 200, 150, 100, 90, 80, 70, 60, 50, 45, 40, 35 or 30 nucleotides. The description given below for polynucleotides is equally and fully applicable to oligonucleotides.

The term oligonucleotide is to be understood broadly and includes DNA and RNA as well as analogs and modification thereof.

An oligonucleotide may for example contain a substituted nucleotide carrying a substituent at the standard bases deoxyadenosine (dA), deoxyguanosine (dG), deoxycytosine (dC), deoxythymidine (dT), deoxyuracil (dU). Examples of such substituted nucleobases are: 5-substituted pyrimidines like 5 methyl dC, aminoallyl dU or dC, 5-(aminoethyl-3-acrylimido)-dU, 5 propinyl dU or dC, 5 halogenated-dU or dC; N substituted pyrimidines like N4 ethyl dC; N substituted purines like N6 ethyl dA, N2 ethyl dG; 8 substituted purines like 8-[6-amino)-hex-1-yl]-8-amino-dG or dA, 8 halogenated dA or dG, 8-alkyl dG or dA; and 2 substituted dA like 2 amino dA.

An oligonucleotide may for example contain a substituted nucleotide carrying a substituent at the standard bases deoxyadenosine (dA), deoxyguanosine (dG), deoxycytosine (dC), deoxythymidine (dT), deoxyuracil (dU). Examples of such substituted nucleobases are: 5-substituted pyrimidines like 5 methyl dC, aminoallyl dU or dC, 5-(aminoethyl-3-acrylimido)-dU, 5-propinyl-dU or -dC, 5 halogenated-dU or -dC; N substituted pyrimidines like N4-ethyl-dC; N substituted purines like N6-ethyl-dA, N2-ethyl-dG; 8 substituted purines like 8-[6-amino)-hex-1-yl]-8-amino-dG or -dA, 8 halogenated dA or dG, 8-alkyl dG or dA; and 2 substituted dA like 2 amino dA.

An oligonucleotide may contain a nucleotide or a nucleoside analog. I.e. the naturally occurring nucleobases can be exchanged by using nucleobase analogs like 5-Nitroindol d riboside; 3 nitro pyrrole d riboside, deoxyinosine (dI), deoxyxanthosine (dX); 7 deaza-dG, -dA, -dI or -dX; 7-deaza-8-aza-dG, -dA, -dI or -dX; 8-aza-dA, -dG, -dI or -dX; d Formycin; pseudo dU; pseudo iso dC; 4 thio dT; 6 thio dG; 2 thio dT; iso dG; 5-methyl-iso-dC; N8-linked 8-aza-7-deaza-dA; 5,6-dihydro-5-aza-dC; and etheno-dA or pyrollo-dC. As obvious to the skilled artisan, the nucleobase in the complementary strand has to be selected in such manner that duplex formation is specific. If, for example, 5-methyl-iso-dC is used in one strand (e.g. (a)) iso dG has to be in the complementary strand (e.g. (a')).

The oligonucleotide backbone may be modified to contain substituted sugar residues, sugar analogs, modifications in the internucleoside phosphate moiety, and/or be a PNA.

An oligonucleotide may for example contain a nucleotide with a substituted deoxy ribose like 2'-methoxy, 2'-fluoro, 2'-methylseleno, 2'-allyloxy, 4'-methyl dN (wherein N is a nucleobase, e.g., A, G, C, T or U).

Sugar analogs are for example Xylose; 2',4' bridged Ribose like (2'-O, 4'-C methylene)-(oligomer known as LNA) or (2'-O, 4'-C ethylene)-(oligomer known as ENA); L-ribose, L-d-ribose, hexitol (oligomer known as HNA); cyclohexenyl (oligomer known as CeNA); altritol (oligomer known as ANA); a tricyclic ribose analog where C3' and C5' atoms are connected by an ethylene bridge that is fused to a cyclopropane ring (oligomer known as tricycloDNA); glycerin (oligomer known as GNA); Glucopyranose (oligomer known as Homo DNA); carbaribose (with a cyclopentan instead of a tetrahydrofuran subunit); hydroxymethyl-morpholin (oligomers known as morpholino DNA).

A great number of modification of the internucleosidic phosphate moiety are also known not to interfere with hybridization properties and such backbone modifications can also be combined with substituted nucleotides or nucleotide analogs. Examples are phosphorthioate, phosphordithioate, phosphoramidate and methylphosphonate oligonucleotides.

PNA (having a backbone without phosphate and d-ribose) can also be used as a DNA analog.

The above mentioned modified nucleotides, nucleotide analogs as well as oligonucleotide backbone modifications can be combined as desired in an oligonucleotide in the sense of the present disclosure.

The linker L consisting of a-S-b has a length of 6 to 100 nm. In some embodiments the linker L consisting of a-S-b has a length of 6 to 80 nm. Also, in some cases the linker has a length of 6 to 50 nm or of 6 to 40 nm. In some embodiments the linker will have a length of 10 nm or longer or of 15 nm in length or longer. In some embodiments the linker has between 10 nm and 50 nm in length. In some embodiments a and b, respectively, are binding pair members and have a length of at least 2.5 nm each.

The length of non-nucleosidic entities of a given linker (a-S-b) in theory and by complex methods can be calculated by using known bond distances and bond angles of compounds which are chemically similar to the non-nucleosidic entities. Such bond distances are summarized for some molecules in standard text books: CRC Handbook of Chemistry and Physics, 91st edition, 2010-2011, section 9. However, exact bond distances vary for each compound. There is also variability in the bond angles.

It is therefore more practical to use an average parameter (an easy to understand approximation) in such calculation.

In the calculation of a spacer or a linker length the following approximations apply: a) for calculating lengths of nonnucleosidic entities an average bond length of 130 pm with an bond angle of 180° independently of the nature of the linked atoms is used; b) one nucleotide in a single strand is calculated with 500 pm and c) one nucleotide in a double strand is calculated with 330 pm.

The value of 130 pm is based on calculation of the distance of the two terminal carbonatoms of a C(sp3)-C(sp3)-C(sp3) chain with a bond angle of 109°28' and a distance of 153 pm between two C(sp3) which is approx 250 pm which translates with an assumed bond angle of 180° to and bond distance between two C(Sp3) with 125 pm. Taking in account that heteroatoms like P and S and sp2 and sp1 C atoms could also be part of the spacer the value 130 pm is taken. If a spacer comprises a cyclic structure like cycloalkyl or aryl the distance is calculated in analogous manner, by counting the number of the bonds of said cyclic structure which are part of the overall chain of atoms that are defining the distance.

The spacer S can be construed as required to e.g. provide for the desired length as well as for other desired properties. The spacer can e.g. be fully or partially composed of naturally occurring or non-naturally occurring amino acids, of phosphate-sugar units e.g. a DNA like backbone without nucleobases, of glyco-peptidic structures, or at least partially of saccharide units or at least partially of polymerizable subunits like glycols or acryl amide.

The length of spacer S in a binding agent according to the present disclosure may be varied as desired. In order to easily make available spacers of variable length, a library, some embodiments may have a simple synthetic access to the spacers of such library. A combinatorial solid phase synthesis of a spacer may be present in some embodiments. Since spacers have to synthesized up to a length of about 100 nm, the synthesis strategy is chosen in such a manner that the monomeric synthetic building blocks are assembled during solid phase synthesis with high efficiency. The synthesis of deoxy oligonucleotides based on the assembly of phosphoramidite as monomeric building blocks perfectly meet this requirements. In such spacer monomeric units within a spacer are linked in each case via a phosphate or phosphate analog moiety.

The spacer S can contain free positively or/and negatively charged groups of polyfunctional amino-carboxylic acids, e.g. amino, carboxylate or phosphate. For example the charge carriers can be derived from trifunctional aminocarboxylic acids which contain a) an amino group and two carboxylate groups or b) two amino groups and one carboxylate group. Examples of such trifunctional aminocarboxylic acids are lysine, ornithine, hydroxylysine, $\alpha,\beta$-diamino propionic acid, arginine, aspartic acid and glutamic acid, carboxy glutamic acid and symmetric trifunctional carboxylic acids like those described in EP-A-0 618 192 or U.S. Pat. No. 5,519,142. Alternatively one of the carboxylate groups in the trifunctional aminocarboxylic acids a) can be replaced by a phosphate, sulphonate or sulphate group. An example of such a trifunctional amino acid is phosphoserine.

The spacer S can also contain uncharged hydrophilic groups. Examples of uncharged hydrophilic groups include ethylene oxide or polyethylene oxide groups, for example, with at least three ethylene oxide units, sulphoxide, sulphone, carboxylic acid amide, carboxylic acid ester, phosphonic acid amide, phosphonic acid ester, phosphoric acid amide, phosphoric acid ester, sulphonic acid amide, sulphonic acid ester, sulphuric acid amide and sulphuric acid ester groups. The amide groups may be primary amide groups, for example carboxylic acid amide residues in amino acid side groups e.g. the amino acids asparagine and glutamine. The esters may also be derived from hydrophilic alcohols, in particular C1-C3 alcohols or diols or triols.

In one embodiment the spacer S is composed of one type of monomer. For example, the spacer is composed exclusively of amino acids, of sugar residues, of diols, of phospho-sugar units or it can be a nucleic acid, respectively.

In one embodiment, the spacer is DNA. In an exemplary embodiment the spacer is the L-stereoisomer of DNA also known as beta-L-DNA,L-DNA or mirror image DNA. L-DNA features advantages like orthogonal hybridization behaviour, which means that a duplex is formed only between two complementary single strands of L-DNA but no duplex is formed between a single strand of L-DNA and the complementary DNA strand, nuclease resistance and ease of synthesis even of a long spacer. As pointed out ease of synthesis and variability in spacer length are important for a spacer library. Spacers of variable length are extremely utile in identifying the binding agent according to the present disclosure having a spacer of optimal length thus providing for the optimal distance between the two monovalent binders.

Spacer building blocks, as the name says, can be used to introduce a spacing moiety into the spacer S or to build the spacer S of the linker a-S-b.

Different numbers and kinds of non-nucleotidic as well nucleotidic spacer building blocks are at hand for introducing spacing moieties.

Many different non nucleotidic bifunctional spacer building blocks are known in literature and a great variety is commercially available. The choice of the non nucleotidic bifunctional spacer building is influencing the charge and flexibility of the spacer molecule.

In bifunctional spacer building blocks a hydroxyl group which is protected with an acid labile protecting group is connected to a phosphoramidite group.

Bifunctional spacer building blocks in one embodiment are non-nucleosidic compounds. For example, such spacers are C2-C18 alkyl, alkenyl, alkinyl carbon chains, whereas said alkyl, alkenyl, alkinyl chains may be interrupted by additional ethyleneoxy and/or amide moieties or quarternized cationic amine moieties in order to increase hydrophilicity of the linker. Cyclic moieties like C5-C6-cycloalkyl, C4N, C5N, C4O,C5O-heterocycloalkyl, phenyl which are optionally substituted with one or two C1-C6 alkyl groups can also be used as nonnucleosidic bifunctional spacer moieties. Exemplary bifunctional building blocks comprise C3-C6 alkyl moieties and tri- to hexa-ethyleneglycol chains. Table I shows some examples of nucleotidic bifunctional spacer building blocks with different hydrophilicity, different rigidity and different charges. One oxygen atom is connected to an acid labile protecting group such as dimethoxytrityl and the other is part of a phosphoramidite.

TABLE I

Examples of non-nucleotidic bifunctional spacer building blocks

| Non-nucleotidic bifunctional spacer building blocks | Reference |
|---|---|
| | Seela, F., Nucleic Acids Research 15 (1987) 3113-3129 |
| | Iyer, R. P., Nucleic Acids Research 18 (1990) 2855-2859 |
| | WO 89/02931 A1 |
| | EP 1 538 221 |
| | US 2004/224372 |

TABLE 1-continued

Examples of non-nucleotidic bifunctional spacer building blocks

| Non-nucleotidic bifunctional spacer building blocks | Reference |
|---|---|
| (structure shown) | WO 2007/069092 |

A simple way to build the spacer S or to introduce spacing moieties into the spacer S is to use standard D or L nucleoside phosphoramidite building blocks. In one embodiment a single strand stretch of dT is used. This is advantageous, because dT does not carry a base protecting group.

Hybridization can be used in order to vary the spacer length (distance between the binding pair members a and b) and the flexibility of the spacer, because the double strand length is reduced compared to the single strand and the double strand is more rigid than a single strand.

For hybridization in one embodiment oligonucleotides modified with a functional moiety X are used. The oligonucleotide used for hybridization can have one or two terminal extensions not hybridizing with the spacer and/or is branched internally.

Such terminal extensions that are not hybridizing with the spacer (and not interfering with the binding pairs a:a' and b:b') can be used for further hybridization events. In one embodiment an oligonucleotide hybridizing with a terminal extension is a labeled oligonucleotide. This labeled oligonucleotide again may comprise terminal extensions or being branched in order to allow for further hybridization, thereby a polynucleotide aggregate or dendrimer can be obtained. A poly-oligonucleic acid dendrimer may be used in order to produce a polylabel. or in order to get a high local concentration of X.

In one embodiment the spacer S has a backbone length of 1 to 100 nm. With other words here the groups a and b of Formula I are between 1 and 100 nm apart. In one embodiment a and b, respectively, each are a binding pair member and the spacer S has a backbone length of 1 to 95 nm.

"a':a" as well as "b:b'" each independently represent a binding pair. In one embodiment each of the binding pair members a and b, respectively, has a length of at least 2.5 nm.

a and a' are the members of the binding pair a':a and b and b' are the members of the binding pair b:b', respectively. Each member of a binding pair may be of a molecular weight of 10 kD or below, for example. In further embodiments the molecular weight of each binder of such binding pair is 8, 7, 6, 5 or 4 kD or below.

The binding affinity for (within) a binding pair, a:a' or b':b, respectively, is at least $10^8$ l/mol. Both binding pairs are different. For a binding pair difference is e.g. acknowledged if the affinity for the reciprocal binding, e.g. binding of a as well as a' to b or b' is 10% of the affinity within the pair a:a' or lower. Also, the reciprocal binding, i.e. binding of a as well as a' to b or b', respectively, may be 5% of the affinity within the pair a:a' or lower, or if it is 2% of the affinity within the pair a:a' or lower. In one embodiment the difference is so pronounced that the reciprocal (cross-reactive) binding is 1% or less as compared to the specific binding affinity within a binding pair.

In one embodiment a':a and b:b' are binding pairs and the members of the binding pairs a':a and b:b' are selected from the group consisting of leucine zipper domain dimers and hybridizing nucleic acid sequences. In one embodiment both binding pairs represent leucine zipper domain dimers. In one embodiment both binding pairs are hybridizing nucleic acid sequences.

The term "leucine zipper domain" is used to denote a commonly recognized dimerization domain characterized by the presence of a leucine residue at every seventh residue in a stretch of approximately 35 residues. Leucine zipper domains are peptides that promote oligomerization of the proteins in which they are found. Leucine zippers were originally identified in several DNA-binding proteins (Landschulz, H. W. et al., Science 240 (1988) 1759-1764), and have since been found in a variety of different proteins. Among the known leucine zippers are naturally occurring peptides and derivatives thereof that dimerize or trimerize. Examples of leucine zipper domains suitable for producing soluble multimeric proteins are described in PCT application WO 94/10308, and the leucine zipper derived from lung surfactant protein D (SPD) described in Hoppe, H. J. et al., FEBS Lett. 344 (1994) 191-195.

Leucine zipper domains form dimers (binding pairs) held together by an alpha-helical coiled coil. A coiled coil has 3.5 residues per turn, which means that every seventh residue occupies an equivalent position with respect to the helix axis. The regular array of leucines inside the coiled coil stabilizes the structure by hydrophobic and Van der Waals interactions.

If leucine zipper domains form the first binding pair (a':a) and the second binding pair (b:b'), both leucine zipper sequences are different, i.e. sequences a and a' do not bind to b and b'. Leucine zipper domains may be isolated from natural proteins known to contain such domains, such as transcription factors. One leucine zipper domain may e.g. come from the transcription factor fos and a second one from the transcription factor jun. Leucine zipper domains may also be designed and synthesized artificially, using standard techniques for synthesis and design known in the art.

In an exemplary embodiment both members of the binding pairs a':a and b:b', i.e. a, a', b and b' represent leucine zipper domains and the spacer S consists of amino acids. In this embodiment production of the construct a-S-b is easily possible. Varying the length of such spacer S as desired is straightforward for a person skilled in the art. Such polypeptide can be synthesized or recombinantly produced.

E.g., recombinant fusion proteins comprising a spacer polypeptide fused to a leucine zipper peptide at the N-terminus and to a leucine zipper peptide at the C-terminus can be expressed in suitable host cells according to standard techniques. A DNA sequence coding for a desired peptide spacer can be inserted between a sequence coding for a member of a first leucine zipper domain a and in the same reading frame a DNA sequence coding for a member of a second leucine zipper domain b.

The spacer S, if the linker a-S-b is a polypeptide in one embodiment comprises once or several times a GGGGS (SEQ ID NO:13) amino acid sequence motif. The spacer S may also comprise a tag sequence. The tag sequence may be selected from commonly used protein recognition tags such as YPYDVPDYA (HA-Tag) (SEQ ID NO:14) or GLN-DIFEAQKIEWHE (Avi-Tag) (SEQ ID NO:15).

In an exemplary embodiment both binding pairs (a':a) and (b:b') are hybridizing nucleic acid sequences.

As indicated already by nomenclature, a and a' as well as b and b' hybridize to one another, respectively. The nucleic acid sequences comprised in a and a' one the one hand and in b and b' on the other hand are different. With other words the sequences of in the binding pair a':a do not bind to the sequences of the binding pair b:b', respectively, and vice versa. In one embodiment the present disclosure relates to an at least dual binding agent of Formula I, wherein the binding pairs a:a' and b:b', respectively, both are hybridizing nucleic acid sequences and wherein the hybridizing nucleic acid sequences of the different binding pairs a':a and b:b' do not hybridize with one another. With other words a and a' hybridize to each other but do not bind to any of b or b' or interfere with their hybridization and vice versa. Hybridization kinetics and hybridization specificity can easily be monitored by melting point analyses. Specific hybridization of a binding pair (e.g. a:a') and non-interference (e.g. with b or b') is acknowledged, if the melting temperature for the pair a:a' as compared to any possible combination with b or b', respectively, (i.e. a:b; a:b'; a':b and a':b') is at least 20° C. higher.

The nucleic acid sequences forming a binding pair, e.g. (a:a') or any other nucleic acid sequence-based binding pair, may compromise any naturally occurring nucleobase or an analogue thereto and may have a modified or an un-modified backbone as described above, provided it is capable of forming a stable duplex via multiple base pairing. Stable means that the melting temperature of the duplex is higher than 37° C. In some cases, the double strand consists of two fully complementary single strands. However mismatches or insertions are possible as long as the a stability at 37° C. is given.

As the skilled artisan will appreciate a nucleic acid duplex can be further stabilized by interstrand crosslinking. Several appropriate cross-linking methods are known to the skilled artisan, e.g. methods using psoralen or based on thionucleosides.

The nucleic acid sequences representing the members of a binding pair may consist of between 12 and 50 nucleotides. Also, in some embodiments such nucleic acid sequences will consist of between 15 and 35 nucleotides.

RNAses are ubiquitous and special care has to be taken to avoid unwanted digestion of RNA-based binding pairs and/or spacer sequences. While it certainly is possible to use, e.g. RNA-based binding pairs and/or spacers, binding pairs and/or spacers based on DNA represent an exemplary embodiment.

Appropriate hybridizing nucleic acid sequences can easily be designed to provide for more than two pairs of orthogonal complementary oligonucleotides, allowing for an easy generation and use of more than two binding pairs. Another advantage of using hybridizing nucleic acid sequences in a binding agent of the present disclosure is that modifications can be easily introduced into a nucleic acid sequences. Modified building blocks are commercially available which e.g. allow for an easy synthesis of a linker comprising a functional moiety. Such functional moiety can be easily introduced at any desired position and in any of the structures a and a' as well as b and b' and/or S, provided they represent an oligonucleotide.

In some embodiments the spacer S comprised in a binding agent according to Formula I is a nucleic acid. In some embodiments both binding pairs are hybridizing nucleic acid sequences and the spacer S also is a nucleic acid. In this embodiment the linker L consisting of a-S-b is an oligonucleotide.

In case the spacer S as well as the sequences a, a', b and b' all are oligonucleotide sequences it is easily possible to provide for and synthesize a single oligonucleotide representing the linker L comprising S and the members a and b of the binding pairs a':a and b:b', respectively. In case the monovalent binders A and B, respectively, are polypeptides, they can each be coupled easily to the hybridizing nucleic acid sequences a' and b', respectively. The length of the spacer S comprised in such construct can easily be varied in any desired manner. Based on the three constructs a-S-b, A-a' and b'-B the binding agent of Formula I can be most easily obtained according to standard procedures by hybridization between a':a and b:b', respectively. When spacers of different length are used, the resulting constructs, provide for otherwise identical binding agents, yet having a different distance in between the monovalent binders A and B. This allows for optimal distance and/or flexibility.

In some embodiments the spacer S as well as the sequences a, a', b and b' are DNA.

The enantiomeric L-DNA, is known for its orthogonal hybridization behavior, its nuclease resistance and for ease of synthesis of oligonucleotides of variable length. This ease of variability in linker length via designing appropriate spacers is important for optimizing the binding of a binding agent as disclosed herein to its antigen or antigens.

In some embodiments the linker L (=a-S-b) is enantiomeric L-DNA or L-RNA. In an exemplary embodiment linker a-S-b is enantiomeric L-DNA. In an exemplary embodiment a, a', b and b' as well as the spacer S are enantiomeric L-DNA or L-RNA. In an exemplary embodiment a, a', b and b' as well as the spacer S are enantiomeric L-DNA.

In one embodiment the spacer S is an oligonucleotide and is synthesized in two portions comprising ends hybridizable with each other. In this case the spacer S can be simply constructed by hybridization of these hybridizable ends with one another. The resulting spacer construct comprises an oligonucleotide duplex portion. As obvious, in case the spacer is construed that way, the sequence of the hybridizable oligonucleotide entity forming said duplex is chosen in such a manner that no hybridization or interference with the binding pairs a:a' and b:b' can occur.

As already described above the monovalent specific binders A and B of Formula I may be nucleic acids. In one embodiment of the present disclosure a', a, b, b', A, B and s all are oligonucleotide sequences. In this embodiment the sub-units A-a', a-S-b and b'-B of Formula I can easily and independently be synthesized according to standard procedures and combined by hybridization according to convenient standard procedures. The functional moiety X may be selected from the group consisting of a binding group, a labeling group, an effector group and a reactive group.

If more than one functional moiety X is present, each such functional moiety can in each case be independently a binding group, a labeling group, an effector group or a reactive group.

In one embodiment the functional moiety X may be selected from the group consisting of a binding group, a labeling group and an effector group.

In one embodiment the group X is a binding group. As obvious to a person skilled in the art, the binding group X will be selected to have no interference with the pairs a':a and b:b'.

Examples of binding groups are the partners of a bioaffine binding pair which can specifically interact with the other partner of the bioaffine binding pair. Suitable bioaffine binding pairs are hapten or antigen and antibody; biotin or biotin analogues such as aminobiotin, iminobiotin or desthiobiotin and avidin or streptavidin; sugar and lectin, oligonucleotide and complementary oligonucleotide, receptor and ligand, e.g., steroid hormone receptor and steroid hormone. In one embodiment X is a binding group and is covalently bound to at least one of a', a, b, b' or S of the compound of Formula I. According to some embodiments the smaller partner of a bioaffine binding pair, e.g. biotin or an analogue thereto, a receptor ligand, a hapten or an oligonucleotide is covalently bound to at least one of a', a, S, b or b' as defined above.

In one embodiment functional moiety X is a binding group selected from hapten; biotin or biotin analogues such as aminobiotin, iminobiotin or desthiobiotin; oligonucleotide and steroid hormone.

In one embodiment the functional moiety X is a reactive group. The reactive group can be selected from any known reactive group, like Amino, Sulfhydryl, Carboxylate, Hydroxyl, Azido, Alkinyl or Alkenyl. In one embodiment the reactive group is selected from Maleinimido, Succinimidyl, Dithiopyridyl, Nitrophenylester, Hexafluorophenylester.

In one embodiment the functional moiety X is a labeling group. The labeling group can be selected from any known detectable group. The skilled artisan will choose the number of labels as appropriate for best sensitivity with least quenching.

The labeling group can be selected from any known detectable group. In one embodiment the labeling group is selected from dyes like luminescent labeling groups such as chemiluminescent groups e.g. acridinium esters or dioxetanes or fluorescent dyes e.g. fluorescein, coumarin, rhodamine, oxazine, resorufin, cyanine and derivatives thereof, luminescent metal complexes such as ruthenium or europium complexes, enzymes as used for CEDIA (Cloned Enzyme Donor Immunoassay, e.g. EP 0 061 888), microparticles or nanoparticles e.g. latex particles or metal sols, and radioisotopes.

In one embodiment the labeling group is a luminescent metal complex and the compound has a structure of the general formula (II):

$$[M(L_1L_2L_3)]_n\text{-}Y\text{—}X_mA \quad (II)$$

in which M is a divalent or trivalent metal cation selected from rare earth or transition metal ions, $L_1$, $L_2$ and $L_3$ are the same or different and denote ligands with at least two nitrogen-containing heterocycles in which $L_1$, $L_2$ and $L_3$ are bound to the metal cation via nitrogen atoms, X is a reactive functional group which is covalently bound to at least one of the ligands $L_1$, $L_2$ and $L_3$ via a linker Y, n is an integer from 1 to 10, and in some illustrative embodiments is 1 to 4, m is 1 or 2 and in some illustrative embodiments is 1 and A denotes the counter ion which may be required to equalize the charge.

The metal complex may be a luminescent metal complex i.e. a metal complex which undergoes a detectable luminescence reaction after appropriate excitation. The luminescence reaction can for example be detected by fluorescence or by electrochemiluminescence measurement. The metal cation in this complex is for example a transition metal or a rare earth metal. The metal may be ruthenium, osmium, rhenium, iridium, rhodium, platinum, indium, palladium, molybdenum, technetium, copper, chromium or tungsten. In some illustrative embodiments ruthenium is used.

The ligands $L_1$, $L_2$ and $L_3$ are ligands with at least two nitrogen-containing heterocycles. Aromatic heterocycles such as bipyridyl, bipyrazyl, terpyridyl and phenanthrolyl may be used. The ligands $L_1$, $L_2$ and $L_3$ may be selected from bipyridine and phenanthroline ring systems.

The complex can additionally contain one or several counter ions A to equalize the charge. Examples of suitable negatively charged counter ions are halogenides, $OH^-$, carbonate, alkylcarboxylate, e.g. trifluoroacetate, sulphate, hexafluorophosphate and tetrafluoroborate groups. Hexafluorophosphate, trifluoroacetate and tetrafluoroborate groups are used in some illustrative embodiments. Examples of suitable positively charged counter ions are monovalent cations such as alkaline metal and ammonium ions.

In further embodiments the functional moiety X is an effector group. An exemplary effector group is a therapeutically active substance.

Therapeutically active substances have different ways in which they are effective, e.g. in inhibiting cancer. They can damage the DNA template by alkylation, by cross-linking, or by double-strand cleavage of DNA. Other therapeutically active substances can block RNA synthesis by intercalation. Some agents are spindle poisons, such as vinca alkaloids, or anti-metabolites that inhibit enzyme activity, or hormonal and anti-hormonal agents. The effector group X may be selected from alkylating agents, antimetabolites, antitumor antibiotics, vinca alkaloids, epipodophyllotoxins, nitrosoureas, hormonal and antihormonal agents, and toxins.

Currently exemplary alkylating agents include cyclophosphamide, chlorambucil, busulfan, Melphalan, Thiotepa, ifosphamide, Nitrogen mustard.

Currently exemplary antimetabolites include methotrexate, 5-Fluorouracil, cytosine arabinoside, 6-thioguanine, 6-mercaptopurin.

Currently exemplary antitumor antibiotics include doxorubicin, daunorubicin, idorubicin, nimitoxantron, dactinomycin, bleomycin, mitomycin, and plicamycin.

Currently exemplary spindle poisons include maytansine and maytansinoids, vinca alkaloids and epipodophyllotoxins include vincristin, vinblastin, vindestin, Etoposide, Teniposide.

Currently exemplary nitrosoureas include carmustin, lomustin, semustin, streptozocin.

Currently exemplary hormonal and antihormonal agents include adrenocorticorticoids, estrogens, antiestrogens, progestins, aromatase inhibitors, androgens, antiandrogens.

Additional exemplary random synthetic agents include dacarbazin, hexamethylmelamine, hydroxyurea, mitotane, procarbazide, cisplastin, carboplatin.

The functional moiety X is bound either covalently or via an additional binding pair to at least one of (a'), (a), (b), (b') or S. The functional moiety X can occur once or several (n) times. (n) is an integer and 1 or more than one. In some embodiments (n) is between 1 and 100. Also, (n) may be 1-50. In certain embodiments n is 1 to 10, or 1 to 5. In further embodiments n is 1 or 2.

For covalent binding of the functional moiety X to at least one of a', a, b, b' or S any appropriate coupling chemistry can be used. The skilled artisan can easily select such coupling chemistry from standard protocols. It is also possible to incorporate a functional moiety by use of appropriate building blocks when synthesizing a', a, b, b' or S.

In an exemplary embodiment functional moiety X is bound to a, b, or S of the binding agent as defined by Formula I. In an exemplary embodiment functional moiety X is bound to the spacer S of the binding agent as defined by Formula I.

In some embodiments functional moiety X is covalently bound to a, b, or S of the binding agent as defined by Formula I.

If a functional moiety X is located within the a hybridizing oligonucleotide representing a, a', b or b', respectively, in some cases such functional moiety is bound to a modified nucleotide or is attached to the internucleosidic P atom (WO 2007/059816). Modified nucleotides which do not interfere with the hybridization of oligonucleotides are incorporated into those oligonucleotides. Such modified nucleotides may be C5 substituted pyrimidines or C7 substituted 7deaza purines.

Oligonucleotides can be modified internally or at the 5' or 3' terminus with non-nucleotidic entities which are used for the introduction of functional moiety. In some embodiments such non-nucleotidic entities are located within the spacer S, i.e. between the two binding pair members a and b.

Many different non-nucleotidic modifier building blocks for construction of a spacer are known in literature and a great variety is commercially available. For the introduction of a functional moiety either non-nucleosidic bifunctional modifier building blocks or non-nucleosidic trifunctional modified building blocks are either used as CPG for terminal labeling or as phosphroamidite for internal labeling (see: Wojczewski, C. et al., Synlett 10 (1999) 1667-1678).

tional modified building blocks. In some cases modified bifunctional building blocks comprise C3-C6 alkyl moieties and tri- to hexa-ethyleneglycol chains. Non-limiting examples of bifunctional modifier building blocks are given in Table II below.

TABLE II

| Bifunctional non-nucleosidic modifier building block | Introduction of | Reference |
|---|---|---|
| [structure] | [structure] label | Pon, R. T., Tetrahedron Letters 32 (1991) 1715-1718 |
| | [structure with F atoms] | Theisen, P. et al., Nucleic Acids Symposium Series (1992), 27 (Nineteenth Symposium on Nucleic Acids Chemistry) 99-100 EP 0 292 128 |
| [structure] | [structure] | EP 0 523 978 |
| [structure] | [structure] | Meyer, A. et al., Journal of Organic Chemistry 75 (2010) 3927-3930 |
| [structure] | [structure] label | Morocho, A. M. et al., Nucleosides, Nucleotides & Nucleic Acids 22 (2003) 1439-1441 |
| [structure] | [structure] label | Cocuzza, A. J., Tetrahedron Letters 30 (1989) 6287-6290 |

Bifunctional Modifier Building Blocks

Bifunctional modifier building blocks connect a functional moiety or a—if necessary—a protected functional moiety to a phosphoramidite group for attaching the building block at the 5' end (regular synthesis) or at the 3'end (inverted synthesis) to the terminal hydroxyl group of a growing oligonucleotide chain.

Bifunctional modifier building blocks are, for example, non-nucleosidic compounds. For example, such modified building blocks are C2-C18 alkyl, alkenyl, alkynyl carbon chains, whereas said alkyl, alkenyl, alkynyl chains may be interrupted by additional ethyleneoxy and/or amide moieties in order to increase hydrophilicity of the spacer and thereby of the whole linker structure. Cyclic moieties like C5-C6-cycloalkyl, C4N, C5N, C4O,C5O-heterocycloalkyl, phenyl which are optionally substituted with one or two C1-C6 alkyl groups can also be used as non-nucleosidic bifunc- Trifunctional Modifier Building Blocks Trifunctional building blocks connect (i) a functional moiety or a—if necessary—a protected functional moiety, (ii) a phosphoramidite group for coupling the reporter or the functional moiety or a—if necessary—a protected functional moiety, during the oligonucleotide synthesis to a hydroxyl group of the growing oligonucleotide chain and (iii) a hydroxyl group which is protected with an acid labile protecting group, for example, with a dimethoxytrityl protecting group. After removal of this acid labile protecting group a hydroxyl group is liberated which can react with further phosphoramidites. Therefore trifunctional building blocks allow for positioning of a functional moiety to any location within an oligonucleotide. Trifunctional building blocks are also a prerequisite for synthesis using solid supports, e.g. controlled pore glass (CPG), which are used for 3' terminal labeling of oligonucleotides. In this case, the trifunctional building block is connected to a functional moiety or a—if necessary—a protected functional moiety via an C2-C18 alkyl, alkenyl, alkinyl carbon chains, whereas said alkyl, alkenyl, alkyinyl chains may be interrupted by additional ethyleneoxy and/or amide moieties in order to increase hydrophilicity of the spacer and thereby of the whole linker structure and comprises a hydroxyl group which is attached via a cleavable spacer to a solid phase and a hydroxyl group which is protected with an acid labile protecting group. After removal of this protecting group a hydroxyl group is liberated which could then react with a phosphoramidite.

Trifunctional Building Blocks May be Non-Nucleosidic or Nucleosidic.

Non-nucleosidic trifunctional building blocks are C2-C18 alkyl, alkenyl, alkynyl carbon chains, whereas said alkyl, alkenyl, alkynyl are optionally interrupted by additional ethyleneoxy and/or amide moieties in order to increase hydrophilicity of the spacer and thereby of the whole linker structure. Other trifunctional building blocks are cyclic groups like C5-C6-cycloalkyl, C4N, C5N, C4O, C5O heterocycloalkyl, phenyl which are optionally substituted with one ore two C1-C6 alkyl groups. Cyclic and acyclic groups may be substituted with one —(C1-C18)alkyl-O-PG group, whereas said C1-C18 alkyl comprises (Ethyleneoxy)n, (Amide)m moieties with n and m independently from each other=0-6 and PG is an acid labile protecting group. Exemplary trifunctional building blocks are C3-C6 alkyl, cycloalkyl, C5O heterocycloalkyl moieties optionally comprising one amide bond and substituted with a C1-C6 alkyl O-PG group, wherein PG is an acid labile protecting group, such as monomethoxytrityl, dimethoxytrityl, pixyl, and xanthyl.

Non-limiting examples for non-nucleosidic trifunctional building blocks are e.g. summarized in Table III.

TABLE III

Examples for non-nucleosidic trifunctional modifier building Blocks

| Trifunctional | Introduction of | Reference |
|---|---|---|
| 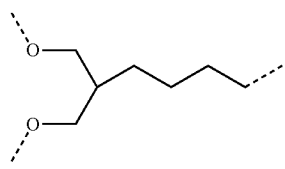 | 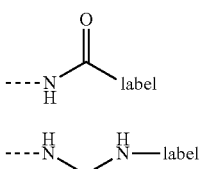 | Nelson, P. S. et al., Nucleic Acids Research 20 (1992) 6253-6259 EP 0 313 219 U. S. Pat. No. 5,585, 481 U.S. Pat No. 5,451,463 EP 0 786 468 WO 92/11388 WO 89/02439 |
| 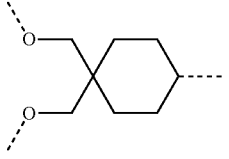 | 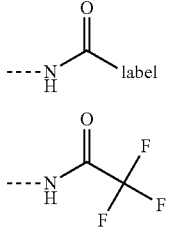 | Su, S. -H, et al., Bioorganic & Medicinal Chemistry Letters 7 (1997) 1639-1644 WO 97/43451 |
| 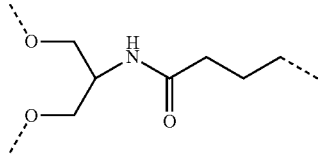 | 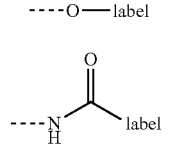 | Putnam, W. C. et al., Nucleosides, Nucleotides & Nucleic Acids 24 (2005) 1309-1323 US 2005/214833 EP 1 186 613 |
| 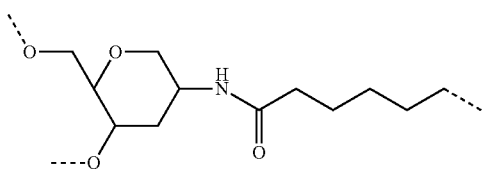 | 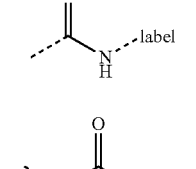 | EP 1 431 298 |

TABLE III-continued

Examples for non-nucleosidic trifunctional modifier building Blocks

| Trifunctional | Introduction of | Reference |
|---|---|---|
| | | WO 94/04550 Vu, H., et al., Nucleic Acids Symposium Series (1993), 29 (Second International Symposium on Nucleic Acids Chemistry), 19-20 |
| | | WO 2003/019145 |
| | | Behrens, C. and Dahl, O., Nucleosides & Nucleotides 18 (1999) 291-305 WO 97/05156 |
| | | Prokhorenko, I. A. et al., Bioorganic & Medicinal Chemistry Letters 5 (1995) 2081-2084 WO 2003/104249 |
| | | U.S. Pat. No. 5,849,879 |

Nucleosidic Modifier Building Blocks:

Nucleosidic modifier building blocks are used for internal labeling whenever it is necessary not to influence the oligonucleotide hybridization properties compared to a non-modified oligonucleotide. Therefore nucleosidic building blocks comprise a base or a base analog which is still capable of hybridizing with a complementary base. The general formula of a labeling compound for labeling a nucleic acid sequence of one or more of a, a', b, b' or S comprised in a binding agent according to Formula I of the present disclosure is given in Formula II.

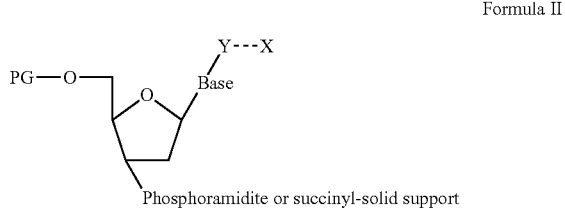

Formula II

Phosphoramidite or succinyl-solid support wherein PG is an acid labile protecting group such as monomethoxytrityl, dimethoxytrityl, pixyl, and xanthyl, wherein Y is C2-C18 alkyl, alkenyl alkinyl, wherein said alkyl, alkenyl, alkinyl may comprise ethyleneoxy and/or amide moieties, wherein Y is C4-C18 alkyl, alkenyl or alkinyl and contains one amide moiety and wherein X is a functional moiety.

Specific positions of the base may be chosen for such substitution to minimize the influence on hybridization properties. Therefore the following positions may be used for substitution: a) with natural bases: Uracil substituted at C5; Cytosine substituted at C5 or at N4; Adenine substituted at C8 or at N6 and Guanine substituted at C8 or at N2 and b) with base analogs: 7 deaza A and 7 deaza G substituted at C7; 7 deaza 8 Aza A and 7 deaza 8 Aza G substituted at C7; 7 deaza Aza 2 amino A substituted at C7; Pseudouridine substituted at N1 and Formycin substituted at N2.

Non-limiting examples for nucleosidic trifunctional building blocks are given in Table IV.

TABLE IV

| Trifunctional nucleosidic | A | Reference |
| --- | --- | --- |
| | | Roget, A. et al., Nucleic Acids Research 17 (1989) 7643-7651<br>WO 89/12642<br>WO 90708156<br>WO 93705060 |
| | | Silva, J. A. et al., Biotecnologia Aplicada 15 (1998) 154-158 |
| | | U. S. Pat. No. 6,531,581<br>EP 0 423 839 |
| | | U. S. Pat. No. 4,948,882<br>U.S. Pat. No. 5,541,313<br>U.S. Pat. No. 5,817,786 |

TABLE IV-continued

| Trifunctional nucleosidic | A | Reference |
|---|---|---|
| 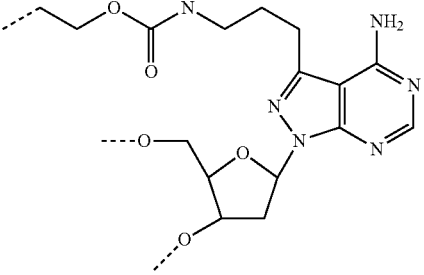 |  | WO 2001/042505 |
| 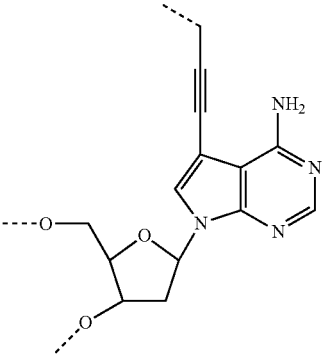 | 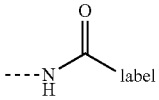 | McKeen, C. M. et al., Organic & Biomolecular Chemistry 1 (2003), 2267-2275 |
| 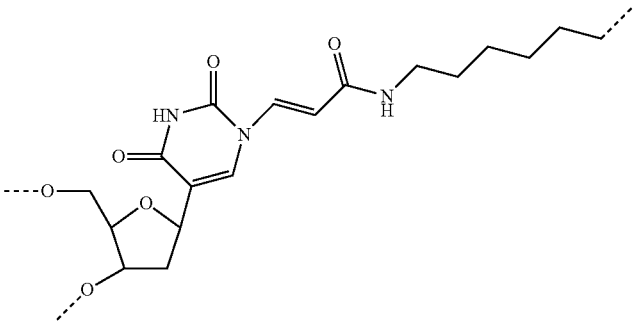 | 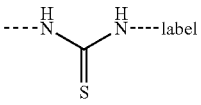 | Ramzaeva, N. et al., Helvetica Chimica Acta 83 (2000) 1108-1126 |

In Tables II, III and IV, one of the terminal oxygen atom of a bifunctional moiety or one of the terminal oxygen atoms of a trifunctional moiety is part of a phosphoramidite that is not shown in full detail but obvious to the skilled artisan. The second terminal oxygen atom of trifunctional building block is protected with an acid labile protecting group PG, as defined for Formula II above.

Post-synthetic modification is another strategy for introducing a covalently bound functional moiety into a linker or a spacer molecule. In this approach an amino group is introduced by using bifunctional or trifunctional building block during solid phase synthesis. After cleavage from the support and purification of the amino modified oligonucleotide is reacted with an activated ester of a functional moiety or with a bifunctional reagent wherein one functional group is an active ester. Exemplary active esters are NHS ester or pentafluor phenyl esters.

Post-synthetic modification is especially useful for introducing a functional moiety which is not stable during solid phase synthesis and deprotection. Examples are modification with triphenylphosphincarboxymethyl ester for Staudinger ligation (Wang, C. C. et al., Bioconjugate Chemistry 14 (2003) 697-701), modification with digoxigenin or for introducing a maleinimido group using commercial available sulfo SMCC.

The functional moiety X in one embodiment is bound to at least one of a', a, b, b' or S via an additional binding pair.

The additional binding pair to which a functional moiety X can be bound may be a leucine zipper domain or a hybridizing nucleic acid. In case the functional moiety X is bound to at least one of a', a, b, b' or S via an additional binding pair member, the binding pair member to which X is bound and the binding pairs a':a and b:b', respectively, all are selected to have different specificity. The binding pairs a:a', b:b' and the binding pair to which X is bound each bind to (e.g. hybridize with) their respective partner without interfering with the binding of any of the other binding pairs.

Covalent Coupling of a Member of a Binding Pair to a Monovalent Binder

Depending on the biochemical nature of the binder different conjugation strategies are at hand.

In case the binder is a naturally occurring protein or a recombinat polypeptide of between 50 to 500 amino acids, there are standard procedures in text books describing the chemistry for synthesis of protein conjugates, which can be easily followed by the skilled artisan. (Hackenberger, C. P. et al., Angew. Chem., Int. Ed., 47 (2008) 10030-10074).

In one embodiment the reaction of a maleinimido moiety with a cystein residue within the protein is used. This is an exemplary coupling chemistry in case e.g. an Fab or Fab'-fragment of an antibody is used a monovalent binder. Alternatively in one embodiment coupling of a member of a binding pair (a' or b', respectively, of Formula I) to the C-terminal end of the binder polypeptide is performed. C-terminal modification of a protein, e.g. of an Fab-fragment can e.g. be performed as described (Sunbul, Murat and Yin, Jun, Organic & Biomolecular Chemistry 7 (2009) 3361-3371).

In general site specific reaction and covalent coupling of a binding pair member to a monovalent polypeptidic binder is based on transforming a natural amino acid into an amino acid with a reactivity which is orthogonal to the reactivity of the other functional groups present in a protein. For example, a specific cystein within a rare sequence context can be enzymatically converted in an aldehyde (see Frese, M.-A. et al., ChemBioChem 10 (2009) 425-427). It is also possible to obtain a desired amino acid modification by utilizing the specific enzymatic reactivity of certain enzymes with a natural amino acid in a given sequence context (see e.g.: Taki, M. et al., Protein Engineering, Design & Selection 17 (2004) 119-126; Gautier, A. et al., Chemistry & Biology 15 (2008) 128-136; Protease-catalyzed formation of C—N bonds is used by Bordusa, F., Highlights in Bioorganic Chemistry (2004) 389-403 and Sortase-mediated protein ligation is used by Mao, H. et al., in J. Am Chem Soc. 126 (2004) 2670-2671 and reviewed by Proft, T., in Biotechnol. Lett 32 (2010) 1-10).

Site specific reaction and covalent coupling of a binding pair member to a monovalent polypeptidic binder can also be achieved by the selective reaction of terminal amino acids with appropriate modifying reagents.

The reactivity of an N-terminal cystein with benzonitrils (Ren, Hongjun, Xiao, et al., Angewandte Chemie, International Edition 48 (2009) 9658-9662) can be used to achieve a site-specific covalent coupling.

Native chemical ligation can also rely on C-terminal cystein residues (Taylor, E. Vogel, Imperiali, B., Nucleic Acids and Molecular Biology 22 (2009) (Protein Engineering) 65-96).

EP 1 074 563 describes a conjugation method which is based on the faster reaction of a cystein within a stretch of negatively charged amino acids with a cystein located in a stretch of positively charged amino acids.

The monovalent binder may also be a synthetic peptide or peptide mimic. In case a polypeptide is chemically synthesized, amino acids with orthogonal chemical reactivity can be incorporated during such synthesis (de Graaf, A. J. et al., Bioconjugate Chemistry 20 (2009) 1281-1295). Since a great variety of orthogonal functional groups is at stake and can be introduced into a synthetic peptide, conjugation of such peptide to a linker is standard chemistry.

In order to obtain a mono-labeled protein the conjugate with 1:1 stoichiometry may be separated by chromatography from other conjugation products. This procedure is facilitated by using a dye labeled binding pair member and a charged spacer. By using this kind of labeled and highly negatively charged binding pair member, mono conjugated proteins are easily separated from non labeled protein and proteins which carry more than one linker, since the difference in charge and molecular weight can be used for separation. The fluorescent dye is valuable for purifying the binding agent from un-bound components, like a labeled monovalent binder.

Therefore in one embodiment a binding pair member (a' and/or b', respectively of Formula I) which is labeled with a fluorescent dye (e.g. synthesized using a bifunctional or trifunctional modifier building block in combination with bifunctional spacer building blocks during synthesis) for forming the binding agent of the present disclosure may be used. In an exemplary embodiment the spacer S as well as the sequences a, a', b and b' are DNA and at least one of a' or b', respectively, is labeled with a fluorescent dye. In some embodiments the spacer S as well as the sequences a, a', b and b' are DNA and both a' and b', respectively, are labeled each with a different fluorescent dye.

In one embodiment the present disclosure relates to a bispecific binding agent of the Formula I: A-a':a-S-b:b'-B:X(n); wherein A as well as B is a monovalent specific binder, wherein a':a as well as b:b' represent a binding pair with a':a and b:b' having a different specificity, wherein S represents a spacer, wherein (: X) denotes a functional moiety bound via a further binding pair to at least one of a', a, b, b' or S, wherein (n) is an integer and at least 1, wherein — represents a covalent bond, and wherein the linker a-S-b has a length of 6 to 100 nm.

In some embodiments the binding pairs a':a and b:b' are hybridizing nucleic acid sequences, the spacer S is a nucleic acid and the further binding pair to which the functional moiety X is bound is also a nucleic acid. In such embodiments the spacer S may be construed to comprise, in addition to the two specifically hybridizing sequences a and a' and b and b', respectively, one or more further sequences also capable of hybridizing to its or their complementary sequences. In this embodiment a functional moiety X is bound to the spacer S via a further binding pair also consisting of hybridizing nucleic acid sequences.

A monovalent binder for use in the construction of a binding agent as disclosed herein has to have a Kdiss from $10^{-2}$/sec to $10^{-5}$/sec. Also, a monovalent binder for use in the construction of a binding agent as disclosed herein has to have a Kdiss from $10^{-3}$/sec to $10^{-5}$/sec.

According to some embodiments, in the binding agent according to Formula I, each of the monovalent binders A and B, respectively has a Kdiss from $10^{-2}$/sec to $10^{-5}$/sec and in some illustrative embodiments from $10^{-3}$/sec to $10^{-5}$/sec.

In some embodiments, the binding agent according to Formula I has a Kdiss of $10^{-5}$/sec or better, or may have a Kdiss of $10^{-6}$/sec or better. In some embodiments the binding agent according to Formula I may have a Kdiss of $10^{-7}$/sec or better.

As the skilled artisan will appreciate the Kdiss is a temperature-dependent value. Logically, the Kdiss-values of a binding agent according to the present disclosure are determined at the same temperature. As will be appreciated, a Kdiss-value is determined at the same temperature at which the binding agent shall be used, e.g., an assay shall be performed. In one embodiment the Kdiss-values are established at room temperature, i.e. at 20° C., 21° C., 22° C., 23° C., 24° C. or 25° C., respectively. In one embodiment the Kdiss-values are established at 4 or 8° C., respectively. In one embodiment the Kdiss-values are established at 25° C. In one embodiment the Kdiss-values are established at 37° C.

As mentioned already above, it is now possible and pretty straightforward to produce a binding agent as defined in Formula I. A full library of a binding agent according to Formula I can be easily provided, analyzed and the most powerful binding agent out of such library produced at large scale, as required.

The library mentioned above refers to a full set of binding agents according to Formula I, wherein each A, a, a', b, b' and B are identical and wherein in the length of the spacer S is adjusted to best meet the requirements set out for the binding agent. It is easily possible to first use a spacer ladder spanning the whole spectrum of 1 to 100 nm and having steps that are about 10 nm apart. The spacer length is then again easily further refined around the most appropriate length identified in the first round.

In one embodiment the present disclosure relates to a method of producing a binding agent of the Formula I: A-a':a-S-b:b'-B:X(n), wherein A as well as B is a monovalent binder, wherein a':a as well as b:b' is a binding pair, wherein a' and a and do not interfere with the binding of b to b' and vice versa, wherein S is a spacer of at least 1 nm in length, wherein (: X) denotes a functional moiety bound either covalently or via a binding pair to at least one of a', a, b, b' or S, wherein (n) is an integer and at least 1, wherein — represents a covalent bond, and wherein the linker a-S-b has a length of 6 to 100 nm, the method comprising the steps of: a) synthesizing A-a' and b'-B, respectively, b) synthesizing the linker a-S-b and c) forming the binding agent of Formula I, wherein the functional moiety X bound to at least one of a', a, b, b' or S is bound in step a), b) or c).

In some embodiments of this method several linker molecules with spacers of various lengths are synthesized and used in the formation of binding agents according to Formula I comprising spacers of variable length and those binding agent(s) are selected having an improvement in the Kdiss of at least 5-fold over the better of the two monovalent binders. Selection of a binding agent with the desired Kdiss in one embodiment is performed by BiaCore-analysis as disclosed in Example 2.8.

The binding agent according to the present disclosure can e.g. be used to strongly bind an analyte in an immunoassay. If e.g. an analyte has at least two non-overlapping epitopes the binding agent of the present disclosure is construed such that the spacer S has the optimal length for synergistic binding of the monovalent binders to these epitopes. This improvement can e.g. be of great utility in a method for detection of an analyte employing such binding agent. In one embodiment the present disclosure therefore relates to the use of a binding agent as disclosed herein above in the detection of an analyte of interest. In certain embodiments the detection method used is an enzyme-linked immunosorbent assay (ELISA), a direct, indirect, competitive or sandwich immuno assay employing any appropriate way of signal detection, e.g. electrochemiluminescense, or the binding agent is used in immunohistochemistry.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

ILLUSTRATIVE EMBODIMENTS

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. A binding agent of the Formula A-a':a-S-b:b'-B:X(n), wherein A as well as B is a monovalent binder, wherein a':a as well as b:b' is a binding pair wherein a' and a do not interfere with the binding of b to b' and vice versa, wherein S is a spacer of at least 1 nm in length, wherein (: X) denotes a functional moiety bound either covalently or via a binding pair to at least one of a', a, b, b' or S, wherein (n) is an integer and at least 1, wherein — represents a covalent bond, and wherein the linker a-S-b has a length of 6 to 100 nm.
2. The binding agent of embodiment 1, wherein the spacer S is 1 to 95 nm in length.
3. The binding agent of embodiments 1 or 2, wherein the binding pairs are selected from the group consisting of leucine zipper domain dimers and hybridizing nucleic acid sequences.
4. The binding agent of any of embodiments 1 to 3, wherein the binding pairs both are hybridizing nucleic acid sequences and wherein the different hybridizing nucleic acid sequences of the binding pairs a':a and b:b' do not hybridize with one another.
5. The binding agent of any of embodiments 1 to 4, wherein the spacer S is a nucleic acid.
6. The binding agent of any of embodiments 1 to 5, wherein the spacer S is a nucleic acid and wherein both binding pairs a':a as well as b:b' also are a nucleic acid.
7. The binding agent of any of embodiments 1 to 6, wherein the spacer S is a nucleic acid and wherein both binding pairs a':a as well as b:b' are nucleic acids and wherein the monovalent binders A and B are nucleic acids.
8. The binding agent of any of embodiments 1 to 7, wherein X is a functional moiety selected from the group consisting of a labeling group, a binding group and an effector group
9. The binding agent of any of embodiments 1 to 8, wherein the functional moiety X is bound to a, b, or S.
10. The binding agent of any of embodiments 1 to 9, wherein the functional moiety X is bound to the spacer S.
11. The binding agent of any embodiments 1 to 10, wherein the functional moiety X is covalently bound to the spacer S.
12. The binding agent of any of embodiments 1 to 10, wherein the functional moiety X is bound to the spacer S via a hybridizing nucleic acid.
13. The binding agent of any of embodiments 1 to 3, or embodiments 8 to 12, wherein the monovalent binders A and B are polypeptides such as Fab-fragments of monoclonal antibodies.
14. Use of a binding agent according to any of embodiments 1 to 13 in the detection of an analyte of interest.
15. Use of a binding agent according to any of embodiments 1 to 13 in an immuno assay.

EXAMPLES

Bi-Valent Binding Agent to Troponin T

1.1 Monoclonal Antibodies and Fab'-Fragments

Two monoclonal antibodies binding to human cardiac Troponin T at different, non-overlapping epitopes, epitope A' and epitope B', respectively, were used. Both these antibodies are used in the current Roche Elecsys™ Troponin T assay, wherein Troponin T is detected in a sandwich immuno assay format.

Purification of the monoclonal antibodies from culture supernatant was carried out using state of the art methods of protein chemistry.

The purified monoclonal antibodies are protease digested with either pre-activated papain (anti-epitope A' MAb) or pepsin (anti-epitope B' MAb) yielding F(ab')2 fragments that are subsequently reduced to Fab'-fragments, i.e. A and B, respectively, in Formula I (A-a':a-S-b:b'-B:$X_n$), with a low concentration of cysteamin at 37° C. The reaction is stopped by separating the cysteamin on a Sephadex G-25 column (GE Healthcare) from the polypeptide-containing part of the sample.

1.2 Conjugation of Fab'-Fragments to ssDNA-Oligonucleotides

The Fab'-fragments are conjugated with the below described activated ssDNAa and ssDNAb oligonucleotides.

Preparation of the Fab'-Fragment-ssDNA Conjugates A" and B", Respectively:

a) Fab'-Anti-Troponin T<Epitope A'>-ssDNA-Conjugate (=A")

For preparation of the Fab'-anti-Troponin T<epitope A'>-ssDNAa-conjugate A" a derivative of SEQ ID NO:5 is used, i.e. 5'-AGT CTA TTA ATG CTT CTG C(=SEQ ID NO:5)-XXX-Y-Z-3', wherein X=propylene-phosphate introduced via Phosphoramidite C3 (3-(4,4'-Dimethoxytrityloxy)propyl-1-[(2-cyanoethyl)-(N,N-diisopropyl)]-phosphoramidite (Glen Research), wherein Y=3"-Amino-Modifier C6 introduced via 3'-Amino Modifier TFA Amino C-6 lcaa CPG (ChemGenes) and wherein Z=4[N-maleinimidomethyl]cyclohexane-1-carboxy introduced via Sulfosuccinimidyl 4-[N-maleimidomethyl]cyclohexane-1-carboxylate (ThermoFischer).

b) Fab'-Anti-Troponin T<Epitope B'>-ssDNAb-Conjugate (=B")

For the preparation of the Fab'-anti-Troponin T<epitope B'>-ssDNA-conjugate (B") a derivative of SEQ ID NO:6 is used, i.e. 5'-Y-Z-XXX-AGT TCT ATC GTC GTC CA-3', wherein X=propylene-phosphate introduced via Phosphoramidite C3 (3-(4,4'-Dimethoxytrityloxy)propyl-1-[(2-cyanoethyl)-(N,N-diisopropyl)]-phosphoramidite (Glen Research), wherein Y=5'-Amino-Modifier C6 introduced via (6-(4-Monomethoxytritylamino)hexyl-(2-cyanoethyl)-(N,N-diisopropyl)-phosphoramidite (Glen Research), and wherein Z=4[N-maleinimidomethyl]cyclohexane-1-carboxy introduced via Sulfosuccinimidyl 4-[N-maleimidomethyl]cyclohexane-1-carboxylate (ThermoFischer).

The oligonucleotides of SEQ ID NO:5 or 6, respectively, have been synthesized by state of the art oligonucleotide synthesis methods. The introduction of the maleinimido group was done via reaction of the amino group of Y with the succinimidyl group of Z which was incorporated during the solid phase oligonucleotide synthesis process.

The single-stranded DNA constructs shown above bear a thiol-reactive maleimido group that reacts with a cysteine of the Fab' hinge region generated by the cysteamine treatment. In order to obtain a high percentage of single-labeled Fab'-fragments the relative molar ratio of ssDNA to Fab'-fragment is kept low. Purification of single-labeled Fab'-fragments (ssDNA:Fab'=1:1) occurs via anion exchange chromatography (column: MonoQ, GE Healthcare). Verification of efficient labeling and purification is achieved by analytical gel filtration chromatography and SDS-PAGE.

1.3 Biotinylated Linker Molecules

The oligonucleotides used in the ssDNA linkers L1, L2 and L3, respectively, have been synthesized by state of the art oligonucleotide synthesis methods and employing a biotinylated phosphoramidite reagent for biotinylation.

Linker 1 (=L1), a biotinylated ssDNA linker 1 with no spacer except biotinylated thymidine has the following composition: 5'-GCA GAA GCA TTA ATA GAC T (Biotin-dT)-TGG ACG ACG ATA GAA CT-3'. It comprises ssDNA oligonucleotides of SEQ ID NO:7 and 8, respectively, and was biotinylated by using Biotin-dT (=T-Bi) (5'-Dimethoxytrityloxy-5-[N-((4-t-butylbenzoyl)-biotinyl)-aminohexyl)-3-acrylimido]-2'-deoxyUridine-3'-[(2-cyanoethyl)-(N,N-diisopropyl)]-phosphoramidite (Glen Research) in the middle of the spacer.

Linker 2 (=L2), a biotinylated ssDNA linker 2 with a 11 mer spacer has the following composition: 5'-GCA GAA GCA TTA ATA GAC T T5-(Biotin-dT)-T5 TGG ACG ACG ATA GAA CT-3'. It comprises ssDNA oligonucleotides of SEQ ID NO:7 and 8, respectively, twice oligonucleotide stretches of five thymidines each and was biotinylated by using Biotin-dT (5'-Dimethoxytrityloxy-5-[N-((4-t-butylbenzoyl)-biotinyl)-aminohexyl)-3-acrylimido]-2'-deoxyUridine-3'-[(2-cyanoethyl)-(N,N-diisopropyl)]-phosphoramidite (Glen Research) in the middle of the spacer.

Linker 3 (=L3), a biotinylated ssDNA linker 3 with a 31 mer spacer has the following composition: 5'-GCA GAA GCA TTA ATA GAC T T15-(Biotin-dT)-T15 TGG ACG ACG ATA GAA CT-3'. It comprises ssDNA oligonucleotides of SEQ ID NO:7 and 8, respectively, twice oligonucleotide stretches of fifteen thymidines each and was biotinylated by using Biotin-dT (5'-Dimethoxytrityloxy-5-[N-((4-t-butylbenzoyl)-biotinyl)-aminohexyl)-3-acrylimido]-2'-deoxyUridine-3'-[(2-cyanoethyl)-(N,N-diisopropyl)]-phosphoramidite (Glen Research).

1.4 Epitopes for Monovalent Troponin T Binders A and B, Respectively

Synthetic peptides have been construed that individually only have a moderate affinity to the corresponding Fab'-fragment derived from the anti-Troponin T antibodies a and b, respectively.

a) The Epitope A' for Antibody a is Comprised in:
SEQ ID NO:9=ERAEQQRIRAEREKEUUS-LKDRIEKRRRAERAEamide, wherein U represents β-Alanin.

b) The Epitope B' for Antibody b is Comprised in:
SEQ ID NO:10=SLKDRIERRRAERAEOOERAEQQRI-RAEREKEamide, wherein O represents Amino-trioxa-octanoic-acid As the skilled artisan will appreciate it is possible to combine these two epitope-containing peptides in two ways and both variants have been designed and prepared by linear combining the epitopes A' and B'. The sequences of both variants, the linear sequences of epitopes A'-B' (=TnT-1) and B'-A' (=TnT-2), respectively have been prepared by state of the art peptide synthesis methods.

The sequences for epitopes A' and B', respectively, had been modified compared to the original epitopes on the human cardiac Troponin T sequence (P45379/UniProtKB) in order to reduce the binding affinity for each of the Fabs thereto. Under these circumstances the dynamics of the effect of hetero-bi-valent binding is better visible, e.g. by analyzing binding affinity with the Biacore™ Technology.

1.5 Biomolecular Interaction Analysis

For this experiment a Biacore™ 3000 instrument (GE Healthcare) was used with a Biacore™ SA sensor mounted into the system at T=25° C. Preconditioning was done at 100 μl/min with 3×1 min injection of 1 M NaCl in 50 mM NaOH and 1 min 10 mM HCl.

HBS-ET (10 mM HEPES pH 7.4, 150 mM NaCl, 1 mM EDTA, 0.05% Tween® 20 was used as system buffer. The sample buffer was identical to the system buffer.

The Biacore™ 3000 System was driven under the control software V1.1.1. Flow cell 1 was saturated with 7 RU D-biotin. On flow cell 2, 1063 RU biotinylated ssDNA linker L1 was immobilized. On flow cell 3, 879 RU biotinylated ssDNA linker L2 was immobilized. On flow cell 4, 674 RU biotinylated ssDNA linker L3 was captured.

Thereafter, Fab' fragment DNA conjugate A" was injected at 600 nM. Fab' fragment DNA conjugate B" was injected into the system at 900 nM. The conjugates were injected for 3 min at a flow rate of 2 µl/min. The conjugates were consecutively injected to monitor the respective saturation signal of each Fab' fragment DNA conjugate on its respective linker. Fab' combinations were driven with a single Fab' fragment DNA conjugate A", a single Fab' fragment DNA conjugate B" and both Fab' fragment DNA conjugates A" and B" present on the respective linker. Stable baselines were generated after the linkers have been saturated by the Fab' fragment DNA conjugates, which was a prerequisite for further kinetic measurements.

The artificial peptidic analytes TnT-1 and TnT-2 were injected as analytes in solution into the system in order to interact with the surface presented Fab' fragments.

TnT-1 was injected at 500 nM, TnT-2 was injected at 900 nM analyte concentration. Both peptides were injected at 50 µl/min for 4 min association time. The dissociation was monitored for 5 min. Regeneration was done by a 1 min injection at 50 µl/min of 50 mM NaOH over all flow cells.

Kinetic data was determined using the Biaevaluation software (V.4.1). The dissociation rate kd (1/s) of the TnT-1 and TnT-2 peptides from the respective surface presented Fab' fragment combinations was determined according to a linear Langmuir 1:1 fitting model. The complex halftime in min were calculated according to the solution of the first order kinetic equation: $\ln(2)/(60*kd)$.

Results:

The experimental data given in Tables 1 and 2, respectively demonstrate an increase in complex stability between analyte (TnT-1 or TnT-2), respectively, and the various heterobi-valent Fab'-Fab' dimers A"-B" as compared to the monovalent dsDNA Fab' A" or B" conjugate, respectively. This effect is seen in each Table in line 1 compared to lines 2 and 3.

TABLE 1

Analysis data using TnT-1 with linkers of various length

| Fab' fragment DNA conjugate A" | Fab' fragment DNA conjugate B" | kd (1/s) | t1/2 diss (min) |
|---|---|---|---|
| a) Linker L1 | | | |
| x | x | 6.6E−03 | 1.7 |
| x | — | 3.2E−02 | 0.4 |
| — | x | 1.2E−01 | 0.1 |
| b) Linker L2 | | | |
| x | x | 4.85E−03 | 2.4 |
| x | — | 2.8E−02 | 0.4 |
| — | x | 1.3E−01 | 0.1 |
| c) linker L3 | | | |

| Fab' fragment DNA conjugate A" | Fab' fragment DNA conjugate B" | kd (1/s) | t1/2 diss (min) |
|---|---|---|---|
| x | x | 2.0E−03 | 5.7 |
| x | — | 1.57E−02 | 0.7 |
| — | x | 1.56E−02 | 0.7 |

TABLE 2

Analysis data using TnT-2 with linkers of various length

| Fab' fragment DNA conjugate A" | Fab' fragment DNA conjugate B" | kd (1/s) | t1/2 diss (min) |
|---|---|---|---|
| a) Linker L1 | | | |
| x | x | 1.4E−02 | 0.8 |
| x | — | 4.3E−02 | 0.3 |
| — | x | 1.4E−01 | 0.1 |
| b) Linker L2 | | | |
| x | x | 4.9E−03 | 2.3 |
| x | — | 3.5E−02 | 0.3 |
| — | x | 1.3E−01 | 0.1 |
| c) Linker L3 | | | |
| x | x | 8.0E−03 | 1.5 |
| x | — | 4.9E−02 | 0.2 |
| — | x | 3.2E−01 | 0.04 |

The avidity effect is further dependent on the length of the linker. In the sub-tables shown under Table 1, i.e. for the artificial analyte TnT-1, the linker L3 comprising a 31 mer thymidine-based spacer shows the lowest dissociation rate or highest complex stability.

In the sub-tables shown under Table 2 the linker L2 comprising an 11 mer thymidine-based spacer exhibits the lowest dissociation rate or highest complex stability for the artificial analyte TnT-2.

These data taken together demonstrate that the flexibility in linker length as inherent to the approach given in the present disclosure is of great utility and advantage.

Example 2

Bi-Valent Binding Agent to Phosphorylated IGF-1R 2.1 Monoclonal Antibody Development (mAb 8.1.2 and mAb 1.4.168)

a) Immunization of Mice

BALB/C mice are immunized at week 0, 3, 6 and 9, respectively. Per immunization 100 µg of the conjugate comprising the phosphorylated peptide pIGF-1R (1340-1366) (SEQ ID NO:11) is used. This peptide had been phosphorylated at tyrosine 1346 (=1346-pTyr) and coupled to KLH via the C-terminal cysteine (=Aoc-Cys-MP-KLH-1340) to yield the conjugate used for immunization. At weeks 0 and 6, respectively, the immunization is carried out intraperitoneally and at weeks 3 and 9, respectively, subcutaneously at various parts of the mouse body.

b) Fusion and Cloning

Spleen cells of immunized mice are fused with myeloma cells according to Galfre G., and Milstein C., Methods in Enzymology 73 (1981) 3-46. In this process ca $1 \times 10^8$ spleen cells of an immunized mouse are mixed with $2 \times 10^7$ myeloma cells a(P3X63-Ag8653, ATCC CRL1580) and centrifuged (10 min at 250 g and 37° C.). The cells are then washed once with RPMI 1640 medium without fetal calf serum (FCS) and centrifuged again at 250 g in a 50 ml conical tube. The supernatant is discarded, the cell sediment is gently loosened by tapping, 1 ml PEG (molecular weight 4000, Merck, Darmstadt) is added and mixed by pipetting. After 1 min incubation in a water bath at 37° C., 5 ml RPMI 1640 without FCS is added drop-wise at room temperature within a period of 4-5 min. This step is repeated with additional 10 ml RPMI 1640 without FCS. Afterwards 25 ml RPMI 1640 containing 10% FCS is added followed by an incubation step at 37° C., 5% $CO_2$ for 30 minutes. After centrifugation for 10 min at 250 g and 4° C. the sedimented cells are taken up in RPMI 1640 medium containing 10% FCS and seeded out in hypoxanthine-azaserine selection medium (100 mmol/l hypoxanthine, 1 µg/ml azaserine in RPMI 1640+10% FCS). Interleukin 6 at 100 U/ml is added to the medium as a growth factor. After 7 days the medium is exchanged with fresh medium. On day 10, the primary cultures are tested for specific antibodies. Positive primary cultures are cloned in 96-well cell culture plates by means of a fluorescence activated cell sorter.

c) Immunoglobulin Isolation from the Cell Culture Supernatants

The hybridoma cells obtained are seeded out at a density of $1 \times 10^7$ cells in CELLine 1000 CL flasks (Integra). Hybridoma cell supernatants containing IgGs are collected twice a week. Yields typically range between 400 µg and 2000 µg of monoclonal antibody per 1 ml supernatant. Purification of the antibody from culture supernatant was carried out using conventional methods of protein chemistry (e.g. according to Bruck, C., Methods in Enzymology 121 (1986) 587-695).

2.2 Synthesis of Hybridizable Oligonucleotides

The following amino modified precursors, comprising the sequences given in SEQ ID NOs: 5 and 6, respectively, were synthesized according to standard methods. The below given oligonucleotides not only comprise the so-called aminolinker, but also a fluorescent dye. As the skilled artisan will readily appreciate, this fluorescent dye is very convenient to facilitate purification of the oligonucleotide as such, as well as of components comprising them.

```
a)
5'-Fluorescein-AGT CTA TTA ATG CTT CTG C-
(Spacer C3)3-C7Aminolinker-(SEQ ID NO: 6);

b)
5'-Cy5 AGT CTA TTA ATG CTT CTG C-(Spacer C3)3-
C7Aminolinker-(SEQ ID NO: 6);

c)
5'-Aminolinker-(Spacer C3)3-AGT TCT ATC GTC
GTC CA-Fluorescein-3' (SEQ ID NO: 5);

d)
5'-Fluorescein-(beta L AGT CTA TTA ATG CTT CTG
C)-(Spacer C3)3-C7Aminolinker-;
(beta L indicates that this is an L-DNA
oligonucleotide) (SEQ ID NO: 6)
and e)
5'-Aminolinker-(Spacer C3)3-(beta L-AGT TCT
ATC GTC GTC CA)-Fluorescein-3'
(beta L indicates that this is an L-DNA
oligonucleotide)(SEQ ID NO: 5).
```

Synthesis was performed on an ABI 394 synthesizer at a 10 µmol scale in the trityl on (for 5' amino modification) or trityl off mode (for 3' amino modification) using commercially available CPGs as solid supports and standard dA(bz), dT, dG (iBu) and dC(Bz) phosphoramidites (Sigma Aldrich).

The following amidites, amino modifiers and CPG supports were used to introduce the C3-spacer, a dye and amino moieties, respectively, during oligonucleotide synthesis:

Spacer Phosphoramidite C3 (3-(4,4'-Dimethoxytrityloxy) propyl-1-[(2-cyanoethyl)-(N,N-diisopropyl)]-phosphoramidite (Glen Research);

5' amino modifier is introduced by using 5'-Amino-Modifier C6 (6-(4-Monomethoxytritylamino)hexyl-(2-cyanoethyl)-(N,N-diisopropyl)-phosphoramidite (Glen Research);

5'-Fluorescein Phosphoramidite 6-(3',6'-dipivaloylfluoresceinyl-6-carboxamido)-hexyl-1-O-(2-cyanoethyl)-(N,N-diisopropyl)-phosphoramidite (Glen Research);

Cy5™ Phosphoramidite 1-[3-(4-monomethoxytrityloxy) propyl]-1'-[3-[(2-cyanoethyl)-(N,N-diisopropyl phosphoramidityl]propyl]-3,3,3',3'-tetramethylindodicarbocyanine chloride (Glen Research);

LightCycler Fluoresceine CPG 500 A (Roche Applied Science); and

3'-Amino Modifier TFA Amino C-6 lcaa CPG 500 A (Chemgenes),

For Cy5 labeled oligonucleotides, dA(tac), dT, dG(tac) dC(tac) phosphoramidites, (Sigma Aldrich), were used and deprotection with 33% ammonia was performed for 2 h at room temperature.

L-DNA oligonucleotides were synthesized by using beta-L-dA(bz), dT, dG (iBu) and dC(Bz) phosphoramidites (Chemgenes)

Purification of fluorescein modified hybridizable oligonucleotides was performed by a two step procedure: First the oligonucleotides were purified on reversed-phase HPLC (Merck-Hitachi-HPLC; RP-18 column; gradient system [A: 0.1 M (Et3NH)OAc (pH 7.0)/MeCN 95:5; B: MeCN]: 3 min, 20% B in A, 12 min, 20-50% B in A and 25 min, 20% B in A with a flow rate of 1.0 ml/min, detection at 260 nm. The fractions (monitored by analytical RP HPLC) containing the desired product were combined and evaporated to dryness. (Oligonucleotides modified at the 5' end with monomethoxytrityl protected alkylamino group are detritylated by incubating with 20% acetic acid for 20 min). The oligomers containing fluorescein as label were purified again by IEX chromatography on a HPLC [Mono Q column: Buffer A: Sodium hydroxide (10 mM/l; pH ~12) Buffer B 1M Sodium chloride dissolved in Sodium hydroxide (10 mM/l; pH ~12) gradient: in 30 minutes from 100% buffer A to 100% buffer B flow 1 ml/min detection at 260 nm]. The product was desalted via dialysis.

Cy5 labeled oligomers were used after the first purification on reversed-phase HPLC (Merck-Hitachi-HPLC; RP-18 column; gradient system [A: 0.1 M (Et3NH)OAc (pH 7.0)/MeCN 95:5; B: MeCN]: 3 min, 20% B in A, 12 min, 20-50% B in A and 25 min, 20% B in A with a flow rate of 1.0 ml/min, detection at 260 nm. The oligomers were desalted by dialysis and lyophilized on a Speed-Vac evaporator to yield solids which were frozen at −24° C.

2.3 Activation of Hybridizable Oligonucleotides

The amino modified oligonucleotides from Example 2 were dissolved in 0.1 M sodium borate buffer pH 8.5 buffer (c=600 µmol) and reacted with a 18-fold molar excess of Sulfo SMCC (Sulfosuccinimidyl 4-[N-maleimidomethyl] cyclohexane-1-carboxylate dissolved in DMF (c=3 mg/100 µl) from Thermo Scientific, The reaction product was thoroughly dialyzed against water in order to remove the hydrolysis product of sulfoSMCC 4-[N-maleimidomethyl]cyclohexane-1-carboxylate.

The dialysate was concentrated by evaporation and directly used for conjugation with a monovalent binder comprising a thiol group.

2.4 Synthesis of Linker Oligonucleotides Comprising Hybridizable Oligonucleotides at Both Ends Oligonucleotides were synthesized by standard methods on an ABI 394 synthesizer at a 10 µmol scale in the trityl on mode using commercially available dT-CPG as solid supports and using standard dA(bz), dT, dG (iBu) and dC(Bz) phosphoramidites (Sigma Aldrich).

L-DNA oligonucleotides were synthesized by using commercially available beta L-dT-CPG as solid support and beta-L-dA(bz), dT, dG (iBu) and dC(Bz) phosphoramidites (Chemgenes)

Purification of the oligonucleotides was performed as described under Example 3 on a reversed-phase HPLC. The fractions (analyzed/monitored by analytical RP HPLC) containing the desired product were combined and evaporated to dryness. Detriylation was performed by incubating with 80% acetic acid for 15 min) The acetic acid was removed by evaporation. The reminder was dissolved in water and lyophilized The following amidites and CPG supports were used to introduce the C18 spacer, digoxigenin and biotin group during oligonucleotide synthesis:

Spacer Phosphoramidite 18 (18-O-Dimethoxytritylhexaethyleneglycol,1-[(2-cyanoethyl)-(N,N-diisopropyl)]-phosphoramidite (Glen Research);

Biotin-dT (5'-Dimethoxytrityloxy-5-[N-((4-t-butylbenzoyl)-biotinyl)-aminohexyl]-3-acrylimido]-2'-deoxyUridine-3'-[(2-cyanoethyl)-(N,N-diisopropyl)]-phosphoramidite (Glen Research);

Biotin Phosphoramidite1-Dimethoxytrityloxy-2-(N-biotinyl-4-aminobutyl)-propyl-3-O-(2-cyanoethyl)-(N,N-diisopropyl)-phosphoramidite and 5'-Dimethoxytrityl-5-[N-(trifluoroacetylaminohexyl)-3-acrylimido]-2'-deoxy uridine, 3'-[(2-cyanoethyl)-(N,N-diisopropyl)]-phosphoramidite for amino modification and postlabeling with Digoxigenin-N-Hydroxyl-succininimidyl ester.

The following bridging constructs or linkers were synthesized:

Linker 1:
5'-G CAG AAG CAT TAA TAG ACT-TGG ACG ACG
ATA GAA CT-3' (SEQ ID NO: 7)-(SEQ ID NO: 8)

Linker 2:
5'-G CAG AAG CAT TAA TAG ACT-(T40)-TGG
ACG ACG ATA GAA CT-3' (SEQ ID NO: 7)-(T40)-
(SEQ ID NO: 8)

Linker 3:
5'-[B-L]G CAG AAG CAT TAA TAG ACT-(Biotin-dT)-
TGG ACG ACG ATA GAA CT-3' (SEQ ID NO: 7)-
(Biotin-dT)-(SEQ ID NO: 8)

Linker 4:
5'-[B-L]G CAG AAG CAT TAA TAG ACT-T5-(Biotin-dT)-
T5-TGG ACG ACG ATA GAA CT-3' (SEQ ID NO: 7)-T5-
(Biotin-dT)-T5-(SEQ ID NO: 8)

Linker 5:
5'-[B-L]G CAG AAG CAT TAA TAG ACT-T20-(Biotin-dT)-
T20-TGG ACG ACG ATA GAA CT-3' (SEQ ID NO: 7)-T20-
(Biotin-dT)-T20-(SEQ ID NO: 8)

Linker 6:
5'-[B-L]G CAG AAG CAT TAA TAG ACT-T30-(Biotin-dT)-
T30-TGG ACG ACG ATA GAA CT-3' (SEQ ID NO: 7)-T30-
(Biotin-dT)-T30-(SEQ ID NO: 8)

Linker 7:
5'-GCA GAA GCA TTA ATA GAC T T5-(Biotin-dT)-
T5 TG GAC GAC GAT AGA ACT-3' (SEQ ID NO: 7)-T5-
(Biotin-dT)-T5-(SEQ ID NO: 8)

Linker 8:
5'-GCA GAA GCA TTA ATA GAC T T10-(Biotin-dT)-
T10 TGG ACG ACG ATA GAA CT-3' (SEQ ID NO: 7)-T10-
(Biotin-dT)-T10-(SEQ ID NO: 8)

Linker 9:
5'-GCA GAA GCA TTA ATA GAC T T15-(Biotin-dT)-
T15 TGG ACG ACG ATA GAA CT-3' (SEQ ID NO: 7)-T15-
(Biotin-dT)-T15-(SEQ ID NO: 8)

Linker 10:
5'-GCA GAA GCA TTA ATA GAC T T20-(Biotin-dT)-
T20 TGG ACG ACG ATA GAA CT-3' (SEQ ID NO: 7)-T20-
(Biotin-dT)-T20-(SEQ ID NO: 8)

Linker 11:
5'-G CAG AAG CAT TAA TAG ACT-Spacer C18-
(Biotin-dT)-Spacer C18-TGG ACG ACG ATA GAA
CT-3' (SEQ ID NO: 7)-Spacer C18-(Biotin-dT)-
Spacer C18-(SEQ ID NO: 8)

Linker 12:
5'-G CAG AAG CAT TAA TAG ACT-(Spacer C18)2-
(Biotin-dT)-(Spacer C18)2-TGG ACG ACG ATA GAA
CT-3' (SEQ ID NO: 7)-(Spacer C18)2-(Biotin-dT)-
(Spacer C18)2-(SEQ ID NO: 8)

Linker 13:
5'-G CAG AAG CAT TAA TAG ACT-(Spacer C18)3-
(Biotin-dT)-(Spacer C18)3-TGG ACG ACG ATA GAA
CT-3' (SEQ ID NO: 7)-(Spacer C18)3-(Biotin-dT)-
(Spacer C18)3-(SEQ ID NO: 8)

Linker 14:
5'-G CAG AAG CAT TAA TAG ACT-(Spacer C18)4-
(Biotin-dT)-(Spacer C18)4-TGG ACG ACG ATA GAA
CT-3' (SEQ ID NO: 7)-(Spacer C18)4-(Biotin-dT)-
(Spacer C18)4-(SEQ ID NO: 8)

Linker 15:
5'-G CAG AAG CAT TAA TAG ACT-T20-(Dig-dT)-T20-
TGG ACG ACG ATA GAA CT-3' (SEQ ID NO: 7)-T20-
(Dig-dT)T20-(SEQ ID NO: 8)

Linker 16:
5'-G CAG AAG CAT TAA TAG ACT-(Dig-dT)-TGG ACG
ACG ATA GAA CT-3' (SEQ ID NO: 7)-(Dig-dT)-
(SEQ ID NO: 8)

Linker 17:
5'-G CAG AAG CAT TAA TAG ACT-(Biotin-dT)-TGG
ACG ACG ATA GAA CT-3' (SEQ ID NO: 7)-(Biotin-dT)-
(SEQ ID NO: 8)

The above bridging construct examples comprise at least a first hybridizable oligonucleotide and a second hybridizable oligonucleotide. Linkers 3 to 17 in addition to the hybridizable nucleic acid stretches comprise a central biotinylated or digoxigenylated thymidine, respectively, or a spacer consisting of thymidine units of the length given above.

The 5'-hybridizable oligonucleotide corresponds to SEQ ID NO:7 and the 3'-hybridizable oligonucleotide corresponds to SEQ ID NO:8, respectively. The oligonucleotide of SEQ ID NO:7 will readily hybridize with the oligonucleotide of SEQ ID NO:5. The oligonucleotide of SEQ ID NO:8 will readily hybridize with the oligonucleotide of SEQ ID NO:6.

In the above bridging construct examples [B-L] indicates that an L-DNA oligonucleotide sequence is given; spacer C 18, Biotin and Biotin dT respectively, refer to the C18 spacer, the Biotin and the Biotin-dT as derived from the above given building blocks; and T with a number indicates the number of thymidine residues incorporated into the linker at the position given.

2.5 Assembly of Dual Binder Construct

A) Cleavage of IgGs and Labeling of Fab' Fragments with ssDNA

Purified monoclonal antibodies were cleaved with the help of pepsin protease yielding F(ab')2 fragments that are subsequently reduced to Fab' fragments by treatment with low concentrations of cysteamine at 37° C. The reaction is stopped via separation of cysteamine on a PD 10 column. The Fab' fragments are labeled with an activated oligonucleotide as produced according to Example 3. This single-stranded DNA (=ssDNA) bears a thiol-reactive maleimido group that reacts with the cysteines of the Fab' hinge region. In order to obtain high percentages of single-labeled Fab' fragments the relative molar ratio of ssDNA to Fab'-fragment is kept low. Purification of single-labeled Fab' fragments (ssDNA: Fab'=1:1) occurs via ion exchange chromatography (column: Source 15 Q PE 4.6/100, Pharmacia/GE). Verification of efficient purification is achieved by analytical gel filtration and SDS-PAGE.

B) Assembly of an Anti-pIGF-1R Dual Binder.

The anti-pIGF-1R dual binder is based on two Fab' fragments that target different epitopes of the intracellular domain of IGF-1R: Fab' 8.1.2 detects a phosphorylation site (pTyr 1346) and Fab' 1.4.168 a non-phospho site of the said target protein. The Fab' fragments have been covalently linked to single-stranded DNA (ssDNA): Fab' 1.4.168 to a 17mer ssDNA comprising SEQ ID NO:6 and containing fluorescein as an fluorescent marker and Fab' 8.1.2 to a 19mer ssDNA comprising SEQ ID NO:5 and containing Cy5 as fluorescent marker. In the following, these Fab's with covalently bound 17mer or 19mer ssDNA are named ssFab' 1.4.168 and ssFab' 8.1.2 respectively. Dual binder assembly is mediated by a linker (i.e. a bridging construct comprising two complementary ssDNA oligonucleotides (SEQ ID NOs:7 and 8, respectively) that hybridize to the corresponding ssDNAs of the ssFab' fragments. The distance between the two ssFab' fragments of the dual binder can be modified by using spacers, e.g. C18-spacer or DNAs of different length, respectively.

Figure 1B:
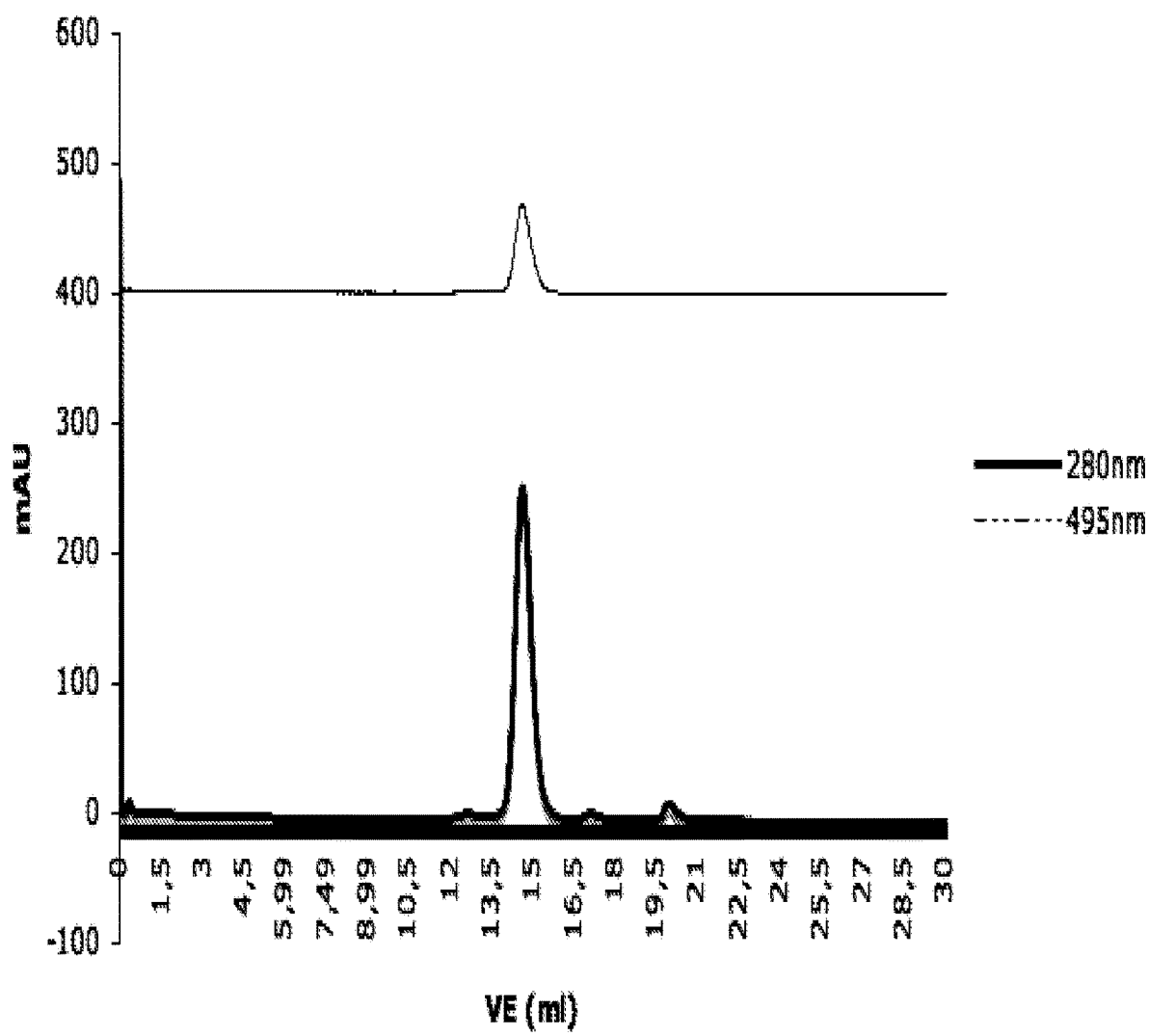
FIG. 1B is an analytical gel filtration experiments assessing efficiency of the anti-pIGF1-R dual binder assembly. Diagrams A, B and C show the elution profile of the individual dual binder components (flourescein-ssFab' 1.4.168, Cy5-ssFab' 8.1.2 and linker DNA (T=0); Fab' denotes an Fab'-fragment conjugated to a single-stranded oligonucleotide). Diagram D shows the elution profile after the 3 components needed to form the bi-valent binding agent had been mixed in a 1:1:1 molar ratio. The thicker (bottom) curve represents absorbance measured at 280 nm indicating the presence of the ssFab' proteins or the linker DNA, respectively. The thinner top curve in B) and D) (absorbance at 495 nm) indicates the presence of fluorescein and the thinner top curve in a) and the middle curve in d) (absorbance at 635 nm) indicates the presence of Cy5. Comparison of the elution volumes of the single dual binder components ($VE_{ssFab'\ 1.4.168}$~15 ml; $VE_{ssFab'\ 8.1.2}$~15 ml; $VE_{linker}$~16 ml) with the elution volume of the reaction mix ($VE_{mix}$~12 ml) demonstrates that the dual binder assembly reaction was successful (rate of yield: ~90%). The major 280 nm peak that represents the eluted dual binder nicely overlaps with the major peaks in the 495 nm and 635 nm channel, proving the presence of both ssFab' 8.1.2 and ssFab'1.4.168 in the peak representing the bi-valent binding agent.
Figure 1D:
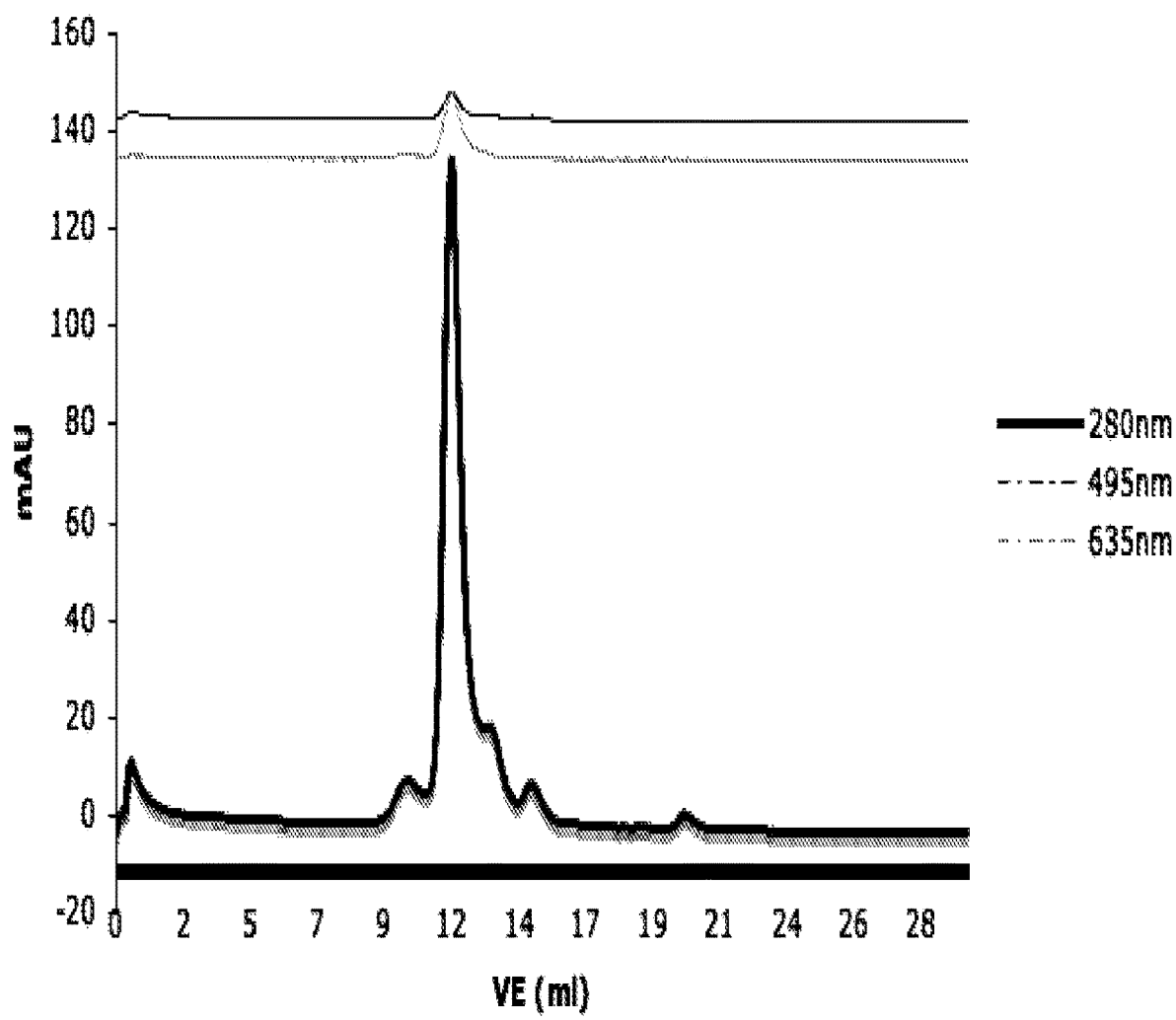
FIG. 1D is an analytical gel filtration experiments assessing efficiency of the anti-pIGF1-R dual binder assembly. Diagrams A, B and C show the elution profile of the individual dual binder components (flourescein-ssFab' 1.4.168, Cy5-ssFab' 8.1.2 and linker DNA (T=0); Fab' denotes an Fab'-fragment conjugated to a single-stranded oligonucleotide). Diagram D shows the elution profile after the 3 components needed to form the bi-valent binding agent had been mixed in a 1:1:1 molar ratio. The thicker (bottom) curve represents absorbance measured at 280 nm indicating the presence of the ssFab' proteins or the linker DNA, respectively. The thinner top curve in B) and D) (absorbance at 495 nm) indicates the presence of fluorescein and the thinner top curve in a) and the middle curve in d) (absorbance at 635 nm) indicates the presence of Cy5. Comparison of the elution volumes of the single dual binder components ($VE_{ssFab'\ 1.4.168}$~15 ml; $VE_{ssFab'\ 8.1.2}$~15 ml; $VE_{linker}$~16 ml) with the elution volume of the reaction mix ($VE_{mix}$~12 ml) demonstrates that the dual binder assembly reaction was successful (rate of yield: ~90%). The major 280 nm peak that represents the eluted dual binder nicely overlaps with the major peaks in the 495 nm and 635 nm channel, proving the presence of both ssFab' 8.1.2 and ssFab'1.4.168 in the peak representing the bi-valent binding agent.
Figure 2:
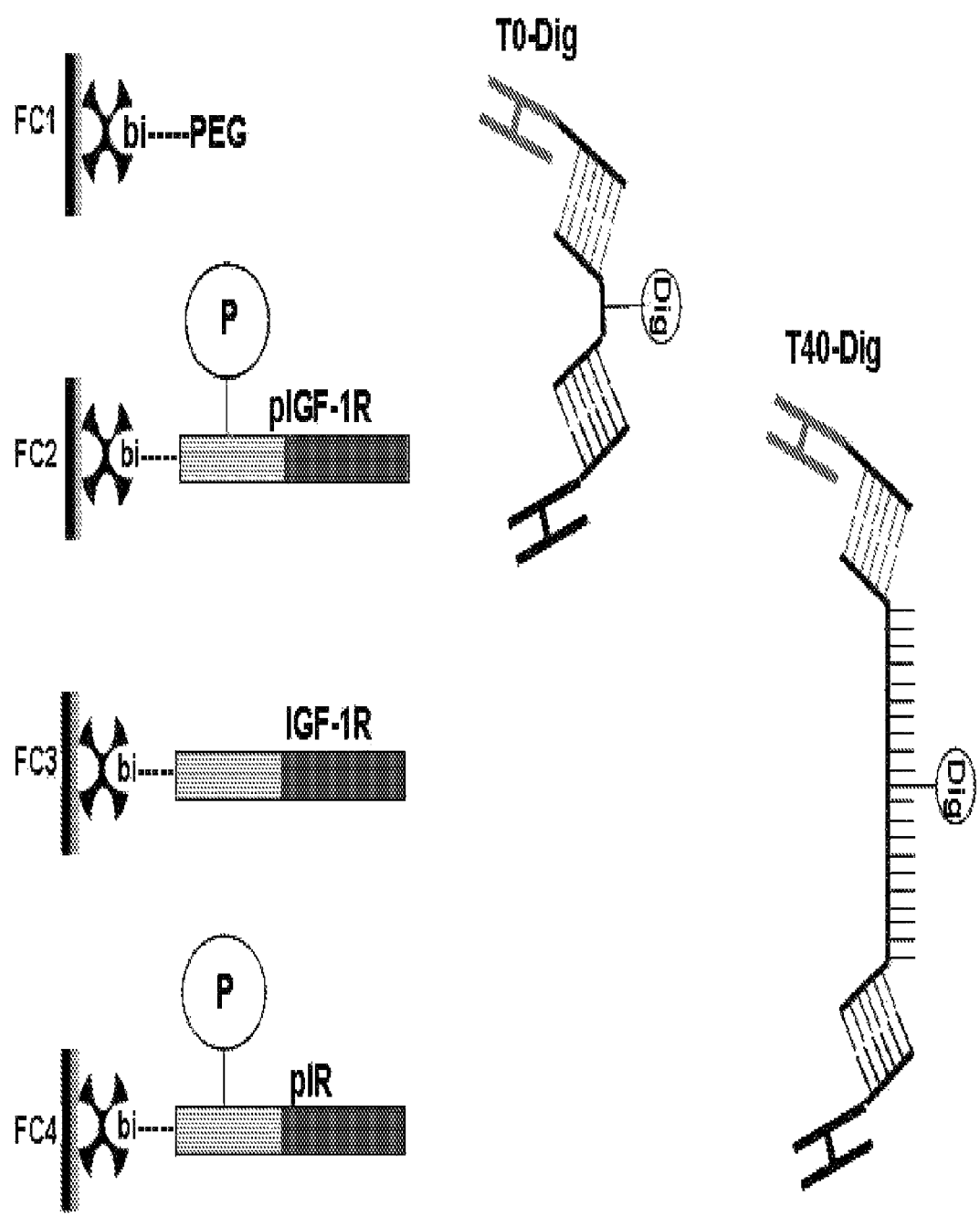
FIG. 2 presents a scheme of the Biacore™ experiment. Schematically and exemplarily, two binding molecules in solution are shown: The T0-T-Dig (linker 16), bi-valent binding agent and the T40-T-Dig (linker 15), bi-valent binding agent. Both these bi-valent binding agents only differ in their linker-length (a central digoxigenylated T with no additional T versus 40 additional Ts (20 on each side of the central T-Dig), between the two hybridizing nucleic acid sequences). Furthermore, ssFab' fragments 8.1.2 and 1.4.168 were used.

For assembly evaluation the dual binder components ssFab' 8.1.2, ssFab' 1.4.168 and the linker constructs (I) (=linker 17 of example 2.4) 5'-G CAG AAG CAT TAA TAG ACT T(-Bi)-TGG ACG ACG ATA GAA CT-3' (SEQ ID NO:7)-(Biotin-dT)-(SEQ ID NO:8) and (II) (=linker 10 of example 2.4) 5'-G CAG AAG CAT TAA TAG ACT-(T20)-T(-Bi)-(T20)-TGG ACG ACG ATA GAA CT-3' (SEQ ID NO:7)-T20-(Biotin-dT)-T20-(SEQ ID NO:8) were mixed in equimolar quantities at room temperature. After a 1 minute incubation step the reaction mix was analyzed on an analytical gel filtration column (Superdex™ 200, 10/300 GL, GE Healthcare). Comparison of the elution volumes (VE) of the single dual binder components with the VE of the reaction mix demonstrates that the dual binder has been formed successfully (FIG. 1). (The biotinylated thymidine (T(-Bi)) in the middle of both of the linkers is without function in these experiments.)

2.6 Biacore™ Experiment Assessing Binding of Anti-pIGF-1R Dual Binder to Immobilized IGF-1R and IR Peptides For this experiment a Biacore™ 2000 instrument (GE Healthcare) was used with a Biacore™ SA sensor mounted into the system at T=25° C. Preconditioning occurred at 100 μl/min with 3×1 min injection of 1 M NaCl in 50 mM NaOH and 1 min 10 mM HCl.

HBS-ET (10 mM HEPES pH 7.4, 150 mM NaCl, 1 mM EDTA, 0.05% Tween® 20 was used as system buffer. The sample buffer was identical with the system buffer. The Biacore™ 2000 System was driven under the control software V1.1.1.

Subsequently biotinylated peptides were captured on the SA surface in the respective flow cells. 16 RU of IGF-1R (1340-1366)[1346-pTyr; Glu(Bi-PEG-1340]amid (i.e. the—1346 tyrosine phosphorylated—peptide of SEQ ID NO:11 comprising a PEG-linker bound via glutamic acid corresponding to position 1340 and being biotinylated at the other end of the linker) was captured on flow cell 2. 18 RU of IGF-1R(1340-1366); Glu(Bi-PEG-1340]amid (i.e. the—1346 tyrosine non-phosphorylated—peptide of SEQ ID NO:11 comprising a PEG-linker bound via glutamic acid corresponding to position 1340 and being biotinylated at the other end of the linker) was captured on flow cell 3. 20 RU of hIR(1355-1382)[1361-pTyr; Glu(Bi-PEG-1355]amid (i.e. the—1361 tyrosine phosphorylated—peptide of SEQ ID NO:12 comprising a PEG-linker bound via glutamic acid corresponding to position 1355 of human insulin receptor and being biotinylated at the other end of the linker) was captured on flow cell 4. Finally all flow cells were saturated with d-biotin.

For the Dual Binder formation the assembly protocol as described in Example 2.5 was used. When individual runs with only one of the two ssFab's were performed, the absence or presence of linker DNA did not affect the association or dissociation curves (data not shown).

100 nM of analyte (i.e. in these experiments a bi-valent dual binding agent) in solution was injected at 50 μl/min for 240 sec association time and dissociation was monitored for 500 sec. Efficient regeneration was achieved by using a 1 min injection step at 50 μl/min with 80 mM NaOH. Flow cell 1 served as a reference. A blank buffer injection was used instead of an antigen injection to double reference the data by buffer signal subtraction.

In each measurement cycle one of the following analytes in solution was injected over all 4 flow cells: 100 nM ssFab' 8.1.2, 100 nM ssFab' 1.4.168, a mixture of 100 nM ssFab' 8.1.2 and 100 nM ssFab', 100 nM bi-valent binding agent consisting of ssFab' 8.1.2 and ssFab' 1.4.168 hybridized on linker (III) (5'-G CAG AAG CAT TAA TAG ACT-T(20)-T(-Dig)-(T20)-TGG ACG ACG ATA GAA CT-3' (SEQ ID NO:7)-T20-(Dig-dT)-T20-(SEQ ID NO:8) (=linker 15 of example 2.4)), and 100 nM bi-valent binding agent consisting of ssFab' 8.1.2 and ssFab' 1.4.168 hybridized on linker (IV) (5'-G CAG AAG CAT TAA TAG ACT-T(-Dig)-TGG ACG ACG ATA GAA CT-3' (SEQ ID NO:7)-(Dig-dT)-(SEQ ID NO:8) (=linker 16 of example 2.4)), respectively. (The digoxigenylation of the middle thymidine (T(-Dig)) in the above linkers is without relevance to these experiments.)

The signals were monitored as time-dependent BIAcore™ sensorgrams.

Report points were set at the end of the analyte association phase (Binding Late, BL) and at the end of the analyte dissociation phase (Stability Late, SL) to monitor the response unit signal heights of each interaction. The dissociation rates kd (1/s) were calculated according to a linear 1:1 Langmuir fit using the Biacore™ evaluation software 4.1. The complex halftimes in minutes were calculated upon the formula ln(2)/(60*kd).

Figure 3:
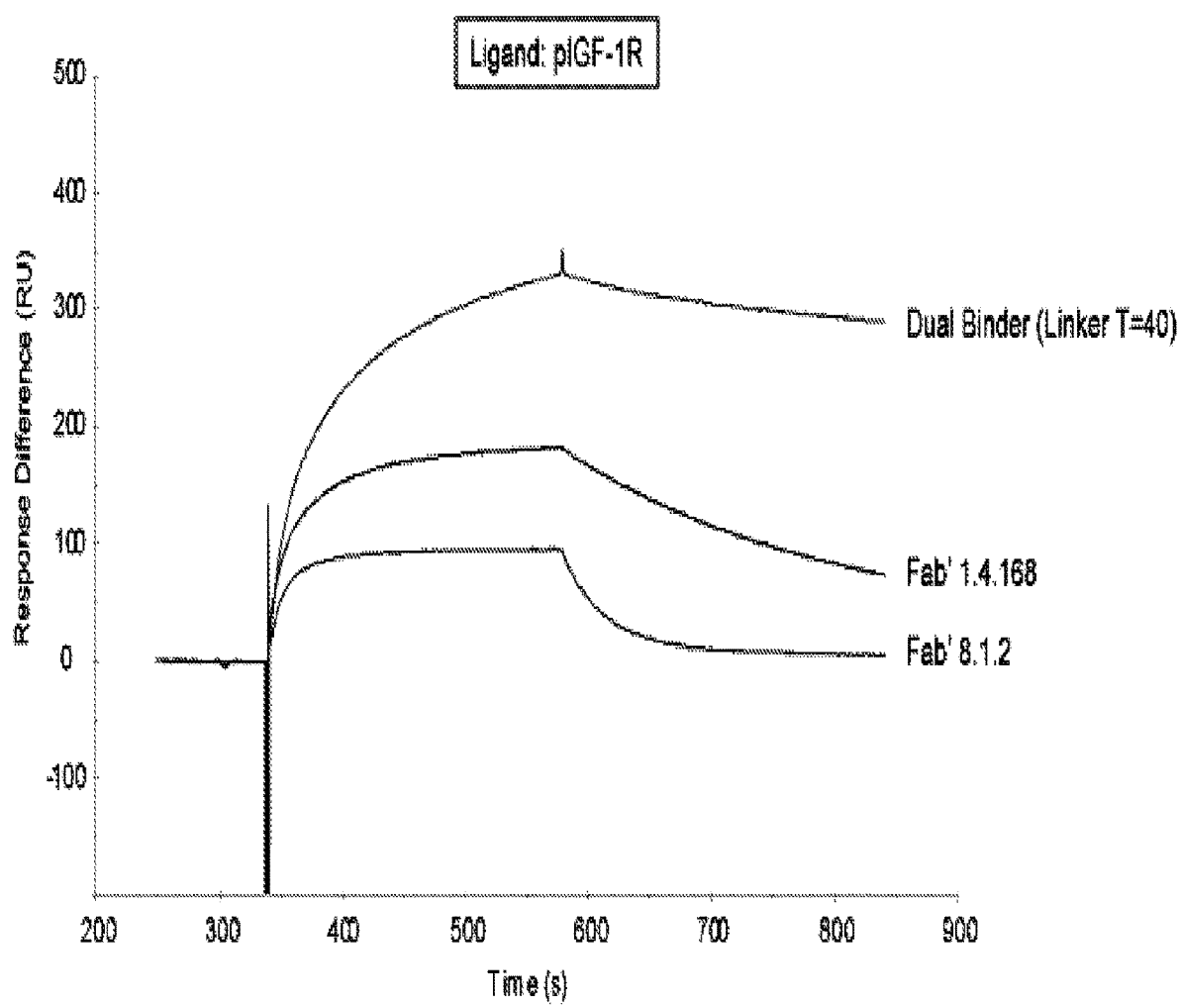
FIG. 3 presents a Biacore™ sensorgram with overlay plot of three kinetics showing the interaction of 100 nM bi-valent binding agent (consisting of ssFab' 8.1.2 and ssFab' 1.4.168 hybridized on the T40-T-Dig ssDNA-linker, i.e. linker 15) with the immobilized peptide pIGF-1R compared to the binding characteristics of 100 nM ssFab' 1.4.168 or 100 nM ssFab' 8.1.2 to the same peptide. Highest binding performance is obtained with the Dual Binder construct, clearly showing, that the cooperative binding effect of the Dual Binder increases affinity versus the target peptide pIGF-1R.
Figure 4:
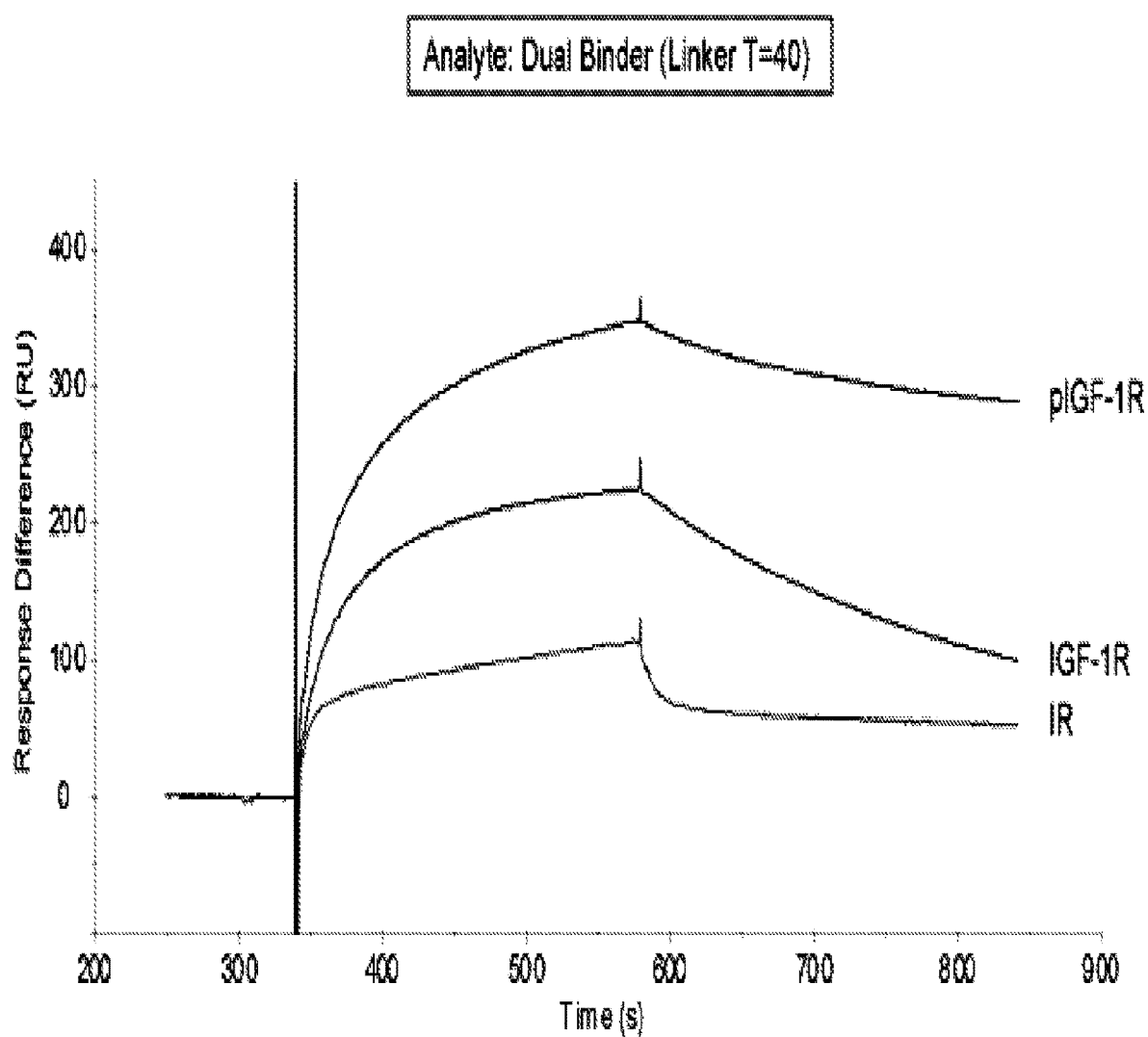
FIG. 4 presents a Biacore™ sensorgram with overlay plot of three kinetics showing the interactions of the bi-valent binding agent consisting of ssFab' 8.1.2 and ssFab' 1.4.168 hybridized on the T40-T-Dig ssDNA-linker, i.e. linker 15, with immobilized peptides pIGF-1R (phosphorylated IGF-1R), IGF-1R or pIR (phosphorylated insulin receptor). Highest binding performance is obtained with the pIGF-1R peptide, clearly showing, that the cooperative binding effect of the Dual Binder increases specificity versus the target peptide pIGF-1R as compared to e.g. the phosphorylated insulin receptor peptide (pIR).
Figure 5:
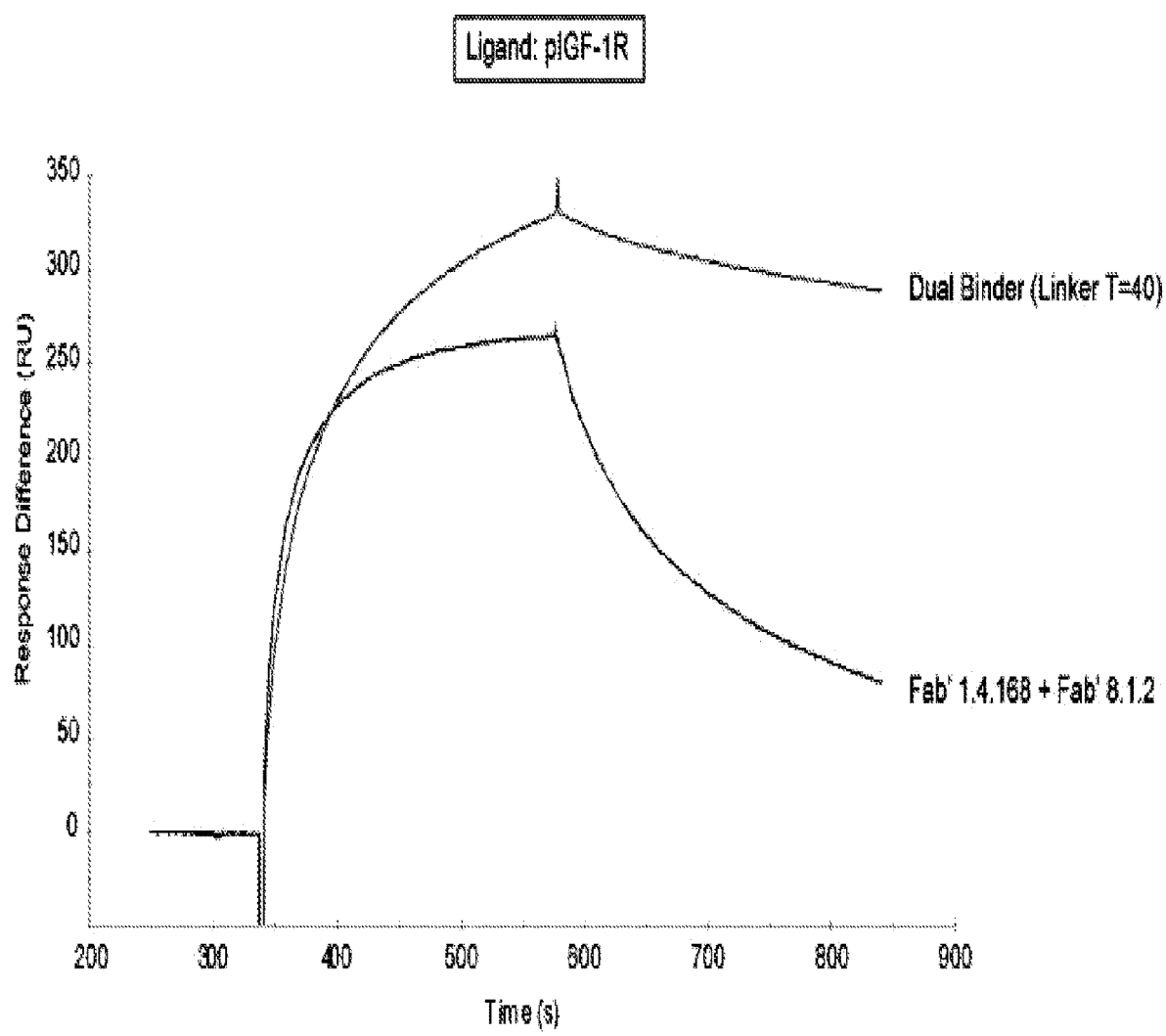
FIG. 5 presents a Biacore™ sensorgram with overlay plot of two kinetics showing the interactions of 100 nM bi-valent binding agent consisting of ssFab' 8.1.2 and ssFab' 1.4.168 hybridized on the T40-T-Dig ssDNA-linker, i.e. linker 15, and a mixture of 100 nM ssFab' 8.1.2 and 100 nM ssFab' 1.4.168 without linker DNA. Best binding performance is only obtained with the bi-valent binding agent, whereas the mixture of the ssFab's without linker doesn't show an observable cooperative binding effect, despite the fact that the total concentration of these ssFab's had been at 200 nM.

The sensorgrams (FIG. 2-5) show a gain in both specificity and complex stability in pIGF-1R binding when ssFab' 1.4.168 and ssFab' 1.4.168 are used in form of a dual binder (=bi-valent binding agent), probably due to the underlying cooperative binding effect. Fab' 1.4.168 alone shows no cross reactivity for the pIR peptide but does not discriminate between the phosphorylated and unphosphorylated form of IGF-1R (T½ dis=3 min in both cases). Fab' 8.1.2, however, binds only to the phosphorylated version of the IGF1-R peptide but exhibits some undesired cross reactivity with phosphorylated Insulin Receptor. The Dual Binder discriminates well between the pIGF-1R peptide and both other peptides (see FIG. 4) and thus helps to overcome issues of unspecific binding. Note that the gain in specificity is lost when both Fab's are applied without linker DNA (FIG. 5). The gain in affinity of the Dual Binder towards the pIGF-1R peptide manifests in increased dissociation half times compared to individual Fab's and the Fab' mix omitting the linker DNA (FIG. 3 and FIG. 5). Although the tested Dual Binders with two different DNA linker lengths share an overall positive effect on target binding specificity and affinity, the longer linker ((III) with T40-T-Dig as a spacer) (i.e. linker 15 of example 2.4) seems to be advantageous with respect to both criteria.

2.7 Biacore™ Assay Sandwich of M-1.4.168-IgG and M-8.1.2-IgG

A Biacore™ T100 instrument (GE Healthcare) was used with a Biacore™ CM5 sensor mounted into the system. The sensor was preconditioned by a 1 min injection at 100 µl/min of 0.1% SDS, 50 mM NaOH, 10 mM HCl and 100 mM H3PO4.

The system buffer was HBS-ET (10 mM HEPES pH 7.4, 150 mM NaCl, 1 mM EDTA, 0.05% Tween® 20). The sample buffer was the system buffer.

The Biacore™ T100 System was driven under the control software V1.1.1. Polyclonal rabbit IgG antibody <IgGFCγM>R (Jackson ImmunoResearch Laboratories Inc.) at 30 µg/ml in 10 mM Na-Acetate pH 4.5 was immobilized at 10 000 RU on the flow cells 1, 2, 3, and 4, respectively, via EDC/NHS chemistry according to the manufacturer's instructions. Finally, the sensor surface was blocked with 1M ethanolamine. The complete experiment was driven at 13° C.

500 nM primary mAb M-1.004.168-IgG was captured for 1 min at 10 µl/min on the <IgGFCγM>R surface. 3 µM of an IgG fragment mixture (of IgG classes IgG1, IgG2a, IgG2b, IgG3) containing blocking solution was injected at 30 µl/min for 5 min. The peptide IGF-1R(1340-1366)[1346-pTyr; Glu (Bi-PEG-1340]amid was injected at 300 nM for 3 min at 30 µl/min. 300 nM secondary antibody M-8.1.2-IgG was injected at 30 µl min. The sensor was regenerated using 10 mM Glycine-HCl pH 1.7 at 50 µl/min for 3 min.

Figure 6:
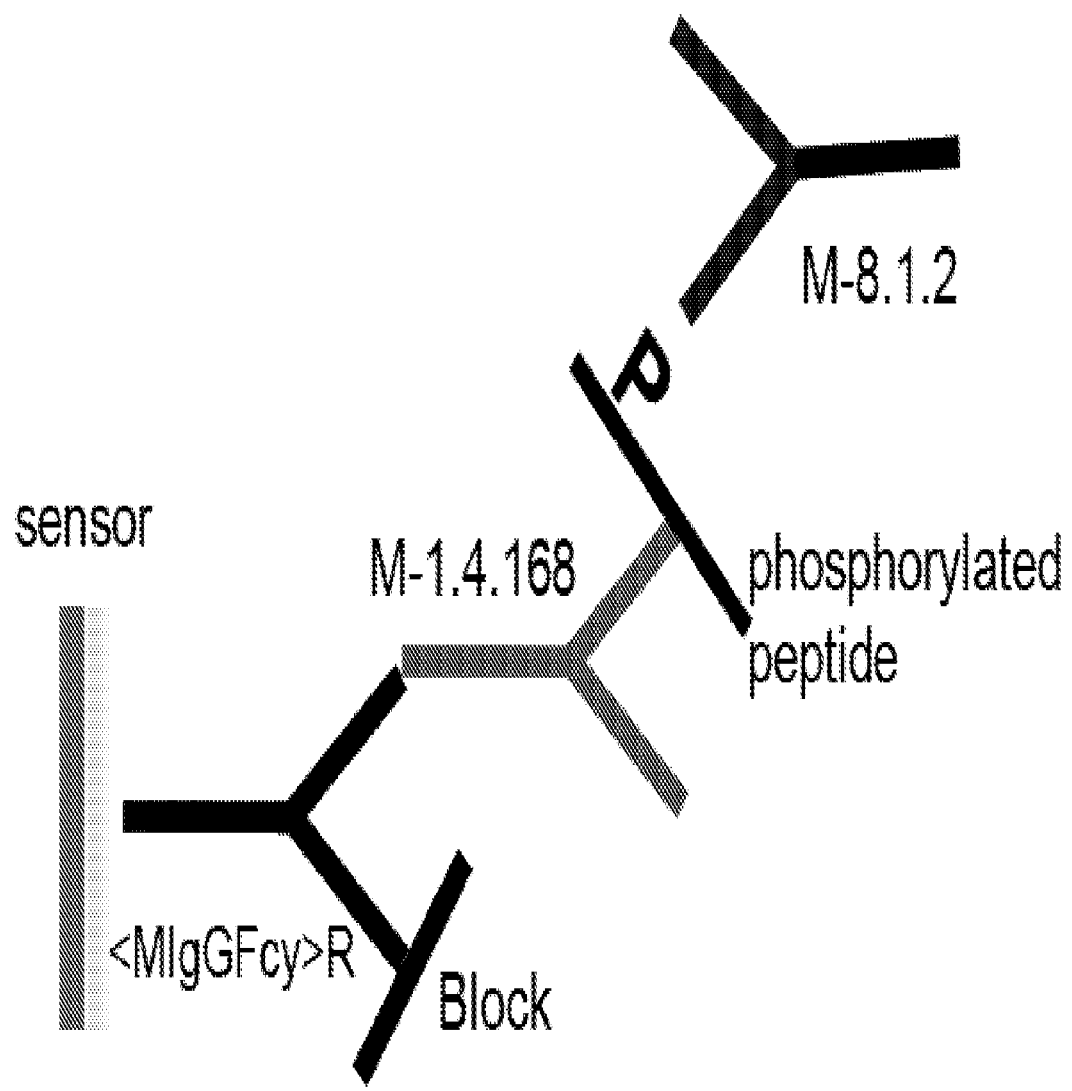
FIG. 6 presents a schematic drawing of a Biacore™ sandwich assay. This assay has been used to investigate the epitope accessibility for both antibodies on the phosphorylated IGF-1R peptide. <MIgGFcy>R presents a rabbit anti-mouse antibody used to capture the murine antibody M-1.4.168. M-1.4.168 then is used to capture the pIGF-1R peptide. M-8.1.2 finally forms the sandwich consisting of M-1.4.168, the peptide and M-8.1.2
Figure 7:
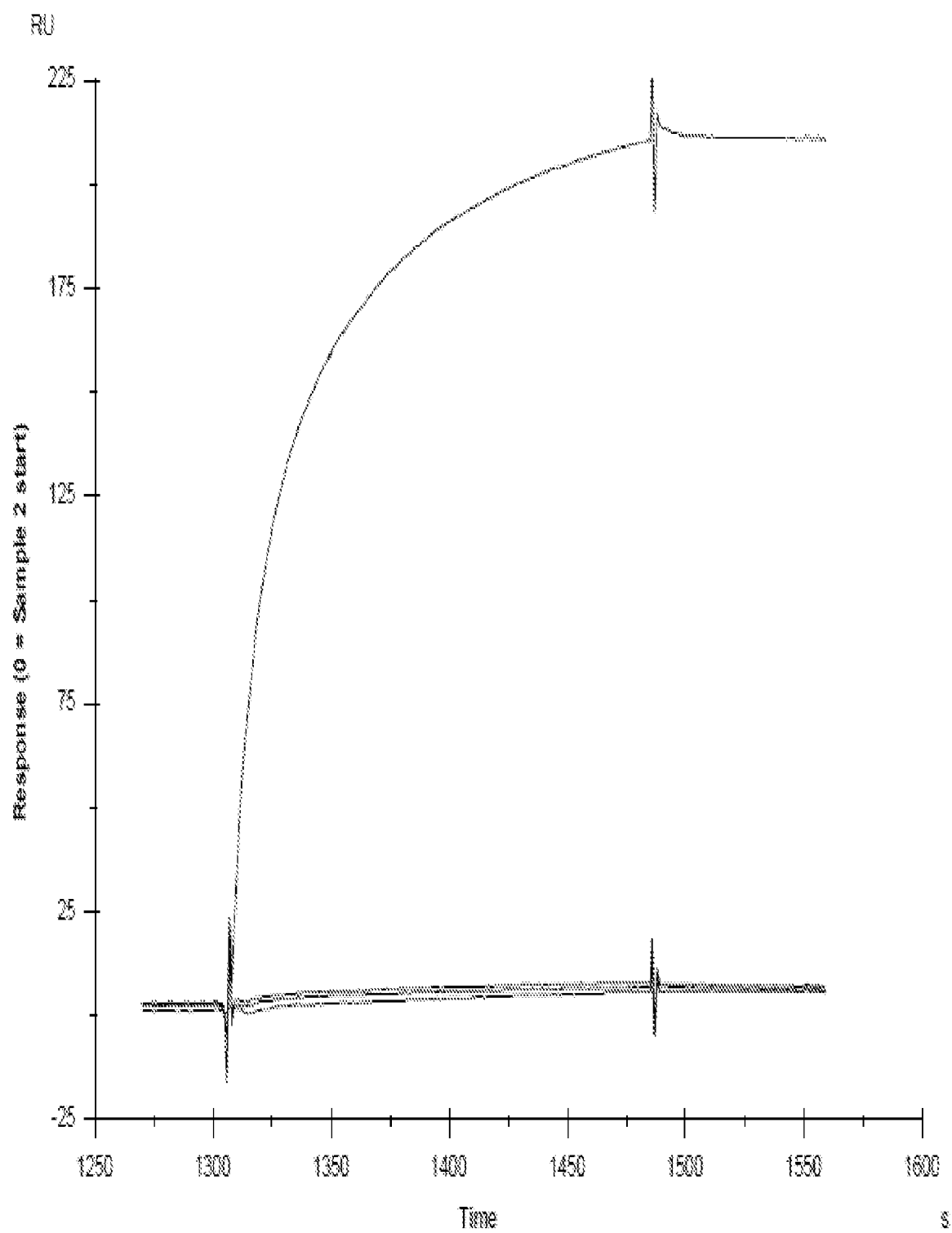
FIG. 7 presents a Biacore™ sensorgram showing the binding signal (thick line) of the secondary antibody 8.1.2. to the pIGF-1R peptide after this was captured by antibody 1.4.168 on the Biacore™ chip. The other signals (thin lines) are control signals: given are the lines from top to bottom 500 nM 8.1.2, 500 nM 1.4.168; 500 nM target unrelated antibody <CKMM>M-33-IgG; and 500 nM target unrelated control antibody <TSH>M-1.20-IgG, respectively. No binding event could be detected in any of these controls.

FIG. 6 describes the assay setup. In FIG. 7. the measurement results are given. The measurements clearly indicate, that both monoclonal antibodies are able to simultaneously bind two distinct, unrelated epitopes on their respective target peptide. This is a prerequisite to any latter experiments with the goal to generate cooperative binding events.

2.8 Biacore™ Assay Dual Binder on Sensor Surface

A Biacore™ 3000 instrument (GE Healthcare) was used with a Biacore™ SA sensor mounted into the system at T=25° C. The system was preconditioned at 100 µl/min with 3×1 min injection of 1 M NaCl in 50 mM NaOH and 1 min 10 mM HCl.

The system buffer was HBS-ET (10 mM HEPES pH 7.4, 150 mM NaCl, 1 mM EDTA, 0.05% Tween® 20). The sample buffer was the system buffer.

The Biacore™ 3000 System was driven under the control software V4.1.

124 RU amino-PEO-biotin were captured on the reference flow cell 1. 1595 RU biotinylated 14.6 kDa TO-Bi 37-mer ssDNA-Linker (I) (5'-G CAG AAG CAT TAA TAG ACT-T(-Bi)-TGG ACG ACG ATA GAA CT-3') (SEQ ID NO:7)-(Biotin-dT)-(SEQ ID NO:8) (=linker 17 of example 2.4) and 1042 RU biotinylated 23.7 kDa T40-Bi 77-mer ssDNA-Linker (II) (5'-G CAG AAG CAT TAA TAG ACT-T(20)-(Biotin-dT)-(T20)-TGG ACG ACG ATA GAA CT-3' (SEQ ID NO:7)-T20-(Biotin-dT)-T20-(SEQ ID NO:8)=linker 10 of example 2.4) were captured on different flow cells.

300 nM ssFab' 8.1.2 and 300 nM ssFab' 1.004.168 were injected into the system at 50 µl/min for 3 min. As a control only 300 nM ssFab' 8.1.2 or 300 nM ssFab' 1.004.168 was injected to test the kinetic contribution of each ssFab. As a control, buffer was injected instead of the ssFabs. The peptides pIR(1355-1382)[1361-pTyr]amid and IGF-1R (1340-1366)amid, respectively, were injected into system at 50 µl/min for 4 min, free in solution, in concentration steps of 0 nM, 4 nM, 11 nM, 33 nM (twice), 100 nM and 300 nM. In another set of experiments to measure the affinities versus the peptide pIGF-1R(1340-1366)[1346-pTyr]amid the concentration steps of 0 nM, 0.4 nM, 1.1 nM, 3.3 nM (twice), 10 nM and 30 nM were used.

The dissociation was monitored at 50 µl/min for 5.3 min. The system was regenerated after each concentration step with a 12 sec pulse of 250 mM NaOH and was reloaded with ssFab' ligand.

Figure 10:
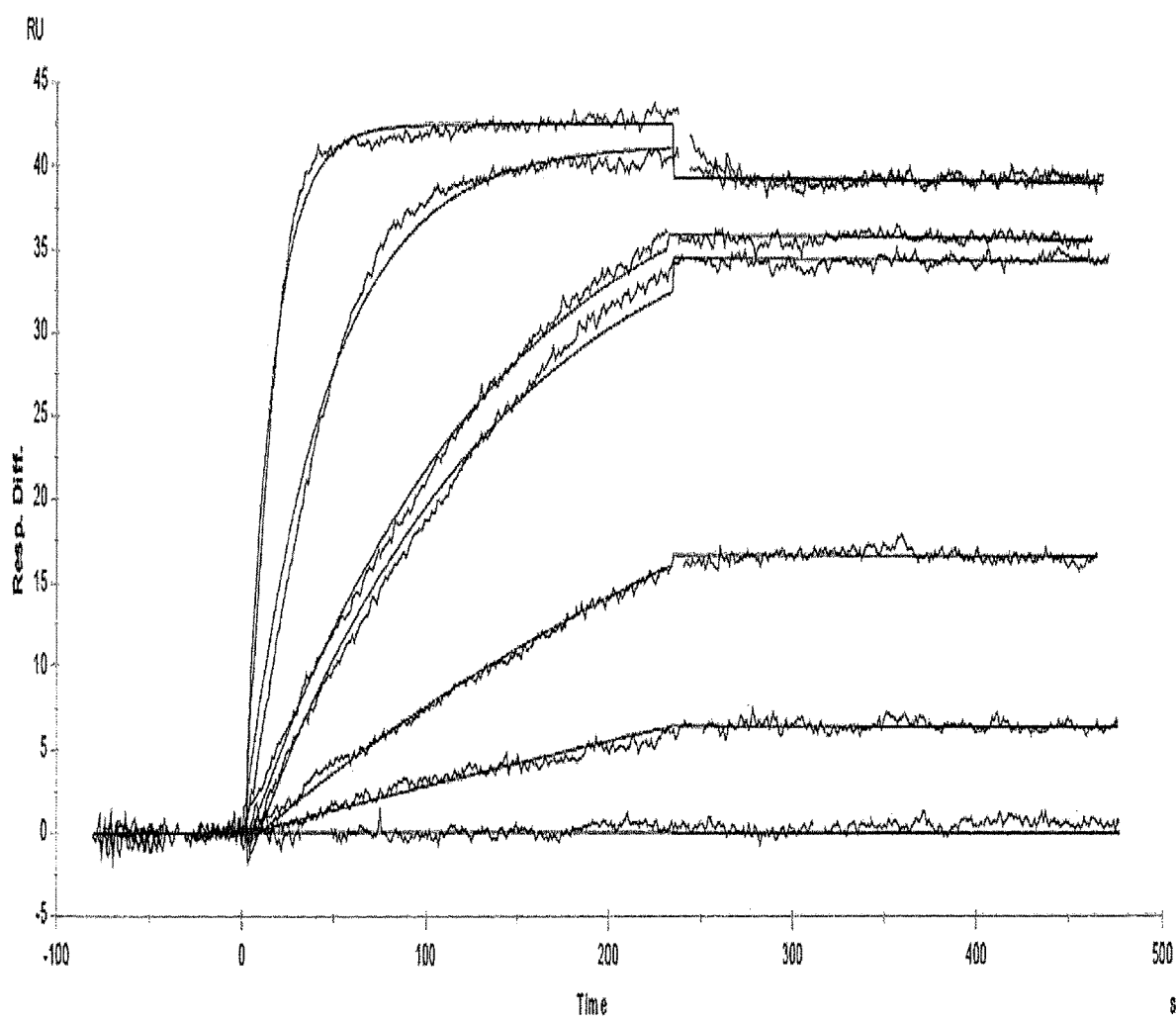
FIG. 10 presents a Biacore™ sensorgram, showing concentration dependent measurement of the T40-T-Bi dual binding agent vs. the pIGF-1R peptide (the phosphorylated IGF-1R peptide). The assay setup was as depicted in FIG. 8.

FIG. 8 schematically describes the assay setup on the Biacore™ instrument. The table given in FIG. 9 shows the quantification results from this approach. FIGS. 10, 11 and 12 depict exemplary Biacore™ results from this assay setup using the T40 dual binding agent.

The table in FIG. 9 demonstrates the benefits of the dual binder concept. The T40 dual binding agent (a dual binding agent with linker 10 of example 2.4, i.e. a linker with a spacer of T20-Biotin-dT-T20) results in a 2-fold improved antigen complex halftime (414 min) and a 3-fold improved affinity (10 pM) as compared to the T0 dual binding agent (i.e. a dual binding agent with linker 16 of example 2.4) with 192 min and 30 pM, respectively. This underlines the necessity to optimize the linker length to generate the optimal cooperative binding effect.

The T40 dual binding agent (i.e. the dual binding agent comprising the T40-Bi linker (linker 10 of example 2.4)) exhibits a 10 pM affinity versus the phosphorylated IGF-1R peptide (table in FIG. 9, FIG. 10). This is a 2400-fold affinity improvement versus the phosphorylated insulin receptor peptide (24 nM) and a 100-fold improvement versus the non-phosphorylated IGF-1R peptide.

Therefore, the goal to increase specificity and affinity by the combination of two distinct and separated binding events is achieved.

The cooperative binding effect especially becomes obvious from the dissociation rates against the phosphorylated IGF-1R peptide, where the dual binder shows 414 min antigen complex halftime, versus 0.5 min with the monovalent binder 8.1.2 alone and versus 3 min with the monovalent binder 1.4.168 alone, respectively.

Furthermore, the fully assembled construct roughly multiplies its dissociation rates kd (1/s), when compared to the singly Fab' hybridized constructs (FIGS. 10, 11, 12 and table in FIG. 9). Interestingly, also the association rate ka (1/Ms) slightly increases when compared to the single Fab' interaction events, this may be due to an increase of the construct's molecular flexibility.

A diagnostic system using an intense washing procedure should definitely foster the high performance of the T40 dual binding agent, in contrast to individual (monovalent) Fab' molecules. The hybridized construct, i.e. a bi-valent binding agent according to the present disclosure, generates a specific and quite stable binding event, while the monovalent binders more rapidly dissociate, e.g. they are more rapidly washed away.

Example 3

Bi-Valent Binding Agent to HER2

3.1 Assembly of an Anti-HER2 Bi-Valent Binding Agent

Two monoclonal antibodies binding to human HER2 (ErbB2 or p185$^{neu}$) at different, non-overlapping epitopes A and B were used. The first antibody is anti-HER2 antibody 4D5 (huMAb4D5-8, rhuMAb HER2, trastuzumab or HERCEPTIN®; see U.S. Pat. No. 5,821,337 incorporated herein by reference in its entirety).

The "4D5 epitope" is the region in the extracellular domain of ErbB2 to which the anti-HER2 antibody 4D5 (ATCC CRL 10463) binds. This epitope is close to the transmembrane domain of ErbB2.

The second antibody is anti-HER2 antibody 2C4 (Pertuzumab®). The antibody 2C4 and in particular the humanized variants thereof are described in detail in WO 01/00245 incorporated herein by reference in its entirety. 2C4 is produced by the hybridoma cell line deposited with the American Type Culture Collection, Manassass, Va., USA under ATCC HB-12697. Examples of humanized 2C4 antibodies are provided in Example 3 of WO 01/00245 (incorporated herein by reference in its entirety). The humanized anti-HER2 antibody 2C4 is also called Pertuzumab.

Pertuzumab (formerly 2C4) is the first of a new class of agents known as HER dimerization inhibitors (HDIs). Pertuzumab binds to HER2 at its dimerization domain, thereby inhibiting its ability to form active dimer receptor complexes and thus blocking the downstream signal cascade that ultimately results in cell growth and division (see Franklin, M. C., Cancer Cell 5 (2004) 317-328). Pertuzumab is a fully humanized recombinant monoclonal antibody directed against the extracellular domain of HER2.

Purification of the monoclonal antibodies from culture supernatant can be carried out using state of the art methods of protein chemistry.

The purified monoclonal antibodies are protease digested with either pre-activated papain or pepsin yielding F(ab')$_2$ fragments. These are subsequently reduced to Fab'-fragments with a low concentration of cysteamin at 37° C. The reaction is stopped by separating the cysteamin on a Sephadex G-25 column (GE Healthcare) from the polypeptide-containing part of the sample.

The obtained Fab'-fragments are conjugated with the activated ssDNA polynucleotides.

a) Anti-HER2 Antibody 4D5 Fab'-ssDNA-Conjugate

For preparation of the anti-HER2 antibody 4D5 Fab'-ssDNA-conjugate a derivative of SEQ ID NO:5 is used, i.e. 5'-AGT CTA TTA ATG CTT CTG C(=SEQ ID NO:5)-XXX-Y-Z-3', wherein X=propylene-phosphate introduced via phosphoramidite C3 (3-(4,4'-dimethoxytrityloxy)propyl-1-[(2-cyanoethyl)-(N,N-diisopropyl)]-phosphoramidite (Glen Research), wherein Y=5'-amino-modifier C6 introduced via (6-(4-monomethoxytritylamino)hexyl-(2-cyanoethyl)-(N,N-diisopropyl)-phosphoramidite (Glen Research), and wherein Z=4[N-maleinimidomethyl]cyclohexane-1-carboxy introduced via Sulfosuccinimidyl 4-[N-maleimidomethyl]cyclohexane-1-carboxylate (ThermoFischer).

b) Anti-HER2 Antibody 2C4 Fab'-ssDNA-Conjugate

For the preparation of the anti-HER2 antibody 2C4 Fab'-ssDNA-conjugate B a derivative of SEQ ID NO:6 is used, i.e. 5'-Y-Z-XXX-AGT TCT ATC GTC GTC CA-3', wherein X=propylene-phosphate introduced via Phosphoramidite C3 (3-(4,4'-Dimethoxytrityloxy)propyl-1-[(2-cyanoethyl)-(N,N-diisopropyl)]-phosphoramidite (Glen Research), wherein Y=5'-Amino-Modifier C6 introduced via (6-(4-Monomethoxytritylamino)hexyl-(2-cyanoethyl)-(N,N-diisopropyl)-phosphoramidite (Glen Research), and wherein Z=4[N-maleinimidomethyl]cyclohexane-1-carboxy introduced via Sulfosuccinimidyl 4[N-maleinimidomethyl]cyclohexane-1-carboxylate (ThermoFischer).

The polynucleotides of SEQ ID NO:5 or SEQ ID NO:6, respectively, have been synthesized by state of the art polynucleotide synthesis methods. The introduction of the maleinimido group was done via reaction of the amino group of Y with the succinimidyl group of Z which was incorporated during the solid phase polynucleotide synthesis process.

The single-stranded DNA constructs bear a thiol-reactive maleinimido group that reacts with a cysteine of the Fab' hinge region generated by the cysteamine treatment. In order to obtain a high percentage of single-labeled Fab'-fragments the relative molar ratio of ssDNA to Fab'-fragment is kept low. Purification of single-labeled Fab'-fragments (ssDNA:Fab'=1:1) occurs via anion exchange chromatography (column: MonoQ, GE Healthcare). Verification of efficient labeling and purification is achieved by analytical gel filtration chromatography and SDS-PAGE.

3.2 Biomolecular Interaction Analysis

For this experiment a Biacore T100 instrument (GE Healthcare) was used with a Biacore SA sensor mounted into the system at T=25° C. Preconditioning occurred at 100 µl/min with 3×1 min injection of 1 M NaCl in 50 mM NaOH, pH 8.0 followed by a 1 min injection of 10 mM HCl. The system buffer was HBS-EP (10 mM HEPES pH 7.4, 150 mM NaCl, 1 mM EDTA, 0.05% P 20). The sample buffer was the system buffer supplemented with 1 mg/ml CMD (Carboxymethyldextrane).

Biotinylated ss-L-DNA linkers were captured on the SA surface in the respective flow cells. Flow cell 1 was saturated with amino-PEO-Biotin (PIERCE).

40 RU of the biotinylated 37mer oligonucleotide linker (linker 3 of example 2.4) were captured on flow cell 2. 55 RU of the biotinylated 77mer oligonucleotide linker (linker 5 of example 2.4) were captured on flow cell 3. 60 RU of biotinylated 97mer oligonucleotide linker (linker 6 of example 2.4) were captured on flow cell 4.

250 nM anti-HER2 antibody 4D5-Fab'-ss-L-DNA was injected into the system for 3 min. 300 nM anti-HER2 antibody 2C4-Fab'-ss-L-DNA was injected into the system at 2 µl/min for 5 min. The DNA-labeled Fab fragments were injected alone or in combination.

As a control only 250 nM anti-HER2 antibody 4D5-Fab'-ss-D-DNA and 300 nM anti-HER2 antibody 2C4-Fab'-ss-D-DNA was injected into the system. As a further control, buffer was injected instead of the DNA-labeled Fab fragments. After hybridization of the ss-L-DNA-labeled Fab fragments on the respective ss-L-DNA bi-linkers, the analyte in solution hHER2-ECD was injected at different concentration series from 24 nM, 8 nM, 3 nM, 1 nM, 0.3 nM, 0 nM into the system for 3.5 min association phase at 100 µl/min. The dissociation phase was monitored at 100 µl/min for 15 min. The system was regenerated by a 30 sec injection at 20 µl/min of 100 mM glycine buffer (Glycine pH 11, 150 mM NaCl), followed by a second 1 min injection of water at 30 µl/min.

The signals were measured as analyte concentration-dependent, time resolved sensorgrams. The data was evaluated using the Biacore Biaevaluation software 4.1. As a fitting model a standard Langmuir binary binding model was used.

Results:

No HER2-ECD interaction could be observed when ss-D-DNA labeled Fab fragments were injected into the system, because the ss-D-DNA-labeled Fab fragments did not hybridize with spiegelmeric ss-L-DNA linkers presented on the sensor surface.

Table 3.: Kinetic results of the dual binder experiment. Linker: Surface presented biotinylated ss-L-DNA polynucleotide linker, Oligo_37 mer-Bi, Oligo_77 mer-Bi and Oligo_97 mer-Bi differing in linker length as described above. ss-L-DNA-Fab: 2C4-ss-L-DNA: anti-HER2 antibody 2C4-Fab'-ss-L-DNA labeled with 19mer-Fluorescein. 4D5-ss-L-DNA: anti-HER2 antibody 4D5-Fab'-ss-L-DNA labeled with 17mer-Fluorescein. 4D5-+2C4-ss-L-DNA relates to the surface bound dual binding agent comprising the combination of both monovalent anti-HER2-antibody fragments.

In Table 3 the following abbreviations are used: LRU: mass in response units, which is hybridized on the sensor surface. Antigen: a 87 kDa HER2-ECD was used as analyte in solution. ka: association rate in (1/Ms). kd: dissociation rate in (1/s). t½ diss: antigen complex halftime calculated in hours according to the solution ln(2)/kd*3600 of a first order kinetic equation. KD: affinity in molar. KD: affinity calculated in picomolar. Rmax: Maximum analyte response signal at saturation in response units (RU). MR: Molar Ratio, indicating the stoichiometry of the interaction. Chi2, U-value: quality indicator of the measurements.

presence of a simultaneous, cooperative binding event of both Fab fragments. The dual binder counts is a single molecule with a 1:1 Langmuir binding stoichiometry. Despite having 2 independently binding HER2 interfaces no inter molecule binding between one dual binder and two HER2 domains can be detected.

The avidity constants for synergizing pairs of monoclonal antibodies or for a chemically cross-linked bispecific F(ab')2 is generally only up to 15 times greater than the affinity constants for the individual monoclonal antibodies, which is significantly less than the theoretical avidity expected for ideal combination between the reactants (Cheong, H. S., et al., Biochem. Biophys. Res. Commun. 173 (1990) 795-800). Without being bound by this theory one reason for this might be that the individual epitope/paratope interactions involved in a synergistic binding (resulting in a high avidity) must be orientated in a particular way relative to each other for optimal synergy.

Furthermore, the data presented in Table 3 provides evidence, that the short 37mer linker, which consists just from the ss-L-DNA hybridization motives doesn't show enough flexibility or/and linker length to produce the cooperative binding effect. The 37mer linker is a rigid, double helix L-DNA construct. The hybridization generates a double L-DNA helix, which is shorter and less flexible than

TABLE 3

| Linker | ss-L-DNA-Fab | LRU | Antigen | $k_a$ 1/Ms | $k_d$ 1/s | t½-diss hours | $K_D$ M | $K_D$ pM | $R_{max}$ RU | MR | Chi² RU² |
|---|---|---|---|---|---|---|---|---|---|---|---|
| Oligo_35mer-Bi | 4D5- + 2C4-ss-L-DNA | 84 | Her2-ECD | 5.9E+05 | 6.7E−05 | 3 | 1.1E−10 | 100 | 59 | 0.9 | 0.2 |
| Oligo_35mer-Bi | 4D5-ss-L-DNA | 16 | Her2-ECD | 4.0E+05 | 3.4E−05 | 6 | 8.5E−11 | 100 | 29 | 1.2 | 0.1 |
| Oligo_35mer-Bi | 2C4-ss-L-DNA | 31 | Her2-ECD | 3.3E+05 | 3.6E−05 | 5 | 1.1E−10 | 100 | 26 | 0.6 | 0.03 |
| Oligo_75mer-Bi | 4D5- + 2C4-ss-L-DNA | 87 | Her2-ECD | 5.1E+05 | 4.6E−08 | 4164 | 9.1E−14 | 0.1 | 65 | 1.0 | 0.1 |
| Oligo_75mer-Bi | 4D5-ss-L-DNA | 16 | Her2-ECD | 2.9E+05 | 6.1E−05 | 3 | 2.1E−10 | 200 | 31 | 1.3 | 0.04 |
| Oligo_75mer-Bi | 2C4-ss-L-DNA | 29 | Her2-ECD | 3.8E+05 | 6.3E−05 | 3 | 1.6E−10 | 200 | 32 | 0.7 | 0.03 |
| Oligo_95mer-Bi | 4D5- + 2C4-ss-L-DNA | 76 | Her2-ECD | 5.0E+05 | 4.9E−08 | 3942 | 9.9E−14 | 0.1 | 58 | 1.0 | 0.1 |
| Oligo_95mer-Bi | 4D5-ss-L-DNA | 14 | Her2-ECD | 3.0E+05 | 9.5E−05 | 2 | 3.1E−10 | 300 | 28 | 1.3 | 0.03 |
| Oligo_95mer-Bi | 2C4-ss-L-DNA | 28 | Her2-ECD | 3.8E+05 | 6.8E−05 | 3 | 1.8E−10 | 300 | 27 | 0.6 | 0.03 |

In the above Table 35mer, 75mer and 95mer, respectively should read 37mer, 77mer and 97mer, respectively.

The biacore data for the 37mer dual binder HER2-ECD interaction (i.e. for a binder with a linker consisting solely the hybridization sequences motives attached to the binders and a central biotinylated thymidin) indicate that this dual binding agent shows no improvement in kinetic performance. This is most likely due to the insufficient linker length and the lack in flexibility of the 37mer linker.

The biacore data for the 77mer dual binder HER2-ECD interaction (i.e. for a binder with a linker comprising twice 20 thymidines a central biotinylated thymidin to increase the linker length) indicate, that this dual binding agent shows a dramatic improvement in its kinetic performance. This is most likely due to an optimal linker length and the flexibility of this 77mer linker.

The biacore data for the 97mer dual binder HER2-ECD interaction (i.e. for a binder with a linker comprising twice 30 thymidines a central biotinylated thymidin to increase the linker length) indicate, that this dual binding agent shows a dramatic improvement in its kinetic performance. This is most likely due to an optimal linker length and the flexibility of this 97mer linker.

The data in Table 3 provide evidence for the presence of a cooperative binding event. Despite the Rmax values of the fully established dual binders are roughly double the signal height of the singly Fab-armed constructs, the Molar Ratio values are exactly 1 (MR=1). This is a clear evidence for the the ss-L-DNA sequence. The helix shows reduced degrees of freedom and can be seen as a rigid linker construct. Table 3 shows, that the 37mer linker isn't able to generate a cooperative binding event. The fully established 37mer dual binder shows the same affinity like only the singly hybridized constructs.

Extending the linker length by a highly flexible poly-T ss-L-DNA to form a 77mer and a 97mer, respectively, provides for an increase in affinity and especially in antigen complex stability kd (1/s).

The chi2 values indicate a high quality of the measurements. All measurements show extremely small errors. The data can be fitted to a Langmuir 1:1 fitting model residuals deviate only +/−1 RU, small chi2 values and only 10 iterative calculations were necessary for obtaining the data.

A cooperative binding effect works according to the physical law, that the free binding energies ΔG1 and ΔG2 summarize. The affinities multiply: Kdcoop=KD1×KD2. Furthermore, the dissociation rates also multiply: kd coop=kd1×kd 2. This is exactly observable in the 77mer and 97mer linker experiment. This results in very long complex half-lifes of 4146 hours (173 days) and 3942 hours (164 days), respectively. The affinities are in the range of 100 fmol/l. It is obvious, that a cooperative binding event occurs.

The association rates of all dual binding agents are faster, when compared to the singly hybridized constructs. Despite showing a higher molecular weight the association rate increases.

Here we could show, that tratsuzumab and pertuzumab linked together in a complex as reported herein simultaneously binds to the HER-2 extracellular domain (ECD). Both Fab fragments bind to genuine epitopes on the HER2-ECD. Additionally both Fab fragments strongly differ in their binding angles. By using the optimal 77mer linker (about 30 nm in length) ss-L-DNA and its beneficial flexibility and length properties a cooperative binding event could be shown.

Hence cooperative binding between Herceptin-Fab and Pertuzumab-Fab linked together via a highly flexible ss-L-DNA linker could be shown.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A binding agent comprising Formula: A-a':a-S-b:b'-B: X(n), wherein A is a monovalent antibody Fab' fragment comprising a heavy chain variable region (VH) and a light chain variable region (VL) wherein (a) the VH comprises SEQ ID NO:1 and the VL comprises SEQ ID NO:2 or (b) the VH comprises SEQ ID NO:3 and the VL comprises SEQ ID NO:4; B is a monovalent antibody Fab' fragment comprising a heavy chain variable region (VH) and a light chain variable region (VL) wherein (a) the VH comprises SEQ ID NO:1 and the VL comprises SEQ ID NO:2 or (b) the VH comprises SEQ ID NO:3 and the VL comprises SEQ ID NO:4; S is a spacer of at least 1 nm in length; (n) is an integer and at least 1; represents a covalent bond; a' is a single-stranded DNA oligonucleotide comprising SEQ ID NO:5; b' is a single-stranded DNA oligonucleotide comprising SEQ ID NO:6; wherein the first Fab' is conjugated to a single-stranded DNA oligonucleotide of SEQ ID NO:5, wherein the second Fab' is conjugated to a single-stranded DNA oligonucleotide of SEQ ID NO:6; a-S-b is a biotinylated linker wherein a is SEQ ID NO:7, b is SEQ ID NO:8, and S is selected from the group consisting of (T40), Tn(biotin-dT)Tn wherein Tn is 0 to 30, Spacer C18-(biotin-dT)-Spacer C18, (Spacer C18)2-(biotin-dT)-(Spacer C18)2, (Spacer C18)3-(biotin-dT)-(Spacer C18)3, (Spacer C18)4-(biotin-dT)-(Spacer C18)4, Tn(Dig-dT)Tn wherein Tn is 0 to 20, and (GGGGS)n (SEQ ID NO:13) wherein n is at least 1; a':a is a binding pair; b:b' is a binding pair, wherein a' and a do not interfere with the binding of b to b' and b' and b do not interfere with the binding of a' to a; (: X) denotes a functional moiety bound either covalently or via a binding pair to at least one of a', a, b, b' or S; and linker a-S-b has a length of 6 to 100 nm.

2. The binding agent of claim 1, wherein the spacer S is 1 to 95 nm in length.

3. The binding agent of claim 1, wherein the a':a binding pair and the b:b' binding pair are hybridizing nucleic acid sequences and wherein the different hybridizing nucleic acid sequences of the a':a binding pair does not hybridize with the b:b' binding pair.

4. The binding agent of claim 1, wherein X is a functional moiety selected from the group consisting of a labeling group, a binding group and an effector group.

5. The binding agent of claim 1, wherein the functional moiety X is bound to a, b, or S.

6. The binding agent of claim 1, wherein the functional moiety X is bound to the spacer S.

7. The binding agent of claim 1, wherein the functional moiety X is covalently bound to the spacer S.

8. The binding agent of claim 1, wherein the functional moiety X is bound to the spacer S via a hybridizing nucleic acid.

* * * * *

SEQUENCE LISTING

```
<160> NUMBER OF SEQ ID NOS: 15

<210> SEQ ID NO 1
<211> LENGTH: 122
<212> TYPE: PRT
<213> ORGANISM: Mus musculus

<400> SEQUENCE: 1

Gln Cys Asp Val Lys Leu Val Glu Ser Gly Gly Gly Leu Val Lys Pro
1               5                   10                  15

Gly Gly Ser Leu Lys Leu Ser Cys Ala Ala Ser Gly Phe Thr Phe Ser
            20                  25                  30

Asp Tyr Pro Met Ser Trp Val Arg Gln Thr Pro Glu Lys Arg Leu Glu
        35                  40                  45

Trp Val Ala Thr Ile Thr Thr Gly Gly Thr Tyr Thr Tyr Tyr Pro Asp
    50                  55                  60

Ser Ile Lys Gly Arg Phe Thr Ile Ser Arg Asp Asn Ala Lys Asn Thr
65                  70                  75                  80

Leu Tyr Leu Gln Met Gly Ser Leu Gln Ser Glu Asp Ala Ala Met Tyr
                85                  90                  95

Tyr Cys Thr Arg Val Lys Thr Asp Leu Trp Trp Gly Leu Ala Tyr Trp
            100                 105                 110

Gly Gln Gly Thr Leu Val Thr Val Ser Ala
        115                 120

<210> SEQ ID NO 2
<211> LENGTH: 116
<212> TYPE: PRT
<213> ORGANISM: Mus musculus

<400> SEQUENCE: 2

Gln Leu Val Leu Thr Gln Ser Ser Ser Ala Ser Phe Ser Leu Gly Ala
1               5                   10                  15

Ser Ala Lys Leu Thr Cys Thr Leu Ser Ser Gln His Ser Thr Tyr Thr
            20                  25                  30

Ile Glu Trp Tyr Gln Gln Pro Leu Lys Pro Pro Lys Tyr Val Met
        35                  40                  45

Glu Leu Lys Lys Asp Gly Ser His Thr Thr Gly Asp Gly Ile Pro Asp
    50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ser Ile Tyr Ile Cys Gly Val Gly Asp
                85                  90                  95

Thr Ile Lys Glu Gln Phe Val Tyr Val Phe Gly Gly Gly Thr Lys Val
            100                 105                 110
```

Thr Val Leu Gly
        115

<210> SEQ ID NO 3
<211> LENGTH: 121
<212> TYPE: PRT
<213> ORGANISM: Mus musculus

<400> SEQUENCE: 3

Glu Val Gln Leu Gln Gln Ser Gly Pro Ala Leu Val Lys Pro Gly Ala
1               5                   10                  15

Ser Val Lys Met Ser Cys Lys Ala Ser Gly Phe Thr Phe Thr Ser Tyr
            20                  25                  30

Val Ile His Trp Val Lys Gln Lys Pro Gly Gln Gly Leu Glu Trp Ile
        35                  40                  45

Gly Tyr Leu Asn Pro Tyr Asn Asp Asn Thr Lys Tyr Asn Glu Lys Phe
    50                  55                  60

Lys Gly Lys Ala Thr Leu Thr Ser Asp Arg Ser Ser Ser Thr Val Tyr
65                  70                  75                  80

Met Glu Phe Ser Ser Leu Thr Ser Glu Asp Ser Ala Val Tyr Phe Cys
                85                  90                  95

Ala Arg Arg Gly Ile Tyr Ala Tyr Asp His Tyr Phe Asp Tyr Trp Gly
            100                 105                 110

Gln Gly Thr Ser Leu Thr Val Ser Ser
        115                 120

<210> SEQ ID NO 4
<211> LENGTH: 106
<212> TYPE: PRT
<213> ORGANISM: Mus musculus

<400> SEQUENCE: 4

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Asn Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Val Thr Ser Tyr Ser Leu Thr Ile Ser Arg Met Glu Ala Glu
65                  70                  75                  80

Asp Ala Ala Thr Tyr Tyr Cys Gln Gln Trp Ser Tyr Pro Leu Thr
                85                  90                  95

Phe Gly Ala Gly Thr Lys Leu Glu Leu Lys
            100                 105

<210> SEQ ID NO 5
<211> LENGTH: 17
<212> TYPE: DNA
<213> ORGANISM: Artificial Sequence
<220> FEATURE:
<223> OTHER INFORMATION: 17mer ssDNA

<400> SEQUENCE: 5
agttctatcg tcgtcca                                                  17

<210> SEQ ID NO 6
<211> LENGTH: 19

<212> TYPE: DNA
<213> ORGANISM: Artificial Sequence
<220> FEATURE:
<223> OTHER INFORMATION: 19mer ssDNA

<400> SEQUENCE: 6
agtctattaa tgcttctgc                                                19

<210> SEQ ID NO 7
<211> LENGTH: 19
<212> TYPE: DNA
<213> ORGANISM: Artificial Sequence
<220> FEATURE:
<223> OTHER INFORMATION: complementary 19mer ssDNA

<400> SEQUENCE: 7
gcagaagcat taatagact                                                19

<210> SEQ ID NO 8
<211> LENGTH: 17
<212> TYPE: DNA
<213> ORGANISM: Artificial Sequence
<220> FEATURE:
<223> OTHER INFORMATION: complementary 17mer ssDNA

<400> SEQUENCE: 8
tggacgacga tagaact                                                  17

<210> SEQ ID NO 9
<211> LENGTH: 33
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (16)..(17)
<223> OTHER INFORMATION: bAla

<400> SEQUENCE: 9

Glu Arg Ala Glu Gln Gln Arg Ile Arg Ala Glu Arg Glu Lys Glu Xaa
1               5                   10                  15

Xaa Ser Leu Lys Asp Arg Ile Glu Lys Arg Arg Arg Ala Glu Arg Ala
            20                  25                  30

Glu

<210> SEQ ID NO 10
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (16)..(17)
<223> OTHER INFORMATION: Amino-trioxa-octanoic-acid (X represents
      Amino-trioxa-octanoic-acid)

<400> SEQUENCE: 10

Ser Leu Lys Asp Arg Ile Glu Arg Arg Arg Ala Glu Arg Ala Glu Xaa
1               5                   10                  15

Xaa Glu Arg Ala Glu Gln Gln Arg Ile Arg Ala Glu Arg Glu Lys Glu
            20                  25                  30

<210> SEQ ID NO 11
<211> LENGTH: 27

```
<212> TYPE: PRT
<213> ORGANISM: Artificial Sequence
<220> FEATURE:
<223> OTHER INFORMATION: Synthetic peptide

<400> SEQUENCE: 11

Phe Asp Glu Arg Gln Pro Tyr Ala His Met Asn Gly Gly Arg Lys Asn
1               5                   10                  15

Glu Arg Ala Leu Pro Leu Pro Gln Ser Ser Thr
            20                  25

<210> SEQ ID NO 12
<211> LENGTH: 28
<212> TYPE: PRT
<213> ORGANISM: Artificial Sequence
<220> FEATURE:
<223> OTHER INFORMATION: Synthetic peptide

<400> SEQUENCE: 12

Tyr Glu Glu His Ile Pro Tyr Thr His Met Asn Gly Gly Lys Lys Asn
1               5                   10                  15

Gly Arg Ile Leu Thr Leu Pro Arg Ser Asn Pro Ser
            20                  25

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide (Spacer)

<400> SEQUENCE: 13

Gly Gly Gly Gly Ser
1               5

<210> SEQ ID NO 14
<211> LENGTH: 9
<212> TYPE: PRT
<213> ORGANISM: Artificial Sequence
<220> FEATURE:
<223> OTHER INFORMATION: HA-Tag

<400> SEQUENCE: 14

Tyr Pro Tyr Asp Val Pro Asp Tyr Ala
1               5

<210> SEQ ID NO 15
<211> LENGTH: 15
<212> TYPE: PRT
<213> ORGANISM: Artificial Sequence
<220> FEATURE:
<223> OTHER INFORMATION: Avi-Tag

<400> SEQUENCE: 15

Gly Leu Asn Asp Ile Phe Glu Ala Gln Lys Ile Glu Trp His Glu
1               5                   10                  15
```